(12) United States Patent
Daniel et al.

(10) Patent No.: US 7,108,696 B2
(45) Date of Patent: Sep. 19, 2006

(54) BONE-TREATMENT INSTRUMENT AND METHOD

(75) Inventors: Steven A. Daniel, Fremont, CA (US); Daniel J. Balbierz, Redwood City, CA (US); Robert D. Russell, Isle of Palms, SC (US); Robert Pearson, San Jose, CA (US); Andres Tamayo, Stanford, CA (US); Takehito Jimbo, San Bruno, CA (US); Karen Frischmeyer, Palo Alto, CA (US)

(73) Assignee: Rita Medical Systems, Inc., Fremont, CA (US)

( * ) Notice: Subject to any disclaimer, the term of this patent is extended or adjusted under 35 U.S.C. 154(b) by 216 days.

(21) Appl. No.: 10/668,433

(22) Filed: Sep. 22, 2003

(65) Prior Publication Data
US 2004/0059328 A1 Mar. 25, 2004

Related U.S. Application Data

(63) Continuation of application No. 10/044,081, filed on Jan. 11, 2002, now Pat. No. 6,622,731.

(60) Provisional application No. 60/261,297, filed on Jan. 11, 2001.

(51) Int. Cl.
*A61B 18/18* (2006.01)
*A61B 17/50* (2006.01)

(52) U.S. Cl. .................................. 606/41; 607/101

(58) Field of Classification Search ............. 606/41, 606/42, 45–50; 607/101, 102
See application file for complete search history.

(56) References Cited

U.S. PATENT DOCUMENTS

| | | | |
|---|---|---|---|
| 5,672,173 A * | 9/1997 | Gough et al. ............. 606/41 |
| 5,697,536 A | 12/1997 | Eggers et al. | |
| 5,814,066 A | 9/1998 | Spotnitz | |
| 5,827,276 A * | 10/1998 | LeVeen et al. ............. 606/41 |
| 6,033,401 A | 3/2000 | Edwards et al. | |
| 6,241,725 B1 * | 6/2001 | Cosman ..................... 606/41 |
| 6,264,651 B1 * | 7/2001 | Underwood et al. ......... 606/32 |
| 6,302,898 B1 | 10/2001 | Edwards et al. | |

(Continued)

OTHER PUBLICATIONS

Strube H.D. et al., "Diagnostic and therapeutic problems in tumors of the bones of the hand", *Handchirurgie* 1979; 11(2):113-118 (abstract only).

(Continued)

*Primary Examiner*—Michael Peffley
(74) *Attorney, Agent, or Firm*—Jacqueline F. Mahoney; Peter J. Dehlinger; Perkins Coie LLP

(57) ABSTRACT

Ablation devices and associated methods are provided for use in palliative treatment of a bone tumor on or in a compact bone region. The bone treatment devices include an elongate probe having a distal end. A proximal end of the probe supports placement in a location at or adjacent to the bone tumor. Electrodes are carried within the probe for deployment from the distal end into the bone tumor. The electrodes may be shapable to create, upon deployment, an array of electrodes that defines a geometric area within the bone tumor. Application of energy, for example energy from a radio frequency (RF) source, to the area of the bone tumor via the electrodes destroys at least a portion of the nerve receptors located in or adjacent to the tumor and produces a reduction in pain associated with the bone tumor. Liquid, such as a polymer in liquid form, may be injected through an electrode needle, with electrode heating being employed to allow introduction of the polymer solution through the needle and/or hardening at the site of injection.

23 Claims, 31 Drawing Sheets

U.S. PATENT DOCUMENTS 6,478,793 B1 * 11/2002 Cosman et al. ............... 606/34
6,562,059 B1    5/2003 Edwards et al.
6,602,248 B1 *  8/2003 Sharps et al. ................. 606/32

OTHER PUBLICATIONS

Matsui, N. et al., "Hyperthermia in malignant tumors of the extremities—ecxperimental heating by a radiofrequency applicator and its clihical significance", *Gan To Kagaku Ryoho* 1989; 16(4 Pt 2-3): 1788-1794, (abstract only).

Nagata, Y. et al., "Transcatheter arterial embolization for malignant osseous and soft tissue sarcomas", *Cardiovascular & Interventional Radiology* 1998; 21(3):205-207.

Van Oyen, P., "Pain treatment in metastatic prostatic carcinoma by radiofrequeney thermolesion on the pituitary gland", *Prog Clin Biol Res* 1987; 243B:497-500.

Dupuy, D.E., "Radiofrequency ablation: an outpatient percutaneous treatment", *Med Health R I* 1999; 82(6):213-216.

Dupuy, D.E. et al., "Radiofrequency ablation of spinal tumors: temperature distribution in the spinal canal", *Am J Roentgenol* 2000; 175(5):1263-1266.

Barei, D.P. et al., "Percutaneous radiofrequency ablation of osteoid osteoma", *Clin Orthop* 2000; Apr(373):115-124.

Rosenthal, D.I. et al., "Osteoid osteoma: percutaneous radio-frequency ablation", *Radiology* 1995; 197(2):451-454.

Sluga, M. et al., "Local and systemic control after ablative and limb sparing surgery in patients with osteosarcoma", *Clin Orthop* 1999; No. 358:120-127.

Rosenthal, D.I. et al., "Ablation of osteoid osteomas with a percutaneously placed electrode: a new procedure", *Radiology* 1992; 183(1):29-33.

* cited by examiner

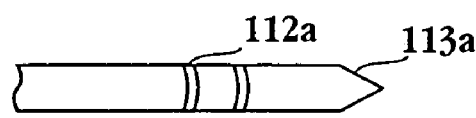
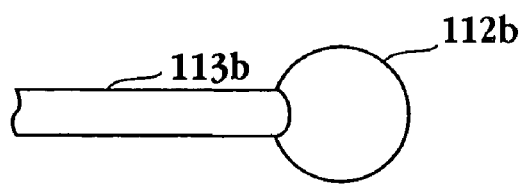
Fig. 7A                         Fig. 7B
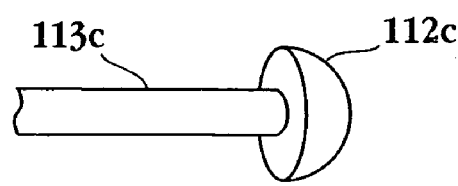
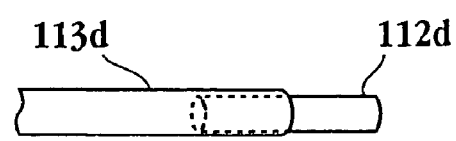
Fig. 7C                         Fig. 7D
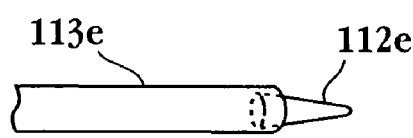
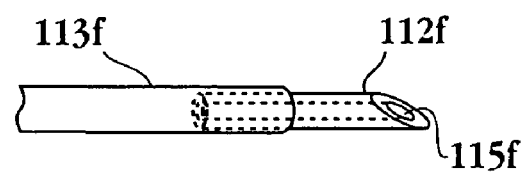
Fig. 7E                         Fig. 7F
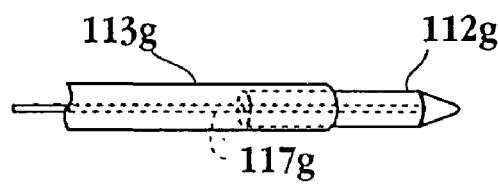
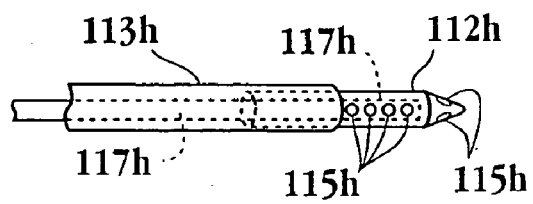
Fig. 7G                         Fig. 7H

| Pt. No. | Age, M/F | Primary Neoplasm | Treatment Location | Lesion size CC_REXAP (cm) | | | Session No. | Deployment Diameter (cm) | Time at Target Temperature (min) | Total RF time (min) | Total Procedure Time (min) |
|---|---|---|---|---|---|---|---|---|---|---|---|
| 1 | 57, F | Renal | Ilium | 5.5 | 4.4 | 4.3 | 1 | 3,3,2,3,3 | 5,5,5,5,5 | 56 | 150 |
| 2 | 54, M | Melanoma | Tibia | 1.3 | 1.3 | 1.3 | 1 | 2,2,3,3 | 10,10,10,10 | 50 | 195 |
| 3 | 65, M | Lung | Rib, Body wall and Liver | 6.3 | 4.3 | 8.3 | 1 | 4,3,3,3,5,3 | 15,10,10,10,25,10 | 95 | 187 |
| 4 | 68, M | Colorectal | Sacrum | 10.0 | 10.5 | 7.0 | 1 | 4,4,4,4,4,4,4 4,4,4,4,4,4,4 | 10,8,5,5,5,5,5 5,5,5,5,5,5,5 | 60 | 180 |
| | | | | | | | | | | 63 | 120 |
| 5 | 68, F | Colorectal | Rib | 2.3 | 1.0 | 1.8 | 2 | 1,1 | 5,5 | 16 | 120 |
| 6 | 67, F | Endometrial | Pubic symphasis | 3.5 | 3.9 | 2.9 | 1 | 3,3,3,5 | 7,7,10,20 | 54 | 130 |
| 7 | 66, M | Bladder | Ilium | 3.5 | 6.4 | 6.3 | 1 | 3,3,4,2,4,5 | 10,30,10,4,15,30 | 31 | 130 |
| 8 | 65, M | Renal | Ilium | 5.0 | 3.0 | 4.0 | 1 | 3,3,3,3 | 5,5,5,5 | 30 | 130 |
| 9 | 78, F | Colorectal | Vertebral, Body and Rib | 5.0 | 8.0 | 3.0 | 1 | 2,2,3 | 5,5,7 | 23 | 90 |
| 10 | 68, F | Colorectal | Sacrum | 10.0 | 7.5 | 9.1 | 1 | 2,3,4,4,3 | 5,5,5,5,5 | 36 | 133 |
| 11 | 66, M | Renal | Ilium | 3.1 | 2.6 | 3.5 | 1 | 3,5,5,5 | 3,8,8,8,8 | 41 | 105 |
| 12 | 56, M | Renal | Talus | | | | 1 | 3,3 | 8,8 | 32 | 75 |

Fig. 36

BONE-TREATMENT INSTRUMENT AND METHOD

RELATED APPLICATION

This application is a continuation of U.S. patent application Ser. No. 10/044,081, filed on Jan. 11, 2002, now U.S. Pat. No. 6,622,731, which claims the benefit of U.S. Provisional Patent Application No. 60/261,297, filed Jan. 11, 2001, both of which are incorporated herein by reference in their entirety.

TECHNICAL FIELD

This invention relates generally to palliative treatment of bone, bone tumors and lesions, and diseases of the bone.

BACKGROUND

A variety of diseases can affect bone tissue resulting in lesions and tumors of the bone. Primary bone tumors, either benign or malignant, may originate in cartilage cells, osteoblastic (osteoid- or bone-forming) cells, fibroblastic cells, primitive mesenchymal cells, and hematopoietic cells, as well as nerve and vascular tissue, notocordal remnants, and other sites. Benign tumors of the bone include enchondroma, osteochondroma, osteoid osteoma and osteoblastoma, giant cell tumor (also malignant), chondroblastoma. Malignant tumors include multiple myeloma, metastatic carcinoma central chondrosarcoma, osteogenic sarcoma, osteogenic sarcoma medullary fibrosarcoma peripheral chondrosarcoma and Ewing's sarcoma.

The most common forms of malignant bone tumor are attributable to metastatic disease. In fact, bone is the third most common site of metastatic disease. Treatments for bone metastases are limited in nature and generally only palliative.

Pain is one of the more prevalent and debilitating complications of bone tumors and lesions. Approximately 40% of patients with cancer develop metastatic disease; of these patients, 50% have poorly controlled pain. Unfortunately, achieving adequate pain control is often difficult and as a result, quality of life for these patients is poor. Various therapies may be employed in an attempt to provide palliative pain relief including chemotherapy, hormonal therapy, localized radiation, systemic radioisotope therapy, and surgery. Unfortunately, some patients fail to derive satisfactory pain relief with these therapies and relief, when achieved, may not occur until four to twelve weeks after the initiation of the treatment.

Pain management in terminally ill patients with metastases involving bone can be challenging. The conventional therapies may not be viable options for numerous reasons. For example, the limited efficacy or toxic side-effects of chemotherapeutic agents is problematic. Furthermore, localized radiation may not be possible due to radiation resistance of the neoplasms or limitations of further radiation of normal structures. Moreover, the patient may be either a poor surgical candidate or the patient may refuse surgery. When these methods are not possible, or are not effective, analgesic medications remain as the only current alternative therapy for pain relief. Despite these measures, the quality of life for these patients is often poor because of intolerable pain.

There is thus a need for a treatment method effective to palliate pain in patients suffering from bone-tumor associated pain.

SUMMARY

The invention includes, in one aspect, a system for palliatively treating a pain-causing tumor on or in a bone. The system includes an instrument having a distal-end structure adapted to be inserted into the bone tumor, and activatable to ablate tumor tissue, and connecting structure for connecting the distal-end structure to an activating device. One preferred embodiment employs an electrode as the distal-end structure and connecting structure for connecting the electrode to a source of RF current.

In one general embodiment, the instrument is composed of a probe or introducer with a distal end, and at least one electrode movable from a retracted position within the probe to a deployed position extending from the probe's distal end, forming the distal-end structure when deployed. The instrument may contain a plurality of curved, deployable electrodes, which, when deployed, create an array of deployed electrodes that defines a substantially two-dimensional surface expanse or a three-dimensional volume within the tumor. For example, for use in treating a bone tumor on the exterior or interior surface of a compact region of a bone, the electrodes, when deployed, may form an array that defines a two-dimensional expanse that is coextensive with a portion of the surface of the compact bone region surrounded by the tumor. As other examples, the deployed electrodes may form a three-dimensional volume that encompasses the instrument's distal tip, or three-dimensional volume that converges at the distal tip. The curvature of one or more of the electrodes may be shapable, prior to use, such that the electrode(s), when inserted into the tumor, define a selected geometry within the tumor.

In one general embodiment, at least one of the electrodes is a needle forming a conduit through which liquid can be injected into the tumor, either prior to, during, or following tumor ablation. This embodiment includes additional connecting structure for connecting the needle to a source of liquid under pressure.

In another aspect, the invention includes a method of palliatively treating a pain-causing bone tumor of the type indicated above. The method includes the steps of locating the position of the bone tumor, positioning against or adjacent the located bone tumor, the distal end of an instrument having a distal-end structure which can be activated to ablate tissue, and with the structure inserted into or against the bone tumor, activating the structure under conditions effective to ablate at least a portion of the tumor. One preferred embodiment employs an electrode as the distal-end structure and connecting structure for connecting the electrode to a source of RF current. The instrument used in the method may have single or plural deployable electrodes, with various geometries in the deployed state, as discussed above.

In one general embodiment, which preferably employs a distal-end electrode and an RF or other heat-producing activating source, the method further includes injecting a liquid into the tumor, either prior to, during, or following tumor ablation. For example, prior to or during RF ablation, an electrolyte solution may be injected into the tumor, to enhance the conductivity of the tumor during the applying of RF current to the electrode(s). Alternatively, or in addition, the injected liquid may be a polymer liquid injected into the tumor or tumor region before, during, or following the activating (heating) step, depending on temperature conditions needed to promote hardening of the polymer once injected into the tumor site.

In still another aspect, the invention includes a method of injecting into an internal body site in a subject, a polymer liquid designed to harden at the body site. The polymer hardening may be due to heat-induced or promoted polymerization, e.g., cross-linking at the site, or the hardening of a thermoplastic polymer below its glass transition temperature. The method includes first positioning against or adjacent the internal body site, the distal end of an instrument having a distal-end electrode needle which can be activated to produce localized heating. With the tip so positioned, liquid polymer is injected through an electrode needle, either before, during, or following activation of the needle, such that the needle and surrounding tumor region is at a temperature that allows introduction of the polymer solution through the needle and hardening at the site of injection. In a preferred embodiment, the polymer liquid is polymethylmethacrylate, and the activating step is effective to maintain the temperature of the polymer liquid above its glass transition temperature while the liquid is being injected into the tumor.

In still another aspect, the invention includes a method of injecting a polymer liquid into an internal body site in a subject to form a solidified or hardened polymer plug at the site. The method includes positioning against or adjacent the internal body site, the distal end of an instrument having a distal-end electrode needle which can be activated to produce localized heating. With the needle so positioned, it is activated under heating conditions. The polymer liquid is then injected into the tumor, before, during or following the activating step, such that the needle and surrounding tumor region is at a temperature that allows introduction of the polymer solution through the needle and hardening at the site of injection.

For use in palliatively treating a pain-causing bone tumor, the needle is positioned within the tumor, the activating step is effective to ablate tumor tissue by heating, and the polymer liquid, when it hardens at the injection site, is effective to stabilize movement the ablated tumor region. In one preferred embodiment, the polymer liquid is a polymethylmethacrylate. The injecting step may include injecting the liquid through an electrode needle, and the activating step is effective to maintain the temperature of the polymer liquid above its glass transition temperature while the liquid is being injected through the needle.

These and other objects and features of the invention will become more fully apparent when the following detailed description of the invention is read in conjunction with the accompanying figures.

BRIEF DESCRIPTION OF THE FIGURES

FIGS. 7A–7H show numerous electrode configurations of the treatment device of an embodiment.

FIG. 36 illustrates a table showing tumor type and treatment parameters for a patient treatment study involving methods and embodiments of the bone treatment apparatus.

DETAILED DESCRIPTION OF THE ILLUSTRATED EMBODIMENTS

Figure 1A:
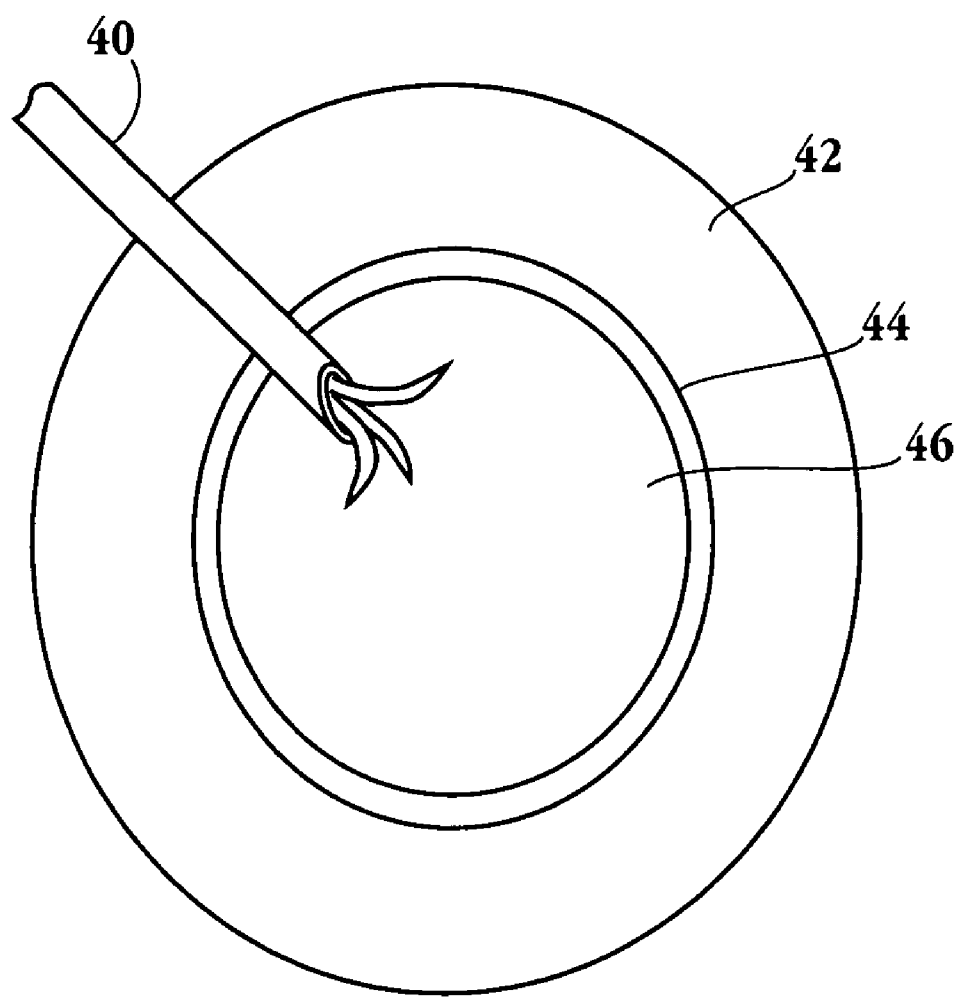
FIG. 1A shows placement and deployment of an apparatus to treat bone tumors, under an embodiment.

The present invention provides a method and system for palliatively treating a pain-causing bone tumor that may reside (i) on the exterior of compact bone region, below the bone periosteum, (ii) at least partially within the compact bone region, or (iii) within a medullary or cancellous region of the bone. More generally, the method and system, of the invention are designed for reducing the size and/or pain of bone tumors and lesions such as osteoid osteomas, metastatic carcinomas or myelomas by delivering sufficient energy to both ablate at least a portion of the tumor and/or to denervate nervous tissue associated with the tumor, e.g., the periosteum sheath covering an affected bone.

Embodiments of the invention also provide a method of treating these and other bone tumors while significantly reducing the complications and morbidity associated with surgical treatments including bone fracture and infection. Other bone disease, pathologies and associated lesions treatable by embodiments of the invention include, but are not limited to, osteosarcoma, ossifying fibroma, and fibrous dysplasia.

The following description provides specific details for an understanding of, and enabling description for, embodiments of the bone treatment device. However, one skilled in the art will understand that the invention may be practiced without these details. In other instances, well-known structures and functions have not been shown or described in detail to avoid unnecessarily obscuring the description of the embodiments of the invention.

I. Definitions

The following terms have the meanings given, unless otherwise indicated in the specification.

"Bone" refers to both flat bones, such as skull bones, scapula, mandible, and ileum, and long-bones, such as tibia, femur and humerus.

"Bone tumor" refers to a primary or metastatic tumor associated with bone, that is, a tumor on or in a bone.

A "tumor on or in a bone" refers, without limitation, to a tumor located (i) on the exterior of compact bone, below the bone periosteum, (ii) at least partially within compact bone, (iii) on the interior of compact bone, (iv) in a medullary or cancellous region of the bone, or (v) in a region near a bone, but having cell characteristics of known types of tumors associated with bone. Compact bone region" or "bone cortex," refers to the external part of bones formed by a dense, and typically thick layer of calcified tissue. In the cylindrical tube region (epiphyses) of a long bone, the cortex encloses the medullary cavity where bone marrow is stored. Toward the ends of the bones, the cortex becomes thinner and the internal space is filled with a network of thin, calcified trabeculae, called cancellous bone.

"Palliatively treating" a bone tumor means to treat the tumor in a manner that palliates the pain and/or discomfort of tumor. It does not necessarily mean that the tumor itself has been treated in a manner that retards future tumor growth or complications, although the tumor ablation step of the method may in fact retard or eliminate localized tumor growth.

"Distal end" with respect to an ablating instrument or introducer thereof, refers to the distal end or distal end region of the instrument or introducer thereof.

"Distal-end structure" or "distal-end tip" refers to the ablating structure, e.g., needle or electrode, carried at or deployable from the distal end of an ablating instrument or introducer thereof.

"Activating" or "activation", in the context of activating a distal-end structure, e.g., electrode, refers to the application of a stimulus to the tip or electrode that is effective to ablate tumor tissue in contact with the tip or electrode. Such activation can include RF or microwave current applied to an electrode, current applied to a resistive heating element (tip or electrode), ultrasound-generating current applied to an ultrasound generator or sonicator tip, a cryogenic fluid circulated through a circulation pathway in a tip, or an ablative fluid, e.g., ethanol or high salt, ejected from the end of a needle tip.

"Polymer liquid" refers, without limitation to a flowable or fluid form of a polymer, including a thermoset polymer or a thermoplastic polymer. A "thermoset polymer" refers to a polymer that sets by cross-linking reactions that may be initiated or accelerated by the application of heat. Polymer setting or solidification is thus irreversible. A "thermoplastic polymer" is one like polymethylmethacrylate, that has a glass transition temperature at which the polymer converts (or is in the process of converting) reversible from a solid to a liquid form.

II. Ablation System

The ablation system of the invention generally includes an instrument or device having a distal-end structure adapted to be inserted into the bone tumor, where the structure is activatable to ablate tumor tissue, and connecting structure for connecting the distal-end structure to an activating device. In one general embodiment, the instrument is formed of a probe or other elongate accessing member having a distal-end which is placed against or adjacent the bone region of interest, and one or more deployable electrodes or other activatable wires or needles that can be deployed from the probe into or against the tumor, forming the distal-end structure when deployed. The electrodes, when deployed, typically have a selected geometric configuration, such as a planar, or volume-forming configuration designed to optically ablate tumor tissue when activated. The assembly, and particularly the ablating instrument of the invention will now be described with reference to the figures.

FIG. 1A shows placement and deployment of an instrument 40 in the setting of a bone tumor. The instrument is configured to be positioned at a bone tissue site 44 to treat or ablate a bone tumor or lesion 46. Tissue site 44 can be located in any location in various bones including but not limited to the vertebrae, femur, tibia, fibula, ilium, sacrum, ulna, humorous, tibia and can be located in the diaphysis or the metaphysis portions. The apparatus can be configured to treat a number of lesions and ostepathologies including but not limited to metastatic lesions, osteolytic lesions, osteoblastic lesions, tumors, fractures, infected site, inflamed sites and the like. Once positioned at target tissue site 44, apparatus 40 can be configured to treat and ablate tissue at that site as well as collect a tissue sample using a bone biopsy device described herein or known in the art.

Figure 1B:
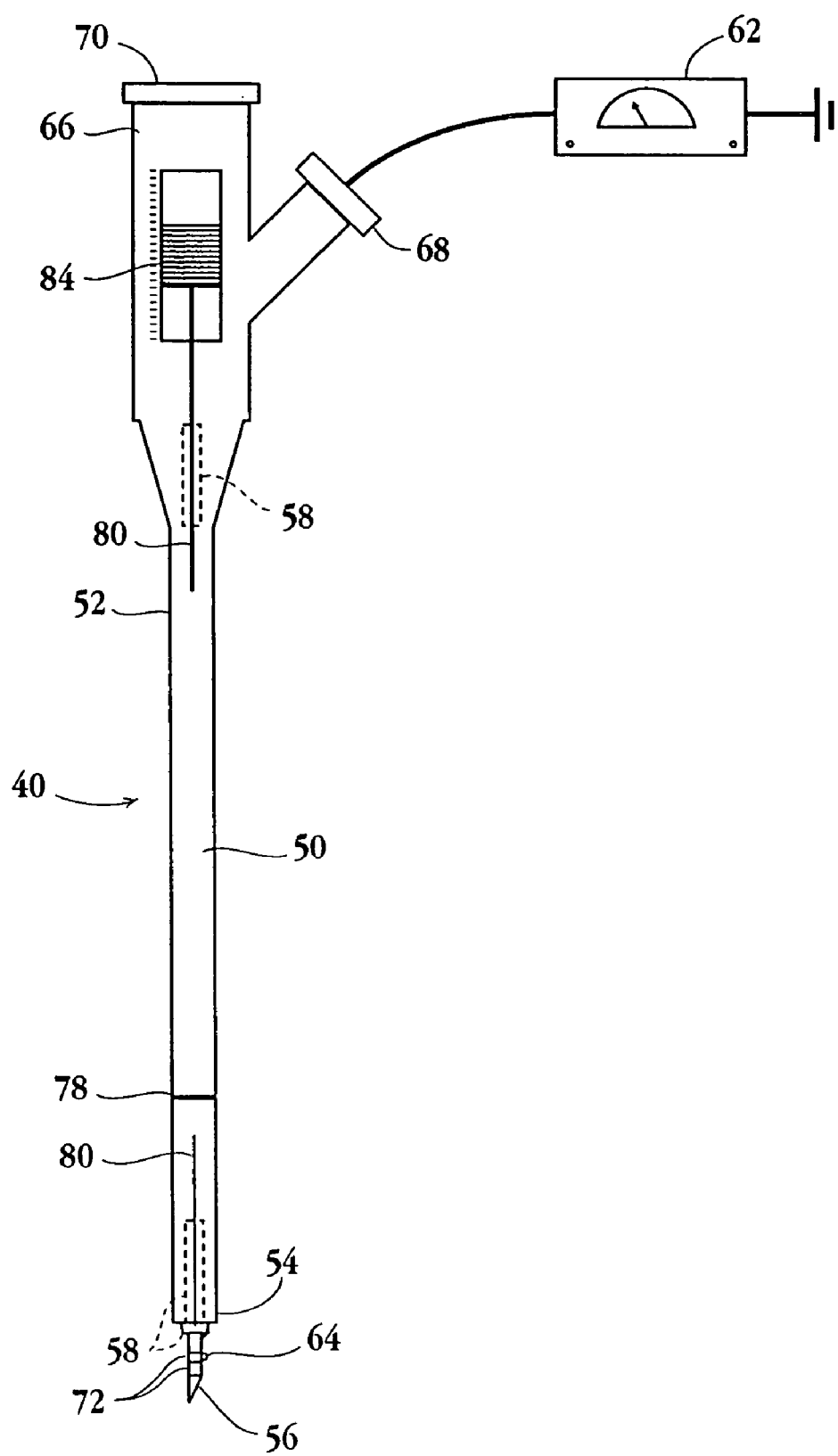
FIG. 1B shows an apparatus to treat bone tumors, under an embodiment.

FIG. 1B illustrates the instrument 40, and accompanying components of the assembly in greater detail. Instrument 40 includes an elongated shaft or probe 50 with a proximal end 52 and a distal end 54. Distal end 54 may be sufficiently sharp to penetrate tissue including bone, cartilage, muscle, and fibrous and/or encapsulated tumor masses. In the embodiment shown, distal end 54 is a needle 56 that is integral or otherwise coupled to probe 50. Probe 50 may have one or more lumens 58 that may extend over all or a portion of its length. An energy delivery device, generally denoted as 60, is coupled to distal end 54. Energy delivery device 60 can be configured to be coupled to an energy or power source 62. The connection is also referred to herein as connecting structure, and may include an fitting, coupling, or fastening suitable for fluid or energy input across or through the structure. A sensor 64 may be coupled to shaft 50 including distal end 54 and energy delivery device 60.

Figure 2:
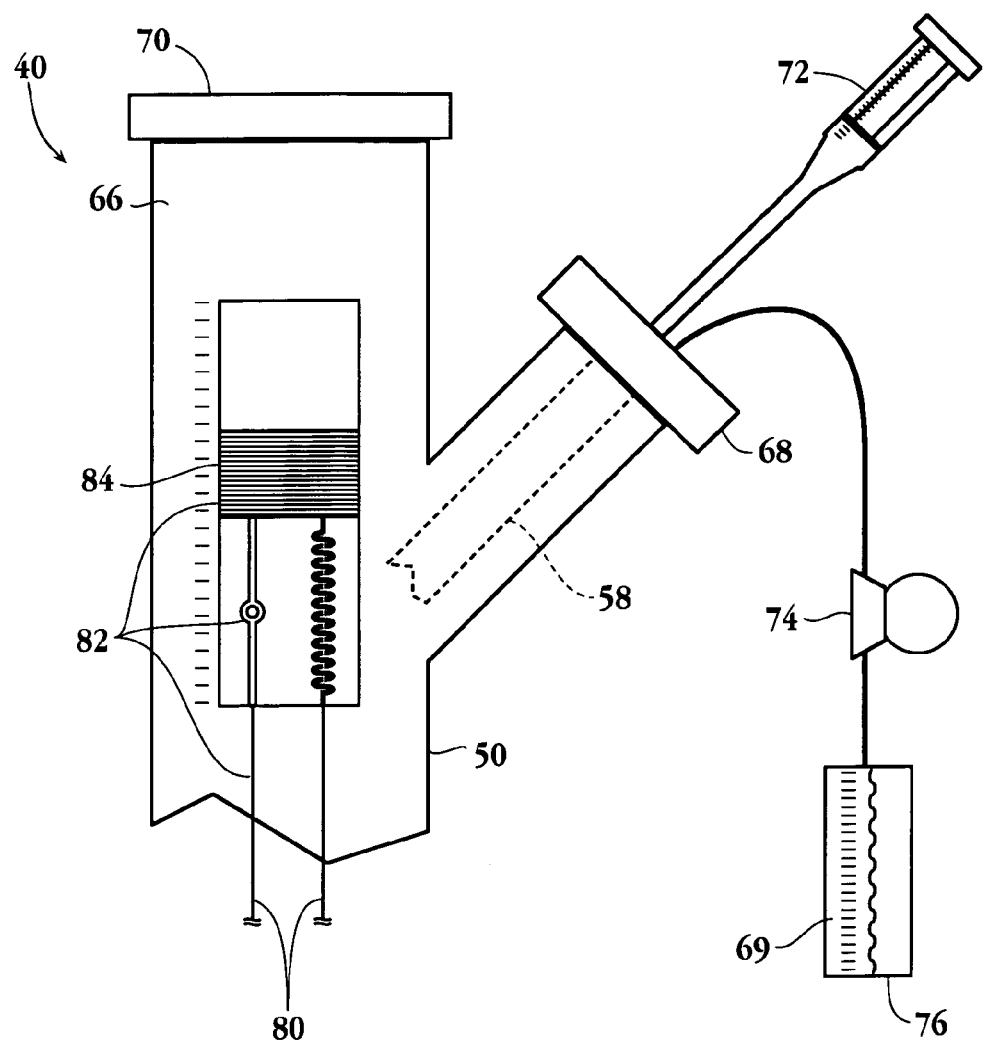
FIGS. 2 and 3 show an apparatus of an embodiment to treat bone tumors having a deflectable introducer.
Figure 3:
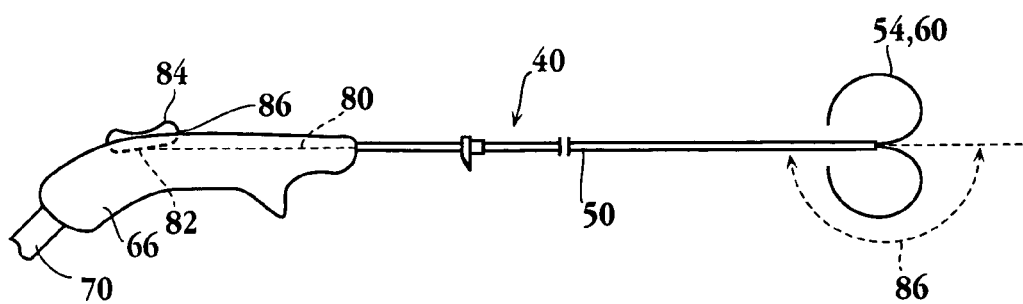

With reference to FIGS. 1, 2, and 3, introducer 50 can also be coupled at its proximal end 52 to a handle or handpiece 66. All or portions of handpiece 66 can be detachable and can include ports 68 and actuators 70. Ports 68 can be coupled to one or more lumens 58 and can include fluid and gas ports/connectors and electrical, optical connectors. At least one of these ports constitutes connecting structure for connecting a suitable liquid reservoir to the distal end tip of the instrument, e.g., a distal-end electrode needle. In various embodiments, ports 68 can be configured for aspiration (including the aspiration of tissue), and the delivery of cooling, conductivity enhancing, electrolytic, irrigation, polymer and other fluids 69 (both liquid and gas) described herein. Ports 68 can include but are not limited to luer fittings, valves (one-way, two-way), toughy-bourst connectors, swage fittings and other adaptors and medical fittings known in the art. Ports 68 can also include lemo-connectors, computer connectors (serial, parallel, DIN, etc) micro connectors and other electrical varieties well known to those skilled in the art. Further, ports 68 can include opto-electronic connections which allow optical and electronic coupling of optical fibers and/or viewing scopes (such as an orthoscope) to illuminating sources, eye pieces, video monitors and the like. Actuators 70 can include rocker switches, pivot bars, buttons, knobs, ratchets, cams, rack and pinion mechanisms, levers, slides and other mechanical actuators known in the art, all or portion of which can be indexed. These actuators can be configured to be mechanically, electro-mechanically, or optically coupled to pull wires, deflection mechanisms and the like allowing selective control and steering of introducer 50. Hand piece 66 can be coupled to tissue aspiration/collection devices 72, fluid delivery devices 74 (e.g. infusion pumps) fluid reservoirs (cooling, electrolytic, irrigation etc) 76 or power source 62 through the use of ports 68. Tissue aspiration/collection devices 72 can include syringes, vacuum sources coupled to a filter or collection chamber/bag. Fluid delivery device 74 can include medical infusion pumps, Harvard pumps, peristaltic pumps, syringes and the like.

In various embodiments, at least portions of bone treatment instrument 40 including introducer 50 and distal end 54 may be sufficiently radiopaque to be visible under fluoroscopy and the like and/or sufficiently echogenic to be visible using ultrasonography. In specific embodiments, introducer 50 can include radiopaque, magnopaque or echogenic markers 78, at selected locations including along all or portions of introducer 50 including distal end 54. Markers 78 can be disposed along introducer 50 to facilitate identification and location of tissue penetrating portion 54 including tissue collection portions, ports, sensors as well as other components and sections of bone treatment apparatus 40 described herein. In an embodiment, markers 78 can be ultrasound emitters known in the art. Also treatment apparatus 40 can include imaging capability including, but not limited to, fiber optics, viewing scopes such as a orthoscope, an expanded eyepiece, video imaging devices, ultrasound imaging devices and the like.

In various embodiments, instrument 40 can be configured to be percutaneously introduced into the bone through a trocar, bone biopsy device, or orthoscope or other orthopedic access device known in the art. For any of these devices, apparatus 40 can be introduced with the aid of a guidewire 80 which introducer 50 is configured to track over. Guidewire 80 can be any of a variety of flexible and/or steerable guide wires or hypotubes known in the art. Introducer 50 can have sufficient length to position distal tip 56 in any portion or lobe of the bone 42 using either a percutaneous or a bronchial/transoral approach. The length of introducer 50 can range from 5 to 180 cm with specific embodiments of 20, 40, 80, 100, 120 and 140 cm. The range of an embodiment is from approximately 25 to 60 cm. The length and other dimensional aspects of introducer 50 can also be configured for pediatric applications with a range in these embodiments of 15 to 40 cm. The diameter of introducer 56 can range from 0.020 to 0.5 inches with specific embodiments of 0.05, 0.1 and 0.3 inches as well as 1, 3, 6, 8 and 10 french sizes as is known in the art. Again, the diameter can be configured for pediatric applications with pediatric sizes of 1, 3 and 6 french. In various embodiments, the diameter of distal end 54 can range from 0.010 to 0.1 inches, with specific embodiments of 0.020, 0.030 and 0.040 inches. The diameter of distal end 54 can be configured to be positioned in individual bronchioles 8' such embodiment includes diameters of 0.40" or smaller.

In various embodiments, the introducer can be a catheter, multi-lumen catheter, or a wire-reinforced or metal-braided polymer shaft, port device (such as those made by the Heartport® Corp., Redwood City, Calif.), subcutaneous port or other medical introducing device known to those skilled in the art. In a specific embodiment the introducer is a trocar or a safety trocar and the like. Also as described herein the introducer can be adapted to be coupled to or used in conjunction with various orthopedic devices including but not limited to bone drills, bone chisels, bone dialators, orthoscopes and the like. The introducer can be constructed of a variety of metal grade metals known in the art including stainless steel such as 304 or 304V stainless steel as well shape memory metal such as Nitinol. The introducer can also be constructed from rigid polymers such as polycarbonate or ABS or resilient polymers including Pebax®, polyurethane, silicones HDPE, LDPE, polyesters and combinations thereof.

In various embodiments, the introducer can be rigid, semi-rigid, flexible, articulated and steerable and can contain fiber optics (including illumination and imaging fibers), fluid and gas paths, and sensor and electronic cabling. In an embodiment introducer is sufficiently rigid (e.g. has sufficient column strength) to pierce tissue including bone tissue without significant deflection along it longitudinal axis so as to maintain a longitudinal or other position within a tissue site. In another embodiment, all or portions (e.g. the distal portion) of the introducer are sufficiently flexible to pierce tissue, and move in any desired direction through tissue to a desired tissue site. In yet another embodiment, the introducer is sufficiently flexible to reverse its direction of travel and move in direction back upon itself.

Referring to FIGS. 2 and 3, all or portions of introducer 50 can be configured to be deflectable and/or steerable using deflection mechanisms 82 which can include pull wires, ratchets, latch and lock mechanisms, piezoelectric materials and other deflection means known in the art. Deflection mechanism 82 can be coupled to or integral with a moveable or slidable actuator 84 on handpiece 66. Mechanism 82 and coupled actuator 84 are configured to allow the physician to selectively control the amount of deflection 86 of distal tip 54 or other portion of introducer 50. Actuator 84 can be configured to both rotate and deflect distal tip 54 by a combination of rotation and longitudinal movement of the actuator. In an embodiment, deflection mechanism 82 comprises a pull wire 80 coupled to an actuator 84 on handpiece 66 described herein.

The amount of deflection of the introducer is selectable and can be configured to allow the maneuvering of the introducer through very tortuous anatomy and negotiate both obtuse or oblique turns in around various orthopedic and anatomical structures including the ribs and spine. In specific embodiments, the distal portions of the introducer can be configured to deflect 0–180° or more in up to three axes to allow the tip of the introducer to have retrograde positioning capability. The deflection can be continuous or indexed to pre-determined amounts selectable on handpiece 66 using an indexed actuator 84.

Figure 4:
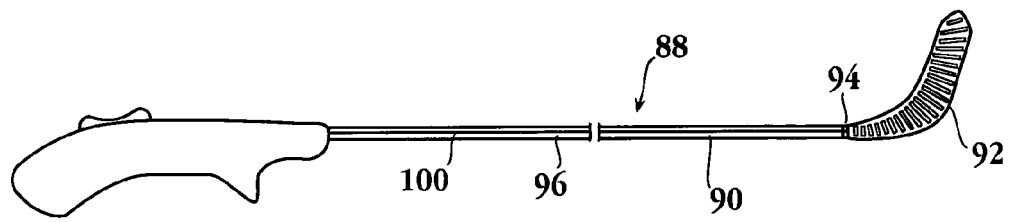
FIG. 4 illustrates an embodiment of a treatment apparatus having a deflectable portion at the distal end of the introducer.
Figure 5:
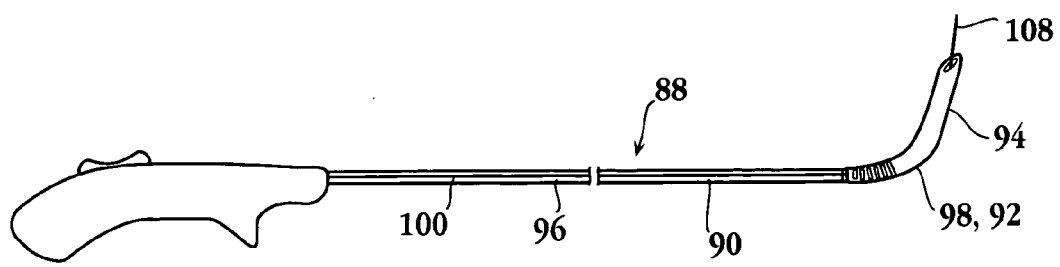
FIG. 5 illustrates an embodiment of a bone tumor treatment apparatus having an introducer with a hingedly attached deflectable portion.

FIG. 4 is an embodiment of a treatment apparatus having a deflectable portion at the distal end of the introducer. FIG. 5 is an embodiment of a bone tumor treatment apparatus having an introducer with a rotatably or hingedly attached deflectable portion. In an embodiment, introducer 90 has a deflectable or articulated section 92 at or near its distal portion 94. Deflectable portion 92 can be formed by use of corrugated or flexible materials (e.g. materials having a lower durometer than the adjoining less flexible section of the introducer) crimping, sectioning, molding, or other polymer metal working or catheter processing methods known in the art. Deflectable portion 92 can be deflected using various devices including pull wires, ratchet mechanisms, can mechanisms, and gear mechanisms (including a rack and pinion or worm gear mechanism) coupled to a pull wire or a stiffening mandrel which is advanced and withdrawn through lumen 96. Deflectable portion 92 can also be hingedly or pivotally attached to introducer 90 using a hinge mechanism which comprise one or more hinged sections 98 actuated by a pull wire or stiffening mandrel 100. Sections 98 can be mechanically coupled to introducer 90 and each other using one or more hinged or pivot joints known in the art.

Figure 6A:
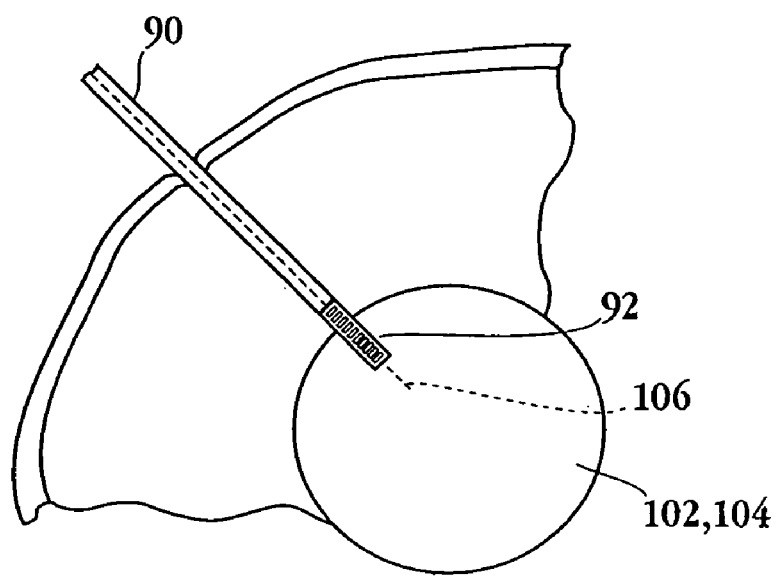
FIGS. 6A and 6B show use of the treatment device with a deflectable introducer, under the embodiments of FIGS. 4 and 5.
Figure 6B:
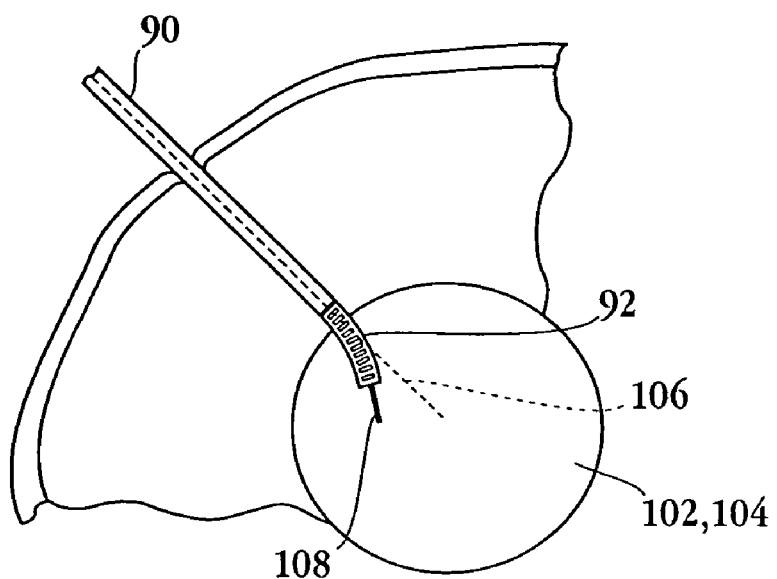

FIGS. 6A and 6B show use of the treatment device or instrument with a deflectable introducer, under the embodiments of FIGS. 4 and 5. In use, deflectable portion 92 allows the introducer to be introduced into tissue site 102 in a first fixed position (approximately straight with respect to a longitudinal axis 106 of the introducer) and then deflected a selectable amount to a second position in order to facilitate deployment of one or more energy delivery devices 108 into tumor mass 104 or tissue site 102. Further, deflectable portion 92 allows the energy delivery devices to be deployed at a selectable angle (including ranges from acute to oblique) with respect to the longitudinal axis 106 of the introducer. These capabilities can provide several results including (i) ensuring a more complete deployment of the energy delivery devices into the selected tumor mass; (ii) allowing faster deployment and withdrawal of the energy delivery devices reducing procedure time; (iii) allows the energy delivery device 108 to be positioned and deployed in irregularly shaped tumor masses (e.g. oblong, oval); (iv) allows the apparatus and energy delivery devices to be positioned and deployed in curved or otherwise difficult to reach portions of the anatomy including the orthopedic anatomy; and (v) allows the apparatus and energy delivery devices to be deployed at tumor site near or adjacent a delicate or sensitive anatomical structure(e.g. the spinal cord, artery) with a reduced or otherwise inappreciable risk of injuring that structure). In alternative embodiments, deflectable portion 92 can also be used to direct the delivery of an infusion fluid (including a jet or stream of fluid) described herein to a selectable portion of the tissue site 102 or tumor mass 104.

In another embodiment introducer 90 can include side ports which allow electrodes 108 to be deployed at a selectable angle with respect to the longitudinal axis 106 of introducer 90, including about 45 and 90 degrees. The use of such side ports is described in U.S. Pat. No. 5,683,384.

A variety of activation devices, including energy-delivery devices such as power sources, can be utilized by embodiments of the invention. Specific energy delivery devices 108 and power sources 110 that can be employed in one or more embodiments include, but are not limited to, the following: (i) a microwave power source adapted to be coupled to a microwave antenna distal end tip, providing microwave energy in the frequency range from about 915 MHz to about 2.45 GHz (ii) a radio-frequency (RF) power source adapted to be coupled to a distal end electrode, (iii) a coherent light source adapted to be coupled to an optical fiber or light pipe distal end tip, (iv) an incoherent light source adapted to be coupled to an optical fiber, (v) a reservoir containing heated fluid adapted to be coupled to a catheter with a closed or at least partially open lumen configured to receive the heated fluid, (vi) a reservoir of a cooled fluid adapted to be coupled to a catheter with a closed or at least partially open lumen configured to receive the cooled fluid, e.g., a cryogenic fluid, (ix) a resistive heating source adapted to be coupled to a conductive wire distal-end structure, (x) an ultrasound power source adapted to be coupled to an ultrasound emitter tip, wherein the ultrasound power source produces ultrasound energy in the range of about 300 KHZ to about 3 GHz, and (xi) combinations thereof.

In one preferred embodiment, the energy delivery device 108 is coupled to an RF power supply that provides RF current to one or more RF electrodes 108 . For these and related embodiments, the RF power supply delivers electromagnetic energy in the range from 5 to 200 watts to the electrodes. The electrodes 108 are coupled to the energy source either directly to each electrode 108, or indirectly using a collet, sleeve, connector, cable and the like which couples one or more electrodes to the energy source. Delivered energies can be in the range of 1 to 100,000 joules, with embodiments having ranges of approximately 100 to 50000 joules, 100 to 5000 joules, and 100 to 1000 joules. Lower amounts of energy can be delivered for the ablation of smaller structures such as nerves and small tumors with higher amounts of energy for larger tumors. Also delivered energies can be modified (by virtue of the signal modulation and frequency) to ablate or coagulate blood vessels vascularizing the tumor. This provides for a higher degree of assurance ablation of the blood supply of the tumor.

Figure 8:
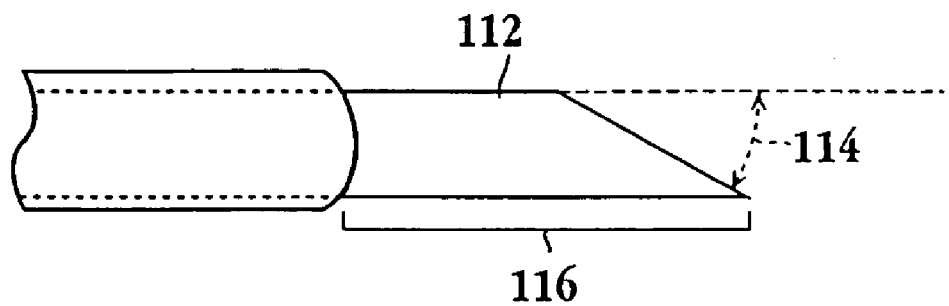
FIG. 8 illustrates an embodiment of a needle electrode configured to penetrate tissue.
Figure 9:
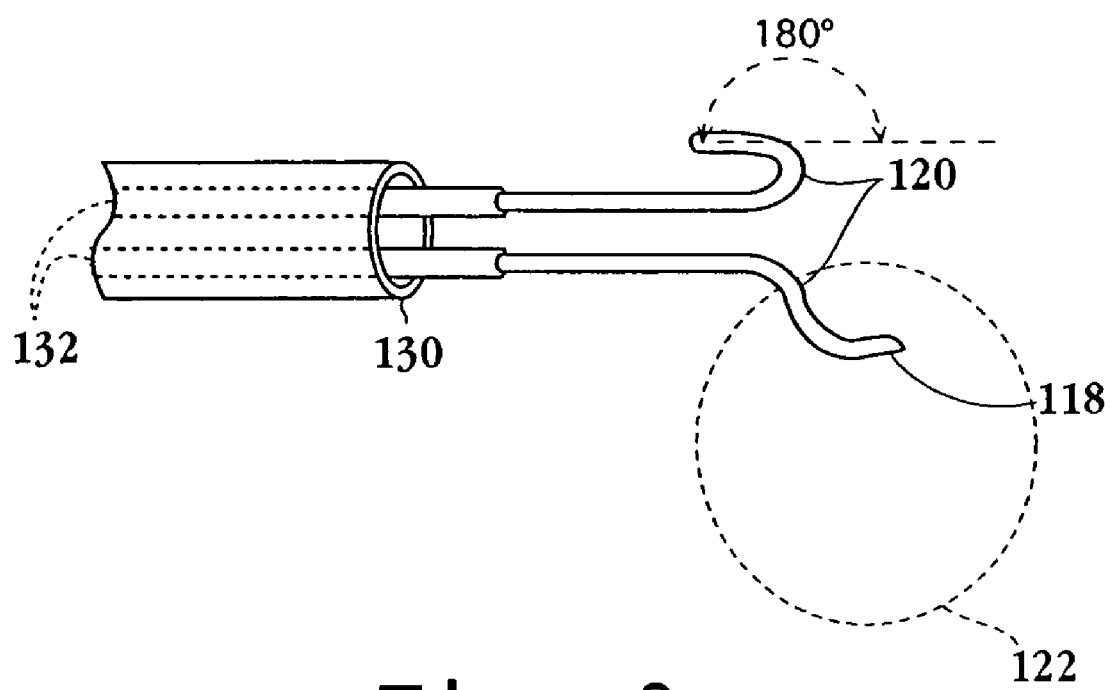
FIG. 9 shows a needle electrode having at least one radii of curvature.

FIGS. 7A–7H show numerous electrode configurations of the treatment device of an embodiment. FIG. 8 is an embodiment of a needle electrode configured to penetrate tissue. FIG. 9 shows a needle electrode having at least one radii of curvature.

FIGS. 7A–7H show the distal end region of various instruments, showing the distal end of an introducer 113A–113G and distal-end structure 112A–112H associated with the introducer. In FIGS. 7A–7C, the introducer and electrode are integral with one another, or in the case in FIG. 7A, the electrodes are formed as rings on the introducer. In FIGS. 7D∝7H, the electrode is deployable from the distal end of the introducer. FIGS. 7F and 7H show a needle electrode 112F and 112H, respectively, having injection ports, such as ports 115F, 115H, respectively, through which fluid material can be injected. FIGS. 7G and 7H illustrate an additional feature of a guidewire 117G, 117H, respectively used to position the introducer and/or electrode. As seen in FIG. 8, the distal end of the electrode 112 can have a cut angle 114 that ranges from approximately 1 to 60 degrees, with embodiments having angles of 25 and 30 degrees, respectively. The surface electrode 112 can be smooth or textured, and concave or convex. A conductive surface area 116 of electrode 112 can range from 0.05 mm$^2$ to 100 cm$^2$.

With reference to FIG. 9, and following, the instrument is composed of a probe or introducer with a distal end, and at least one electrode movable from a retracted position within the probe to a deployed position extending from the probe's distal end, forming the distal-end structure when deployed. The instrument may contain a plurality of curved, deployable electrodes, which, when deployed, create an array of deployed electrodes that defines a substantially two-dimensional surface expanse or a three-dimensional volume within the tumor. For example, for use in treating a bone tumor on the exterior or interior surface of a compact region of a bone, the electrodes, when deployed, may form an array that defines a two-dimensional expanse that is coextensive with a portion of the surface of the compact bone region surrounded by the tumor. As other examples, the deployed electrodes may form a three-dimensional volume that encompasses the instrument's distal tip, or three-dimensional volume that converges at the distal tip. The curvature of one or more of the electrodes may be shapable, prior to use, such that the electrode(s), when inserted into the tumor, define a selected geometry within the tumor. Various of these embodiment are described below.

In the embodiment in FIG. 9, electrode 118 can also be configured to be flexible and or deflectable having one or more radii of curvature 120 which can exceed 180° of curvature. In use, electrode 118 can be configured and positioned to heat, necrose or ablate any selected target tissue volume 122.

Electrode 118 can have different lengths that are advanced from distal end 130 of introducer 132. The lengths can be determined by the actual physical length of electrode(s) 118, the length of an energy delivery surface of electrode 118 and the length, of electrode 118 that is covered by an insulator 134. Suitable lengths include but are not limited to a range from 1–30 cms with specific embodiments of 0.5, 1, 3, 5, 10, 15 and 25.0 cm. The actual lengths of electrode 118 depends on the location of tissue site 122 to be ablated, its distance from the site, its accessibility as well as whether or not the physician chooses a bronchioscopic, percutaneous or other procedure.

In one general embodiment, the distal-end structure, e.g., one of a plurality of electrodes, is a needle forming a conduit through which liquid can be injected into the tumor, either prior to, during, or following tumor ablation. This embodiment includes additional connecting structure for connecting the needle to a source of liquid under pressure, as will be considered below.

Figure 10:
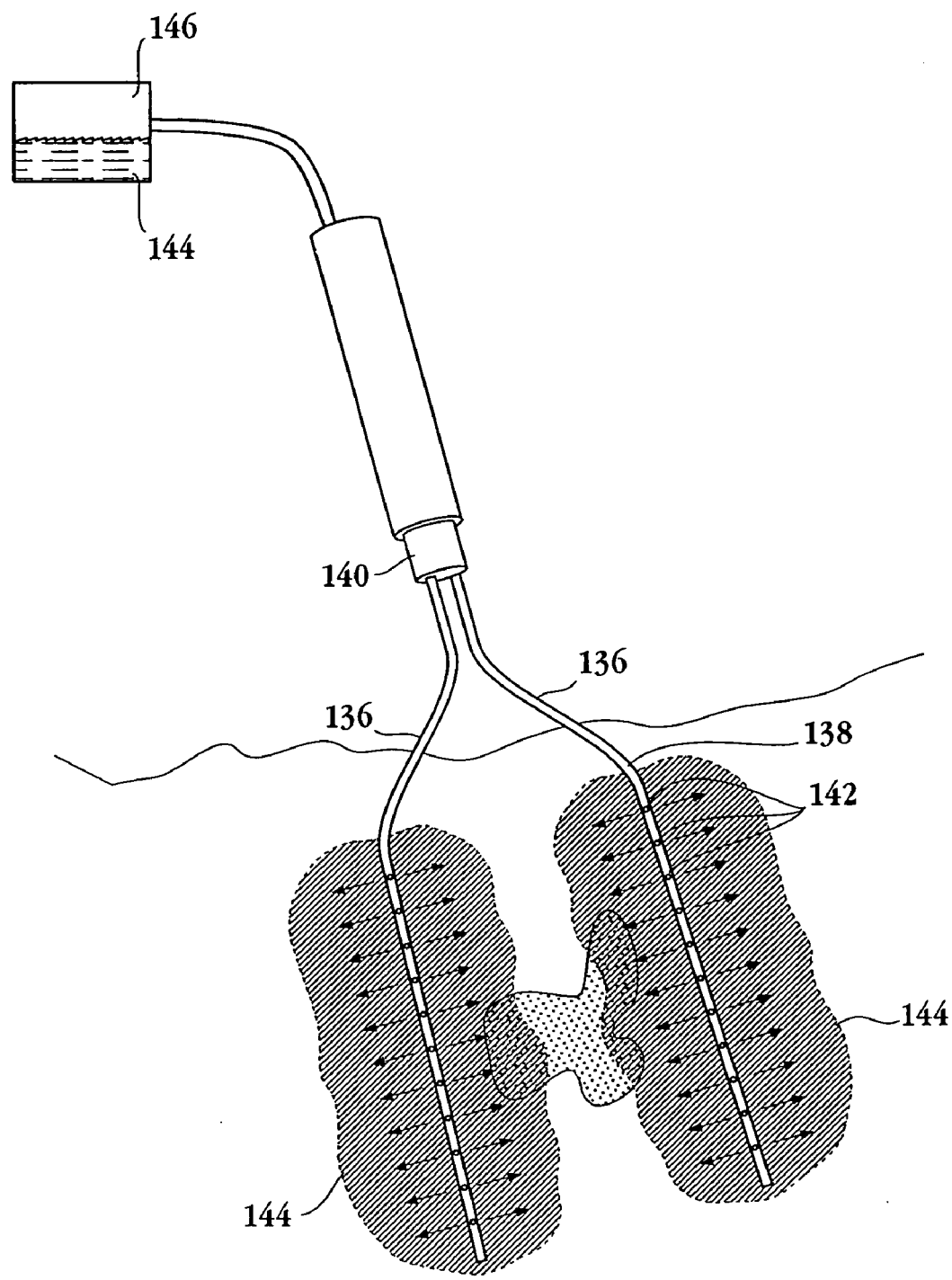
FIG. 10 shows an electrode of a treatment device that includes a lumen and apertures for the delivery of fluid, under an embodiment.

FIG. 10 shows an electrode of a treatment device that includes a lumen and apertures for the delivery of fluid, under an embodiment. Electrode 136 can include one or more lumens 138 (which can be contiguous with or the same as lumen 140) coupled to a plurality of fluid distribution ports 142 (which can be apertures 142) from which a variety of fluids 144 can be introduced, including conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media and combinations thereof. This is accomplished by having ports or apertures 142 that are fluidically coupled to one or more lumens 138 coupled to lumens 140 in turn coupled to fluid reservoir 146 and/or a fluid delivery device.

Figure 11:
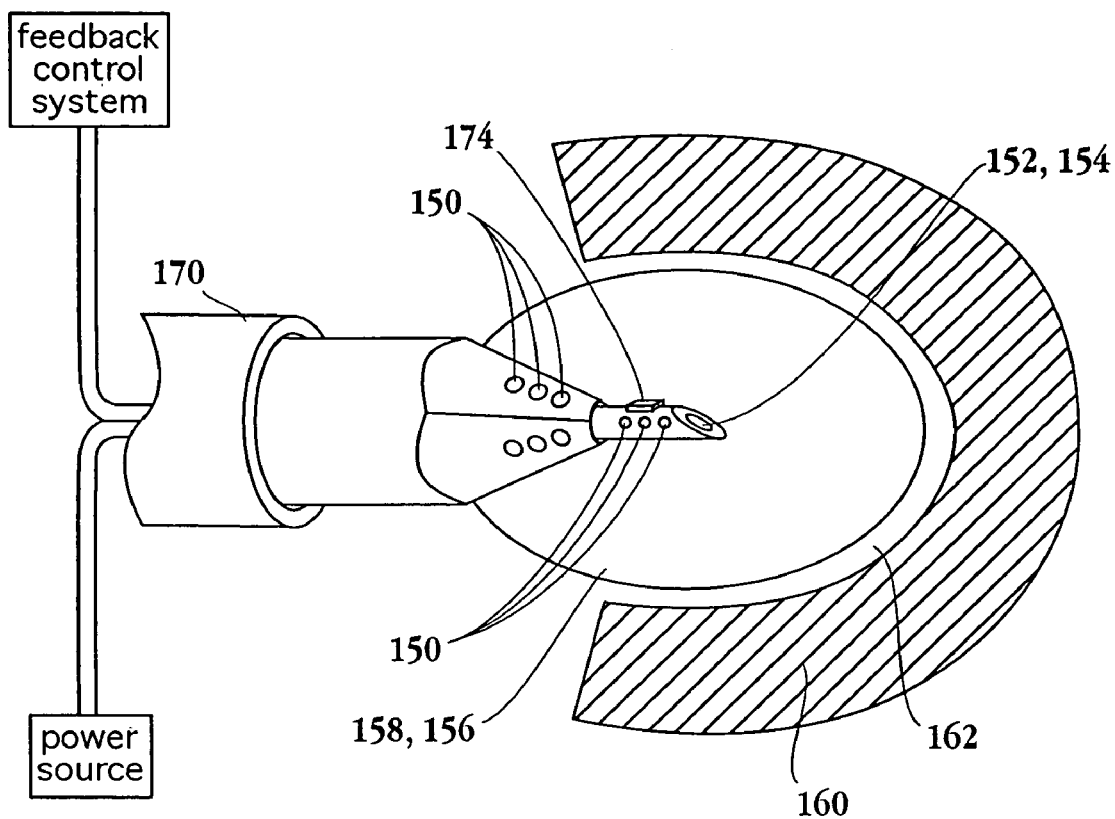
FIG. 11 shows an electrode with apertures for fluid delivery, under an alternative embodiment.

FIG. 11 is an electrode with apertures for fluid delivery, under an alternative embodiment. The apertures 150 can be configured to provide cooling of one or both of electrodes 152, 154 and surrounding tissue to prevent tissue from the development of excessive impedance at electrode 152 from the deposition of charred tissue on the surface of electrode 152. The cooling is accomplished by both the use of a cooled solution to cool the electrodes by a combination of convection and conduction. The amount of cooling can be controlled by control of one or more of the following parameters (i) temperature of the cooling solution (ii) flow rates of the cooling solution (iii) heat capacity (e.g. specific heat) of the cooling solution. Examples of cooling solutions include, water, saline solution and ethanol and combinations thereof. Other embodiments can utilize a cooling fluid or gas 156 which serves to cool electrodes 152 by ebullient cooling or Joule Thomson Effect cooling as well as the mechanisms described above. Embodiments utilizing Joule-Thomson Effect cooling can have a nozzle-shaped aperture 158 to provide for expansion of a cooling fluid 156. Examples of cooling fluid 156 include, but are not limited to, freon, $CO_2$, and liquid nitrogen.

In an embodiment, a conductivity enhancing solution or other solution 156 can be infused into target tissue site 160 including tissue mass 162. The solution can be infused before during or after the delivery of energy to the tissue site by the energy delivery device. The infusion of a conductivity enhancing solution 156 into the target tissue 160 creates an infused tissue area that has an increased electrical conductivity (verses uninfused tissue) so as to act as an enhanced electrode 152. During RF energy delivery the current densities in enhanced electrode 152 are greatly lowered allowing the delivery of greater amounts of RF power into electrode 152 and target tissue 160 without impedance failures.

In use, the infusion of the target tissue site with conductivity enhancing solution can provide two results: (i) faster ablation times; and (ii) the creation of larger lesions; both without impedance-related shut downs of the RF power supply. This is due to the fact that the conductivity enhancing solution reduces current densities and prevents desiccation of tissue adjacent the electrode that would otherwise result in increases in tissue impedance.

An example of a conductivity enhancing solution is a hypertonic saline solution. Other examples include halide salt solutions, and colloidal ferro solutions and colloidal silver solutions. The conductivity of enhanced electrode 152 can be increased by control of the rate and amount of infusion and the use of solutions with greater concentrations of electrolytes (e.g. saline) and hence greater conductivity. In various embodiments the use of conductivity enhancing solution 156 allows the delivery of up to 2000 Watts (W) of power into the tissue site impedance shut down, with specific embodiments of 50, 100, 150, 250, 500, 1000 and 1500 Watts achieved by varying the flow, amount and concentration of infusion solution 156. The infusion of solution 156 can be continuous, pulsed or combinations thereof and can be controlled by a feedback control system described herein. In a specific embodiment a bolus of infusion solution 156 is delivered prior to energy delivery followed by a continuous delivery initiated before or during energy delivery with energy delivery device 152 or other means. For embodiments of the invention relating to the treatment of bone tumors, infusion solution 156 can be delivered through the Haversian Canals as is described herein.

In various embodiments, the conductivity of the tumor mass 160 can be enhanced. This preferentially increases the rate and total amount of energy delivery to the tumor mass 160 relative to healthy tissue. This is achieved by infusing solution 156 directly into the tumor mass 160 through the use of a needle electrode 152 place within the tumor mass only. In related embodiments infusion solution 156 can be configured to remain or be preferentially absorbed or otherwise taken up by tumor mass 160. This can be achieved by controlling by one or more of the osmolality, viscosity and concentration of solution 156.

In one embodiment, described in Section III below, the liquid injected is a liquid polymer, such as a thermoset or thermoplastic polymer in liquid form, which is injected into the site in liquid form, where the material hardens or cures and forms a stabilizing polymer plug or coating near, on, or in the tumor.

The electrode 152 can be made of a variety of conductive materials, both metallic and non-metallic. Suitable materials for the electrode 152 include, steel such as 304 stainless steel of hypodermic quality, platinum, gold, silver and alloys and combinations thereof. Also, electrode 152 can be made of conductive solid or hollow straight wires of various shapes such as round, flat, triangular, rectangular, hexagonal, elliptical and the like. In a specific embodiment all or portions of electrodes 152 and 154 can be made of a shaped memory metal, such as NiTi, commercially available from Raychem Corporation, Menlo Park, Calif. A radiopaque marker can be coated on electrodes 152 for visualization purposes.

Electrode 152 can be coupled to introducer 170 or an advancement member using soldering, brazing, welding, crimping, adhesive bonding and other joining methods known in the medical device arts. Also, electrode 152 can include one or more coupled sensors 174 to measure temperature and impedance (both of the electrode and surrounding tissue), voltage and current other physical properties of the electrode and adjacent tissue. Sensors 174 can be at exterior surfaces of electrodes 152 at their distal ends or intermediate sections.

Figure 12A:
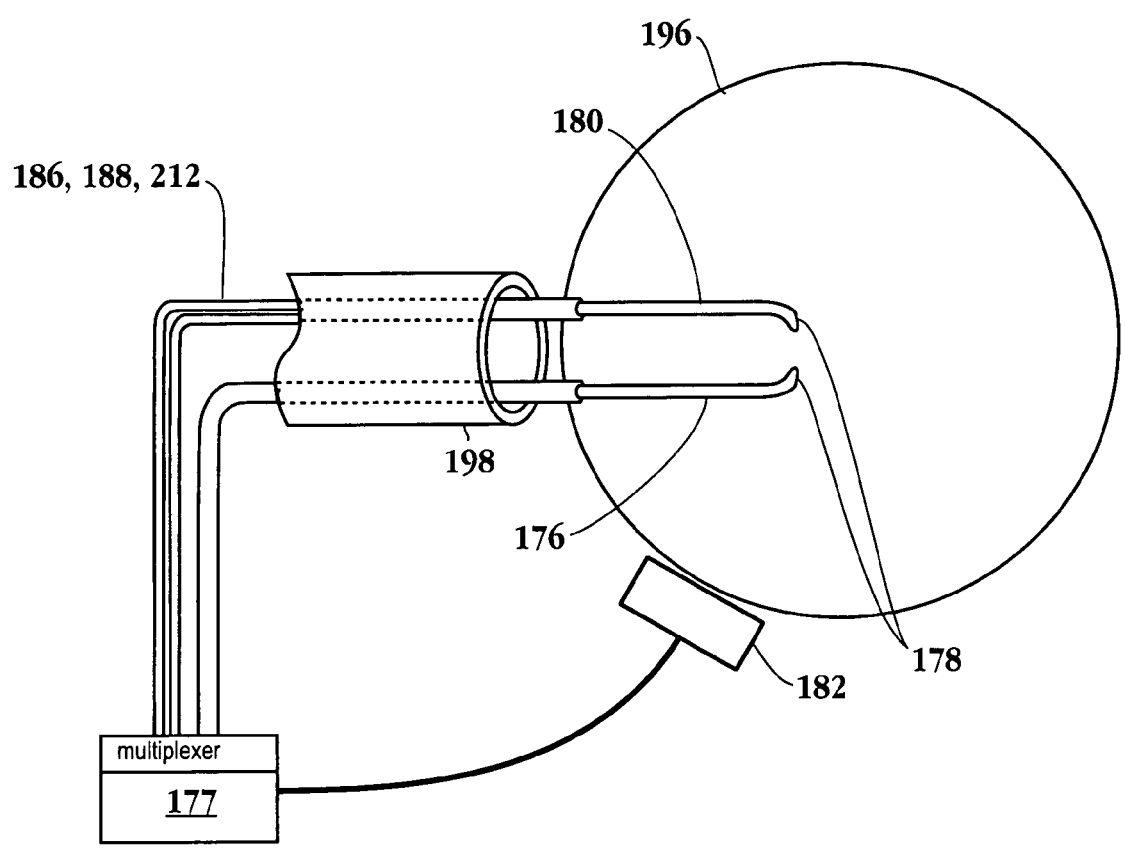
FIG. 12A shows a treatment device needle having multiple electrodes, under an embodiment.
Figure 12B:
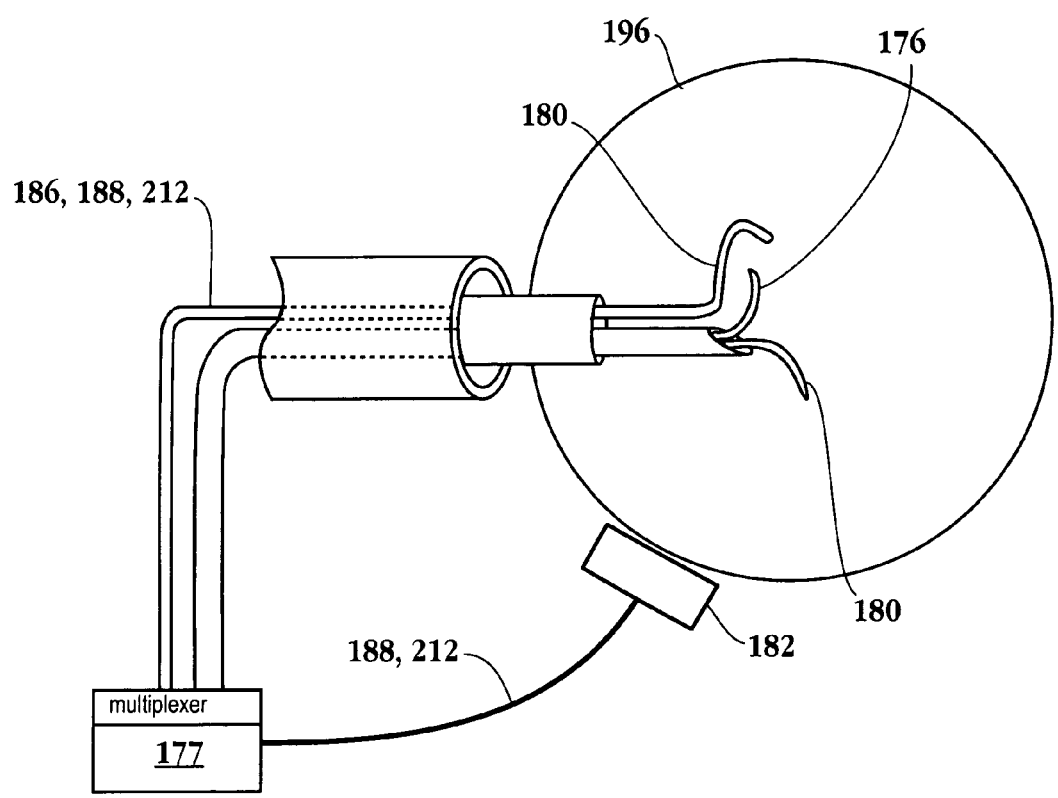
FIG. 12B shows a treatment device including electrodes coupled to two needles as well as a power supply and ground electrode, under an alternative embodiment.

In one general embodiment, the FIG. 12A is a treatment device needle having multiple electrodes, under an embodiment. FIG. 12B is a treatment device including electrodes coupled to two needles as well as a power supply 177 and ground electrode, under an alternative embodiment. Electrode 176 can comprise two or more electrodes 176 attached to an advancement member for bipolar electrode configurations and/or an array of electrodes 178 (either bipolar or monopolar). Electrodes 176 and 180 can be coupled to power supply 177 and/or ground pad electrode 182 via an insulated wire 188 which can be guidewire 180. The coupling can also be made via a coaxial cable, thereby allowing for coupling of one or both electrodes 176 and 180 to power supply 177 as a ground pad electrode 182. Wires 188 and 180 can also be coupled to a multiplexing device described herein. In use, electrodes 176 and 180 can configured and deployed to seal and/or treat (via ablative hyperthermia and/or ohmic heating) a selectable target tissue volume 196.

The selectable deployment of the electrode 176 is achieved through one or more of the following approaches: (i) the amount of advancement of electrode 176 from introducer 198; (ii) independent advancement of electrode 176 from introducer 198; (iii) the lengths and/or sizes of energy delivery surfaces of electrodes 176 and 180; (iv) variation in materials used for electrode 176; and (v) variation of the geometric configuration of electrode 176 in their deployed states.

Electrodes 176 and 180 can be configured to have compacted positions while they are positioned in introducer 198. As electrodes 176 and 180 are advanced from introducer 198 they move to a deployed state from their compacted configurations. Any number of electrodes can be included in energy delivery device 176. The electrodes of energy delivery device 176 can be deployed simultaneously, in pairs, in sets and one at a time. The deployable electrodes 176 are configurable to allow volumetric cell necrosis to proceed from the interior, exterior of tissue site 196 as well as various combinations thereof in order to create a selectable and predictable cell necrosis.

Electrodes 176 can also have sufficient column strength (compressive) and stiffness (flexural) to penetrate harder tissue masses including bone tumor tissue masses or tissue containing bone. The compressive column strength of electrodes 176 can be in the range from 0.1 to 10 lbs with specific embodiments of 0.5, 1, 2.5, 5 and 7.5 lbs. The column strength and stiffness of electrodes 176 can be achieved through the selection of one or more of the following: electrode materials (e.g. high strength metals), materials treatments (work hardening, tempering, annealing, etc), thickness and shape (cross sectional profile). In an embodiment, at least a portion of electrodes 176 can be made from a high strength metal such as stainless steal including 304V stainless steal. In a another embodiment electrodes 176 can be fabricated to have an increased stiffness in their distal portions and/or deployed lengths. This can be accomplished through increased electrode thickness, or work hardening the distal electrode sections or a combination of both.

Electrodes 176 and 180 can be advanced via means of a separate advancement member positionable in introducer 198 (e.g. via lumens) and may be coupled to an actuator to allow for selectable and controlled advancement of electrode 176 out of introducer 198 and into a selected depth in target tissue site 196. In an embodiment, the advancement member can be a catheter having one or more lumens for advancement of wires 186, 188 and 212 and electrodes 176 as well as for the introduction and infusion of fluids including electrolytic solutions, chemotherapeutic agents, drugs, medicaments, gene therapy agents, contrast agents and the like. In another embodiment, the advancement member can be a hypotube.

A deployable member can be coupled to electrode advancement member. Deployable member can be configured to provide a variety of different functions including but not limited to the placement of a sensor at a selected tissue site to measure/monitor temperature and/or impedance. Additionally, all or a portion, of deployable member can be an RF electrode operable in either bi-polar or mono-polar modes. Deployable member can also be a groundpad electrode. A sensor can be coupled to deployable member at a distal end, or at any physical location of deployable member. In this manner, temperature and/or impedance is measured or monitored at a distal portion of tissue site 196 or at any position in or external to tissue site 196.

Electrodes 176 and 180 can be selectably deployable from introducer 198 or deployable member with curvature to create any desired geometric area of cell necrosis. The selectable deployment is achieved by having electrodes 176 with, (i) different advancement lengths from introducer 198, (ii) different deployed geometric configurations, (iii) variations in cross-sectional geometries, (iv) selectable insulation provided at each and/or all of the deployed electrodes 176, or (v) the use of adjustable insulation. Deployed electrodes 176 and/or 180 can create a variety of different geometric cell necrosis zones including but not limited to spherical, semi-spherical, spheroid, triangular, semi-triangular, square, semi-square, rectangular, semi-rectangular, conical, semi-conical, quadrilateral, semi-quadrilateral, rhomboidal, semi-rhomboidal, trapezoidal, semi-trapezoidal, combinations of the preceding, geometries with non-planar sections or sides, free-form and the like.

Figure 13A:
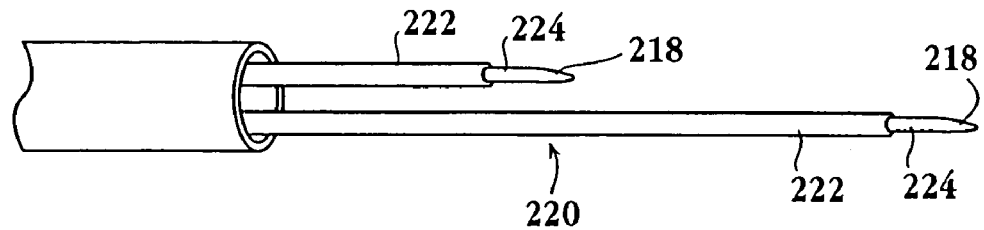
FIG. 13A illustrates a bone treatment device that includes insulation sleeves positioned at exterior surfaces of the electrodes.
Figure 13B:
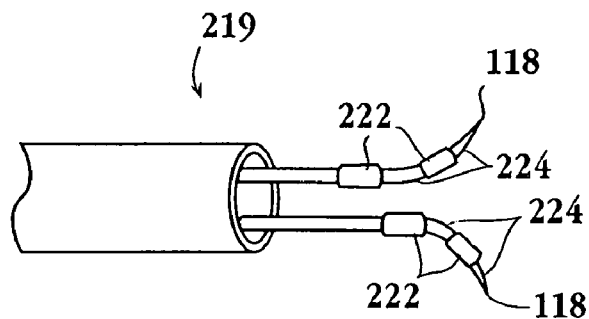
FIG. 13B illustrates a bone treatment apparatus including multiple insulation sleeves that circumferentially insulate sections of the electrodes, under an alternative embodiment.
Figure 13C:
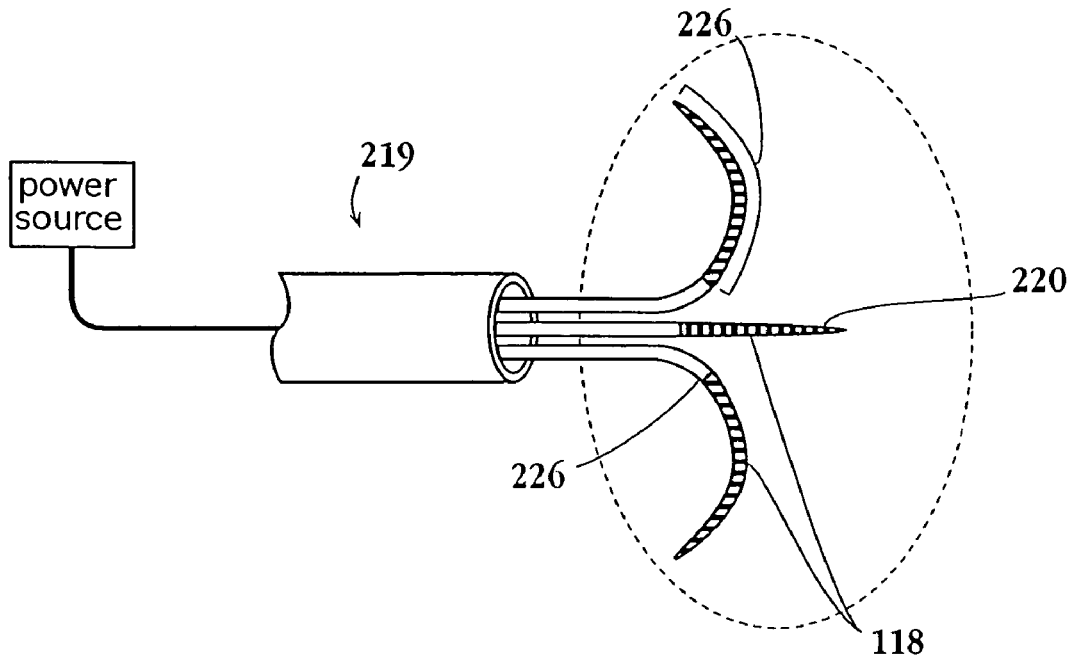
FIG. 13C illustrates a bone treatment device of another alternative embodiment that uses a nonstick coating on the electrodes.
Figure 14:
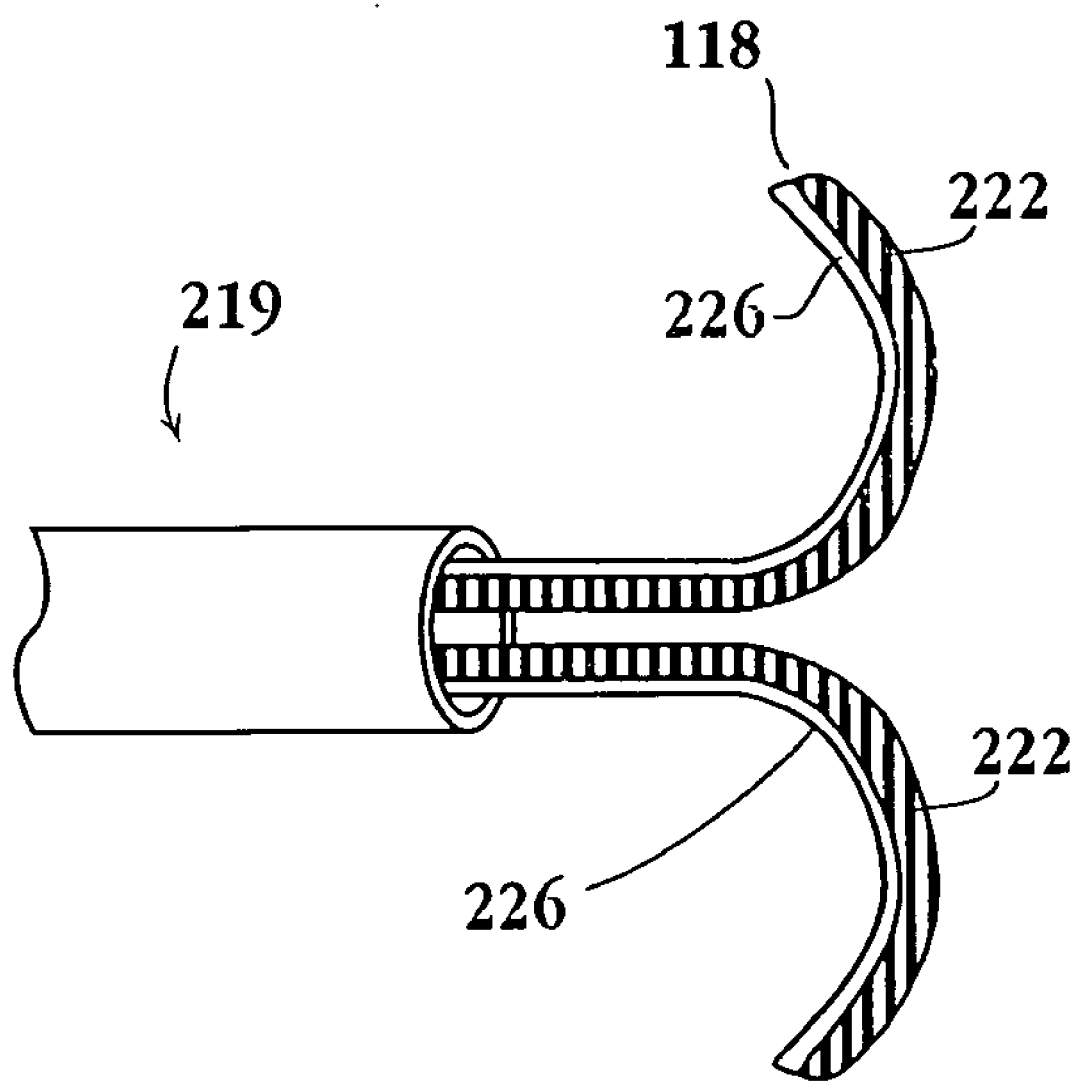
FIG. 14 shows a bone treatment apparatus including insulation that extends along longitudinal sections of electrodes to define adjacent longitudinal energy delivery surfaces, under an embodiment.

FIG. 13A is a bone treatment instrument 219 that includes insulation sleeves positioned at exterior surfaces of the electrodes. FIG. 13B is a bone treatment apparatus including multiple insulation sleeves that insulate sections of the electrodes, under an alternative embodiment. FIG. 13C is a bone treatment device of another alternative embodiment that uses a nonstick coating on the electrodes. FIG. 14 is a bone treatment apparatus including insulation that extends along longitudinal sections of electrodes to define adjacent longitudinal energy delivery surfaces, under an embodiment. In these embodiments, one or more electrodes, as well as deployable member 220, can have an exterior surface that is wholly or partially insulated or coated and provide a non-insulated area which is an energy delivery surface. In the embodiment of FIG. 13A, electrodes 118 can include insulation 222. In this embodiment insulation 222 is an insulation sleeve 222 that can be fixed or adjustable. The active area of electrodes 118 is non-insulated and provides an energy delivery surface 224. In the embodiment of FIG. 13B insulation 222 is formed at the exterior of electrodes 118 in circumferential patterns, leaving a number of energy delivery surfaces 224 which can be ring shaped distributed over the length of electrode 118.

With reference to FIG. 13C, all or a portion of the energy delivery device 118 of an embodiment, including one or more RF electrodes or antennae, can be coated with a nonstick and/or hydrophobic coating 226 configured to eliminate or significantly reduce the adherence of charred or desiccated tissue to the energy delivery device resulting from tissue heating during the ablation process. Coatings 226 can include but are not limited to, polytetrafluorethylene, TEFLON, fluorinated ethylene propylene, perfluoroalkoxy and other fluoropolmers, paralene, polydimethysiloxanes (silicones) and polymers and combinations thereof. Such coating can be added via dipping, spraying, co-extrusion, vacuum deposition, vapor deposition; ion beam assisted deposition, diffusion, laser and plasma processes, chemical plating, grafting and other methods known in the art. The coating can be applied as a single coat or in multiple coats using primer coats wherein the coating are configured to have good intercoat adhesion. Further, coatings 226 can be applied evenly over the desire coated length of the energy delivery device 118 or can applied in a graduated fashion with the distal end of the electrode having an increased or decreased thickness with respect to a proximal portion of the electrode.

In various embodiment the coating thickness can range from 1 μm to 10000 μm with embodiments of 500, 1000, 3000 and 5000 μm. Further in various embodiments the coating thickness can vary by 1 μm to 3000 um over the length of the energy delivery device. In various embodiments, coating 226 can also be configured to have thermal and/or electrically insulative properties. In use, the non stick lubricousness of coating 226 can perform several functions including, but not limited to the following: (i) facilitating withdrawal of the energy delivery device post ablation into the introducer without resistance due to adhered tissue; (ii) allowing the apparatus to be rapidly repositioned in the same or different target tissue site; (iii) allowing the apparatus to be positioned and removed from smaller or more difficult to reach tissue sites such as the ribs, and/or smaller pediatric bones due; (iv) reducing the risk of emboli developing from dislodge charred tissue entering into the blood stream; and (v) reducing the risk of or subsequent tumors or metastases developing from adherent malignant tissue contaminating healthy tissue upon removal or repositioning of the apparatus, energy delivery device or introducer.

With reference to FIG. 14, insulation 222 extends along a longitudinal exterior surface of electrodes 118. Insulation 222 can extend along a selected distance along a longitudinal length of electrodes 118 and around a selectable portion of a circumference of electrodes 118. In various embodiments, sections of electrodes 118 can have insulation 222 along selected longitudinal lengths of electrodes 118 as well as completely surround one or more circumferential sections of electrodes 118. Insulation 222 positioned at the exterior of electrodes 118 can be varied to define any desired shape, size and geometric energy delivery surface 224.

Figure 15:
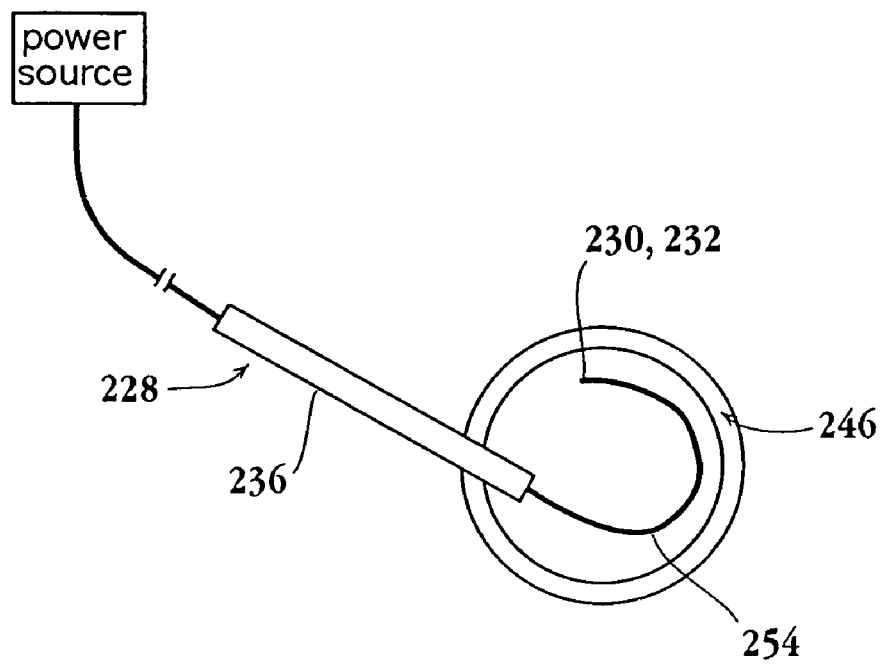
FIG. 15 shows an embodiment of a bone treatment apparatus having coiled electrodes.
Figure 16:
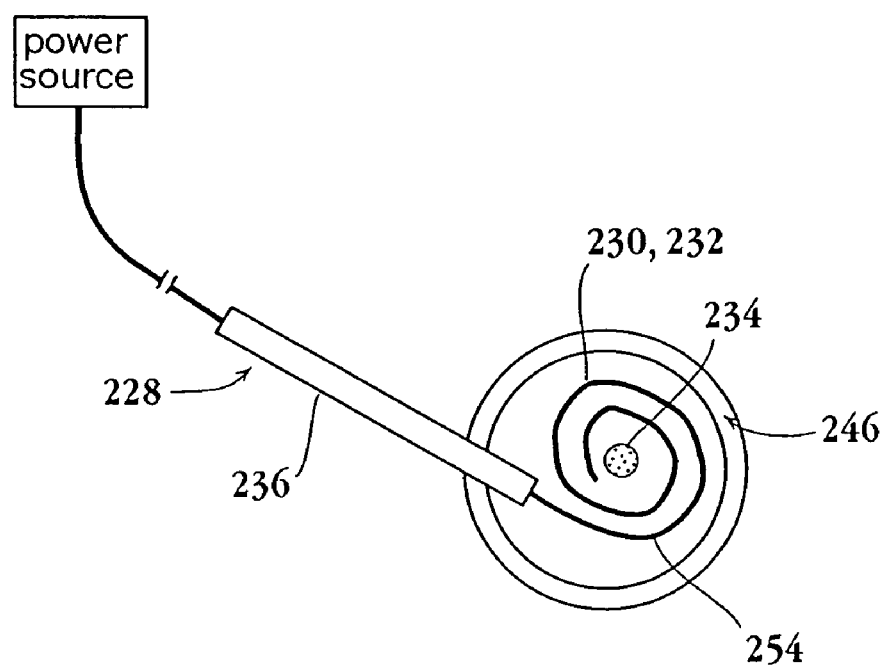
FIG. 16 illustrates a bone treatment apparatus having inwardly coiled electrodes, under an alternative embodiment.
Figure 17:
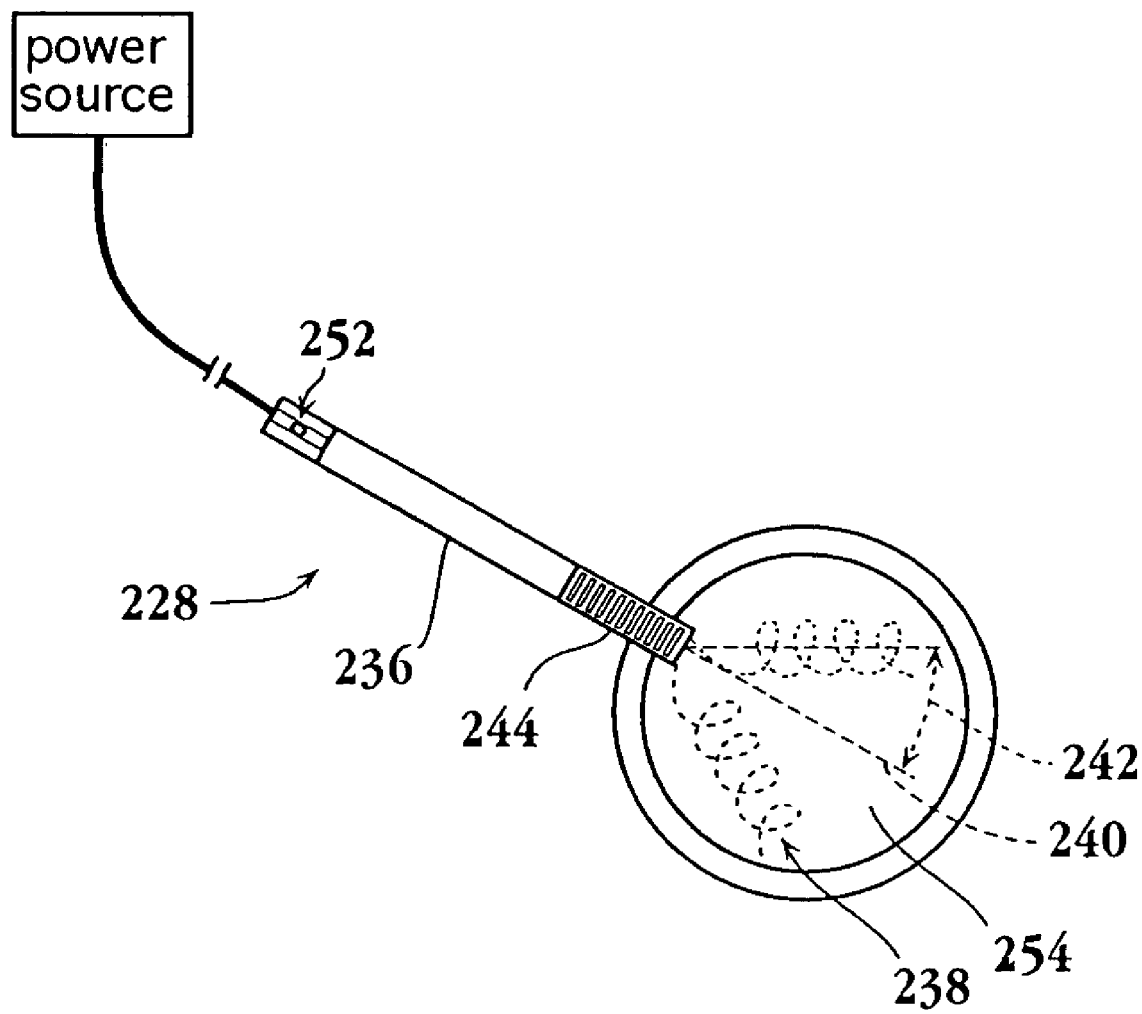
FIG. 17 shows a bone treatment device having helical electrodes, under another alternative embodiment.

FIG. 15 shows an embodiment of a bone treatment apparatus 228 having coiled electrodes. FIG. 16 is a bone treatment apparatus having inwardly coiled electrodes, under an alternative embodiment. FIG. 17 is a bone treatment device having helical electrodes, under another alternative embodiment. FIG. 18 shows the electrode of a bone treatment device curving in response to force applied by a bone-tumor interface, under an embodiment.

In the embodiment of FIG. 15, the energy delivery device 230 can comprise a flexible electrode that is preconditioned to assume a curled or coiled shape 232 as the electrode is advanced out of the introducer 236. In a related embodiment, shown in FIG. 16, electrode 230 can be configured to coil inwardly into the center of the tumor 234 as the electrode is advanced out of the introducer. In use, coiled electrode 232 provides a way for achieving a greater probability of necrosis or ablation of the entire tumor by delivering energy to both the perimeter and the center of the tumor. This result reduces the risk of tumor recurrence due to incomplete removal of the tumor.

Referring to FIG. 17, electrode can be fabricated to assume a helical shape 238. Helical electrode 238 has either a substantially constant radius or varying radius. The longitudinal axis 240 of the helix 238 can be in the same direction as that of the introducer axis 240 or can be perpendicular to this axis. The various embodiments, the angle of the helix 242 can be in the range of 0 to 90° with respect to introducer axis 240 with specific embodiments of 30, 45 and 60°. The angle of the helix can be controlled using a deflection mechanism 252 and/or introducer deflectable portion 244 described herein.

Figure 18A:
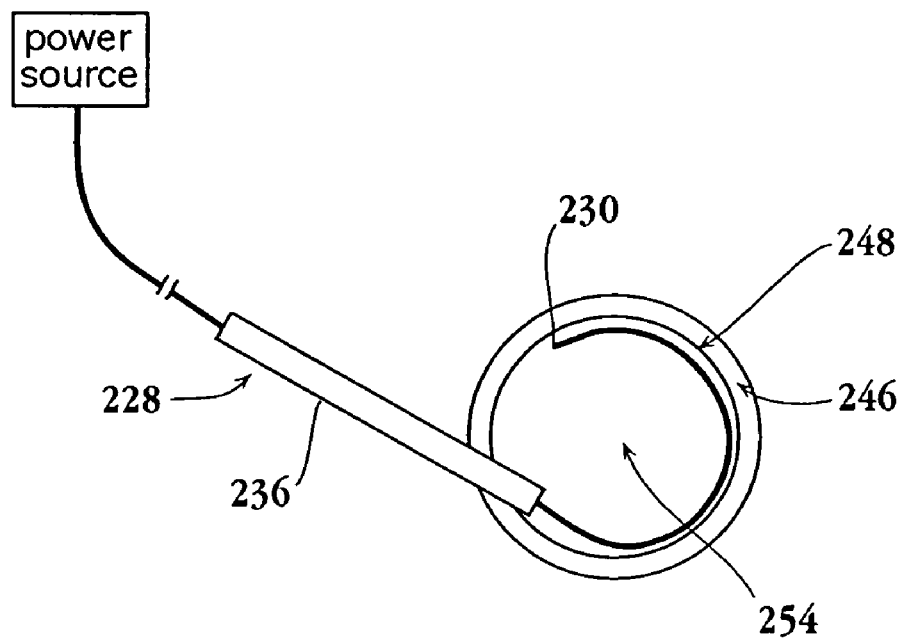
FIGS. 18A and 18B shows the electrode of a bone treatment device curving in response to force applied by a bone-tumor interface, under an embodiment.
Figure 18B:
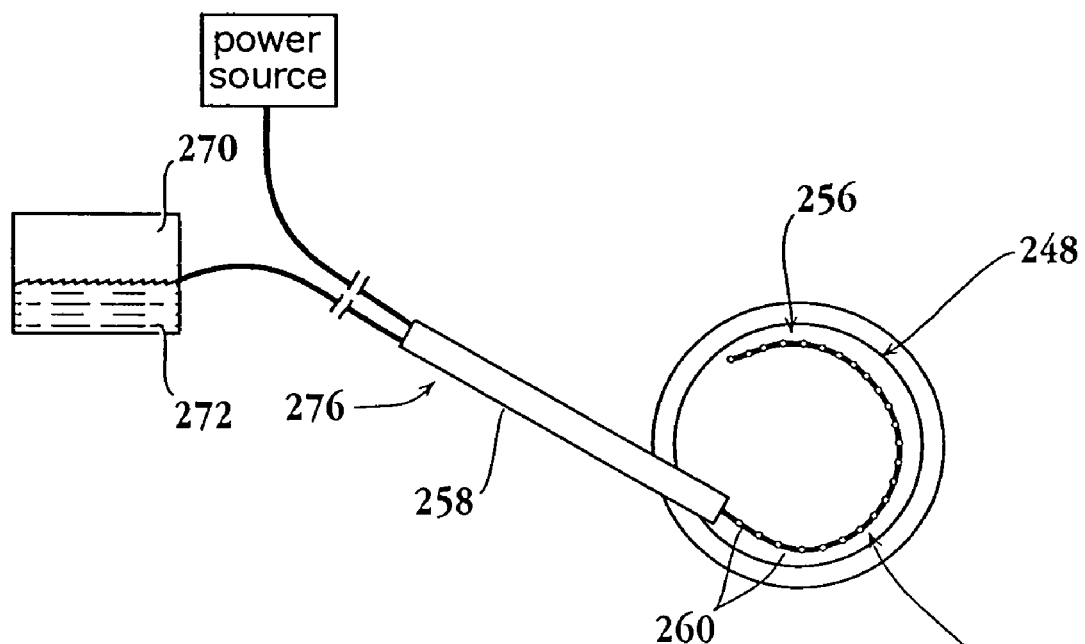

Referring to FIGS. 18A and 18B, electrode 230 can be configured to curve in response to a force exerted by the bone-tumor interface 246 to encircle (completely or partially) the perimeter of the tumor 248 one or more times. In various embodiments, this can be achieved through the selection of the material properties of the electrode including but not limited to elastic modulus, percent elongation, yield strength, column strength, diameter, bending modulus, spring constant, degree of tapering and the like. In an embodiment, this is achieved by selection of one or more parameters including bending modulus, wire diameter, and spring constant. A parameter is selected that provides the wire with sufficient flexibility so as to be bent by the bone-tumor interface 246 while providing sufficient spring force and column strength to continue to curve around the perimeter 248 of the tumor 234 with continued advancement out of the introducer 236.

In an embodiment, helical electrode 238 can be a helical coil spring with a selectable amount of spring force. In various embodiments, all or portions of helical electrode 238 can have a lateral spring force in the range of about 0.1 to about 10 lbs with specific embodiments of 0.5, 1, 2.5, 5 and 7.5 lbs. In an alternative embodiment electrode 238 can be in the shape of a substantially flat or compressed helical coil (in the longitudinal axis) that can be positioned against and deliver energy to the surface of a bone tumor and which can be expanded in the longitudinal axis to a deployed shape (using for example a pull wire coupled to an actuator, on the handpiece described herein) to penetrate the tumor a selectable amount.

In an alternative embodiment, the circular shape of the electrode 230 can be achieved by a deflection mechanism 252 described herein. In yet another embodiment, all or a portion of the distal section of the electrode is made of a shape memory material such as a Nickel titanium alloy which is preformed/pretreated to assume the desired circular or coiled shape using metallurgical methods described herein or known in the art. In an embodiment the transition temperature can be in the range of 30 to 60 degrees Celsius, with specific range embodiments of 37 to 55 degrees and 40 to 50 degrees Celsius, and specific embodiments of 35, 45, and 55 degrees Celsius. Heating to achieved this temperature can be achieved through the use of body temperature, or through the delivery of energy to or thorough the electrode or other energy delivery device. In various embodiments, the energy can be RF, microwave, resistive heating, ultrasound and the like.

In a specific embodiment, one or more electrodes 230 or other energy delivery devices are configured to assume a coil or helical shape 238 upon initial deployment into the tumor mass 254. Following deployment, the electrodes controllably increase in diameter with an increase in temperature via energy delivery from the electrode to a larger diameter and circle the perimeter of the tumor. This configuration allows for heating the tumor from the inside out; it also allows for heating the tumor in a more uniform fashion while reducing the risk or amount of desiccation or charring as the tissue becomes heated. Further, it allows for faster, larger and more uniform ablations particularly along the perimeter of the tumor. This occurs because the conductive path of energy into cooler of unablated tissue is reduced or constantly maintained verses having the energy have to be conducted through already heated tissue into cooler tissue. The reduced conductive path reduces tissue impedance enabling faster ablations and reducing the amount of tissue desiccation and charring.

The rate of diameter increase of the electrode radius can be selected to increase at rate matching in proportion or ratio to the increase in temperature of the surrounding tissue to a selected threshold temperature. In various embodiments this threshold temperature can be in the range of 37 to 70 degrees Celsius, with specific embodiments of 38, 40, 45, 50, 55, 60 and 65 degrees Celsius. In specific embodiments the temperature is selected to be sufficient to injure, ablate or necrose all or a portion of tumor mass 254. In alternative embodiments the degree of coil expansion can also be controlled through the use of a deflection mechanism described 252 herein which can be electromechanically coupled to a computer or microprocessor controlled servo mechanism known in the art and the like.

Figure 19A:
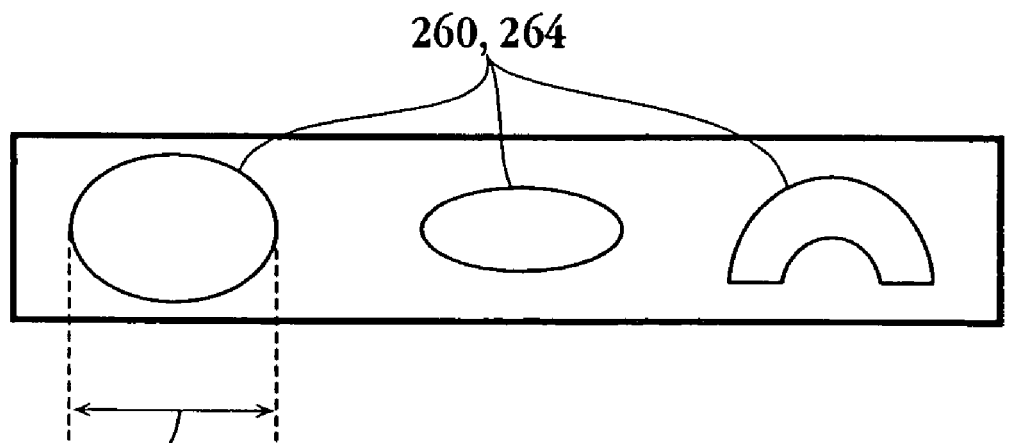
FIG. 19A illustrates an embodiment of a coiled electrode including fluid delivery apertures.
Figure 19B:
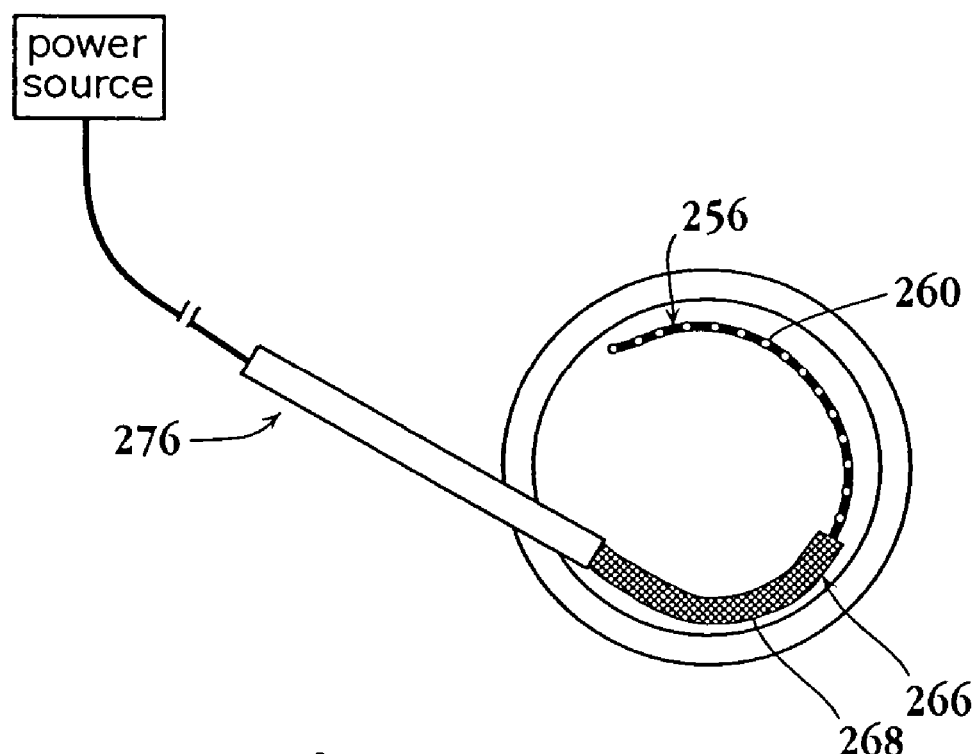
FIG. 19B illustrates a coiled electrode having fluid delivery apertures and a covering sheath, under an alternative embodiment.
Figure 19C:
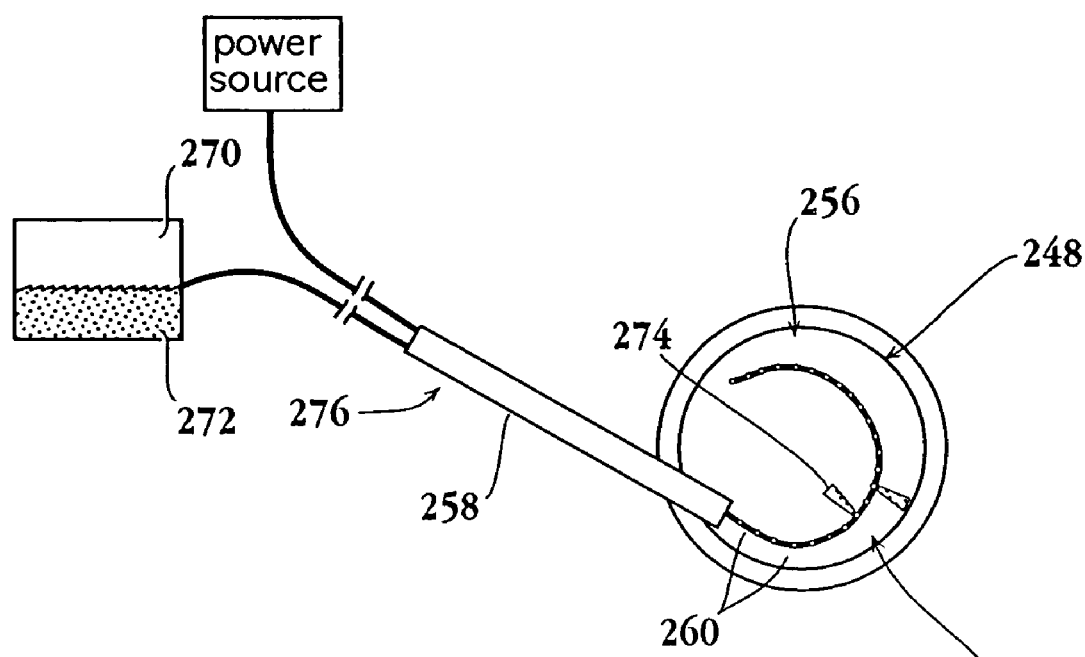
FIG. 19C shows a coiled electrode with fluid delivery apertures and a fluid jet, under another alternative embodiment.

FIG. 19A is an embodiment of a coiled electrode including fluid delivery apertures. FIG. 19B is a coiled electrode having fluid delivery apertures and a covering sheath, under an alternative embodiment. FIG. 19C shows a coiled electrode with fluid delivery apertures and a fluid jet, under another alternative embodiment. The coil or helical electrode 256 can have one or more fluid delivery lumens 258 through all or a portion of the coil. In these and related embodiments, all or a portion of the helix 256 can have a plurality of fluid delivery apertures 260 fluidically coupled to one or more of the fluid delivery lumens 258. The apertures 260 can be evenly distributed along the entire deployed length of the coil 256 or over a quartile, half (semicircular) or other selected arc portion of the helix or coil.

The apertures 260 can all have substantially the same diameter or varied diameters 262 distributed over a selectable portion of the helix 256. In various embodiments, the apertures 260 can have diameters 262 in the range of 0.001 to 0.25 inches with specific embodiments of 0.002, 0.005, 0.01, 05, and 0.1 inches. Further, apertures 260 can have a variety of shaped openings 264 including but not limited to circular, oval, semicircular, linear and rectangular.

In an embodiment, the apertures 260 are configured to have increasing diameters going in a distal direction with respect to electrode helix 256 so as to provide a substantially constant aperture ejection flow rate over the apertured portion of the helix by decreasing the fluid resistance moving in the distal direction according to Poiseuille's law (F=DP p r 4/8 h l). In a specific embodiment this is achieved by increasing the aperture diameter 262 about 0.0625% (e.g. a 1:16 ratio) of the increase in lateral distance of placement of the aperture. Other embodiments provide an apparatus and method for providing neuro-electric feedback to assess the degrees of neural ablation. This provides for real time monitoring of the amount of ablation as well as providing a clinical endpoint. Yet another embodiment of the invention provides an apparatus and method for employing a pressure or force sensor to determine the amount of force a tumor imparts on the surrounding bone pre and post ablation so as to determine a clinical endpoint for a bone treatment procedure to reduce pain as well as other tumor related complications.

In use, apertures 260 allow the infusion of a fluid over all or a portion of the perimeter of a tissue tumor site 266.

Aperture(s) 260 can be configured to direct fluid inward into the tumor site, outward into the tumor bone interface or combinations thereof. In various embodiments, this can be achieved by having the apertures oriented radially inward, outward or combinations thereof. In an embodiment, the placement and/or patency of apertures 260 is directable such that the physician can direct the infusion into a selectable circumferential portion of the tumor mass either directed inward or outward.

In the embodiment of FIG. 19B, the control of aperture patency is achieved through the use of a slidable sheath 268 that covers a selectable portion of apertures 260. The slidable sheath can be configured to slide over the outer portion of the helix or slide through the inner lumen while still not appreciably obstructing fluid flow through the lumen. Positioning of the slidable sheath 268 can be controlled through the use of a cam, rocker switch, ratchet mechanism, micropositioner, or servomechanism and the like which is mechanically or electrically coupled to the sheath and actuable by an actuator on the handpiece.

The slidable sheath 268 can be made from a variety of resilient polymers including elastomers, polyesters, polyimides, fluoropolymers and the like. Slidable sheath 268 can be configured to be both electrically and thermally insulative or can be electrically and thermally conductive using conductive polymers known in the art. An example of a conductive polymer includes Durethane C manufactured by the Mearthane Products Corporation (Cranston, R.I.). Also, all or a portion of the slideable sheath can have radio-opaque, magno-opque, or echogenic markers to facilitate viewing and placement of the sheath using X-ray, CAT scans, NMR ultrasound and the like.

The use of apertures 260 to deliver a conductive or other fluid 270 provides a means for performing or achieving several functions in treating bone disease particularly with minimally invasive methods. These include ensuring a more complete necrosis or ablation around all or a selected portion of the tumor mass 266 or tumor perimeter while reducing or eliminating the amount of charring, desiccation and concomitant injury of healthy surrounding tissue particularly critical tissue such as blood vessels and nerves and the like. Also, the delivery of fluid can be performed using pressure or velocity to force fluid into all or portion of the tumor mass. Infusion pressure can be selectable and can be in the range of 0.01 to 30 atms with specific embodiments of 0.25. 0.5, 1, 5 10, 20 and 25 atms. Pressures can be continuous, pulsed or combinations thereof including various pressure waveforms. Examples of pressure waveforms that can be used include, but are not limited to, sinusoidal, saw tooth, square wave and combinations thereof. Such waveforms can be generated by peristaltic pumps or other fluid delivery devices known in the art including programmable pumps manufactured by the Cole Palmer Corporation or the Harvard Corporation.

Another embodiment of the invention can include an infusion apparatus coupled to apertures 260 that controllably delivers an electrolytic solution 270 to a bone tumor and then delivers RF energy which is conducted by the electrolytic solution throughout the tumor space to ablate the tumor. Solution 270 can include a viscoelastic conductive gel or paste 272 with sufficient viscosity to be contained in a bone tumor volume 266 during the period of ablation so as to uniformly delivery electromagnetic energy to the entire tumor. The viscosity of gel 272 can range from 3 to 500 centipoise with specific embodiments of 5, 10, 25, 100, 250 and 400 centipoise. An example of a conductive viscoelastic gel includes a mixture of carboxymethyl cellulose gels made from aqueous electrolytic solutions such as a saline solution (which can be hypotonic, physiologic or hypertonic). Another example of a conductive viscoelastic gel includes a high molecular weight polysaccharide and at least one polyol as described in U.S. Pat. No. 4,299,231.

Figure 19D:
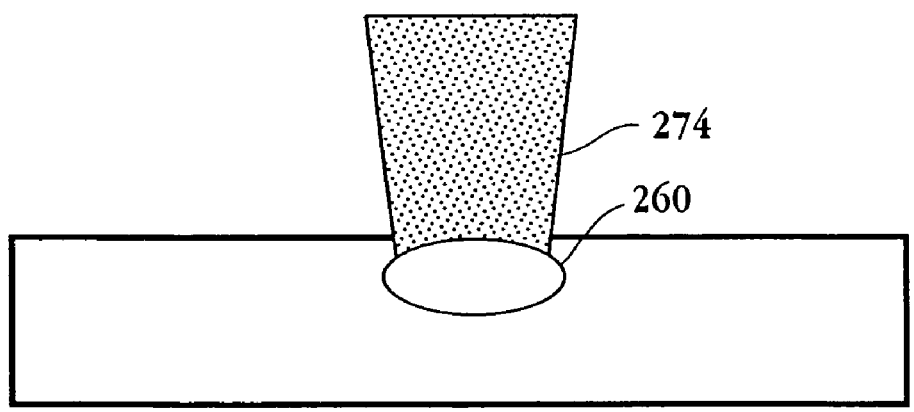
FIG. 19D shows an aperture and fluid jet of the coiled electrode.

In the embodiment of FIGS. 19C and 19D, apertures 260 are configured to produce a jet of fluid 274 (including a venturi jet) which has sufficient force to penetrate tumor tissue but not healthy bone and surrounding tissue. This can be accomplished through selection of the diameter 262 and shape 264 of apertures 260 along with infusion fluid pressure. The velocity of the fluid jet can be in the range of 1 to 10,000 cms/sec with specific embodiments of 10, 50 100, 500, 1000, 2500, and 5000 cms/sec. In an embodiment the jet velocity is controlled through control of the fluid pressure which can be controlled via use of a control system described herein or otherwise known in the art.

Other embodiments of the invention can be configured for intraosseous injection of fluids and liquids into the tissue treatment site. Such fluids can include but are not limited to conduction enhancing fluids such as saline solutions, bone cements, carbonated apatite and/or hydroxyapatite, medicaments, chemotherapeutic agents collagen, biopolymers, osseous tissue, fibroblasts and the like. In an embodiment of the apparatus configured for intraosseous injection, the introducer 276 includes a shaft with a lumen terminating at a distal end in a frusto-conical connector portion for interconnection with cortical bone tissue and a handle or handpiece associated with the introducer to enable the shaft to be screwed into the cortical bone. The handpiece may extend perpendicularly to the axis of the shaft. The connector may be screw-threaded and may be configured such that when the nozzle of the shaft comes into contact with the cortical bone, a single turn by the user will lock the shaft into the bone into the cortical bore. The proximal end of the shaft can terminate in a hub, this hub defining a recessed portion for the releasable engagement of manipulatable parts.

The manipulated parts may include a needle carrying hub provided with a hollow vented double needle, through which passes the injectable composition with an annular space to allow venting of blood, liquids and tissue from the bore. Alternatively, the manipulatable portions. can include a guide wire-carrying hub. Also the needle-carrying hub can be provided with a proximal chamber for operative engagement with a syringe, syringe pump or other fluid delivery device. The syringe may be adapted to inject the intraosseous composition and may include means whereby the needle may be withdrawn during the injection sequence, so that intraosseous liquid is applied under pressure over a selected length of a bore in an osseous or other target tissue site.

Figure 20:
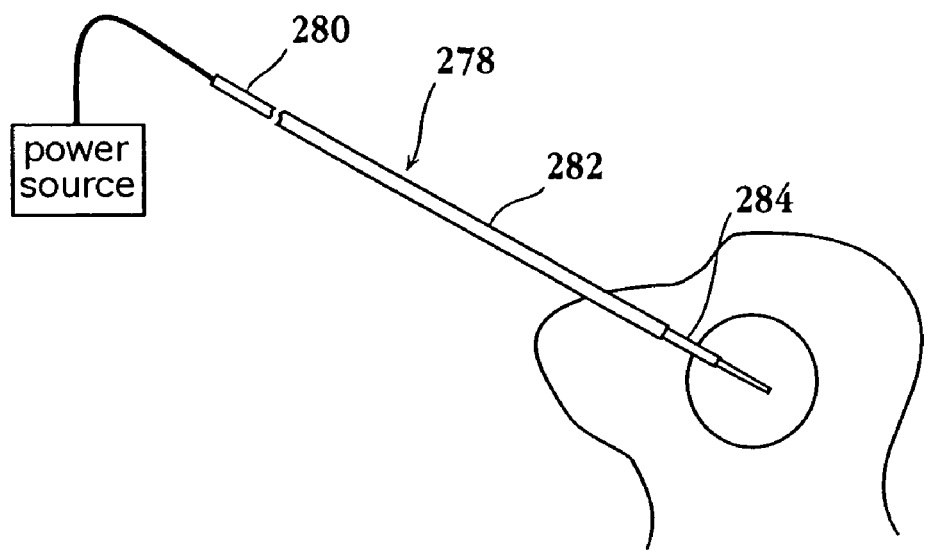
FIG. 20 illustrates a bone treatment device of an embodiment for use with an orthopedic device, for example, an access or insertion device.

In various embodiments, apparatus 278 can be configured for use with assorted orthopedic devices including, but not limited to, bone biopsy devices, bone drills, bone dilators, bone access ports and the like. FIG. 20 is a bone treatment device of an embodiment for use with an orthopedic device, for example, an access or insertion device. The introducer 280 can be configured to allow the passage of an orthopedic device 282 such as a bone drill, and/or bone dilator through the trocar/introducer lumen. This can be achieved by configuring the introducer with sufficient inner diameter to allow the advancement of such devices. In various embodiments the inner diameter of the introducer can range from 0.05 to 1 inches with specific embodiments of 0.070, 0.125, 0.25, 0.4, 0.5, 0.75, 0.8 inches.

In related embodiments the distal section 284 of introducer 280 can be also configured to allow the coupling, including detachable coupling, of a variety of medical device/orthopedic tool attachments including but not limited to bone drills, bone chisels, bone biopsy needles/devices, guidewires and the like. Suitable means for detachable coupling include use of snap fit mechanisms, collars, locking tapers, and the like. Suitable bone access ports can include both permanent or temporary types. An example of a bone access port is described in U.S. Pat. No. 5,990,382.

Suitable bone drills can have a distal end that includes a pointed distal tip and a plurality of cutting flutes circumferentially spaced around the distal end proximally adjacent to the tip. The drill can also include markings to indicate a depth of the hole. The drill tip has a pointed configuration adapted to reduce movement of the drill tip on the bone surface during the drilling process so that the bone access holes can be positioned more accurately. The drill can have a range of diameters from 0.5 to 10 mm with specific embodiments of 2.7 mm, 3.5 mm, 4.5 mm, 6.5 mm or 8.5 mm. Embodiments of the invention can be configured to be used with commercially available bone drills known in the art.

In use, the bone dilator is configured to enlarge the hole made by the bone drill or other bone access device known in the art. In various embodiments, the dilator can enlarge a drill or access hole in the range of 0.1 mm to 1 mm with specific embodiments of 0.2, 0.4, 0.6 and 0.8 mm. Dilator can be a solid metal rod that is axially elongated between proximal and distal ends. The diameter at distal end corresponds to the diameter of drill with which dilator is used. The edge of distal end can be slightly chamfered to allow dilator to be easily inserted into the hole. In alternative embodiments the dilator can be integral to or otherwise coupled to the introducer including distal portion 280 of the introducer. In a specific embodiment the dilator and introducer can be configured to permit the dilator to be detachably coupled to the introducer using snap fit mechanisms, collars, locking tapers, and the like.

Suitable bone dilators can be tapered proximally or distally and can also include insertion markers. In an embodiment the dilator can have a distal taper of approximately 0.2 mm over a lateral distance of 15 mm to a final diameter of 4.7 mm from a distal end diameter of 4.5 mm. The lateral section can have graduated markings near its proximal and distal ends, so that the physician can see the position of dilator when inserted through the introducer. A transverse hole can be provided near proximal end and is sized to receive a tamp to form a "T" shaped assembly that provides the surgeon with increased leverage when using the dilator to enlarge the graft-receiving hole.

Figure 21:
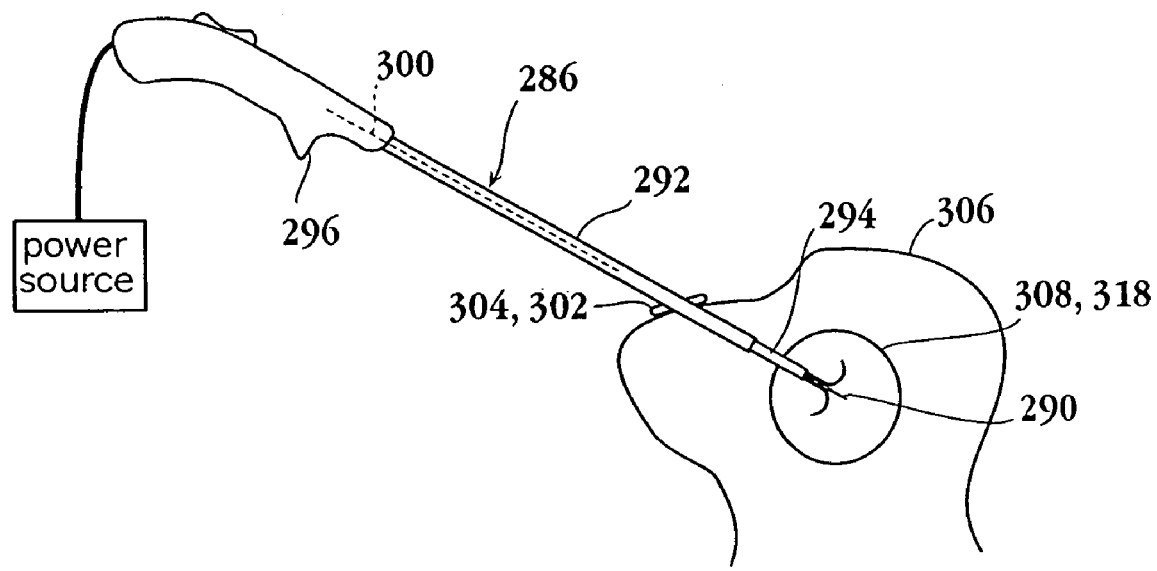
FIG. 21 shows a bone treatment device in which the introducer is a bone access device, under an embodiment.
Figure 22:
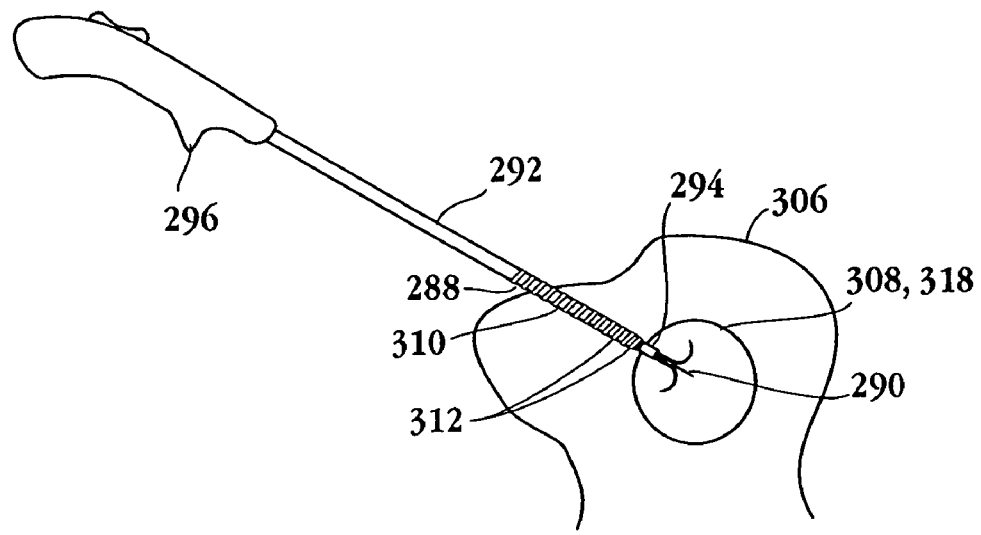
FIG. 22 illustrates a bone treatment apparatus having a threaded bone penetrating introducer, under an alternative embodiment.
Figure 23A:
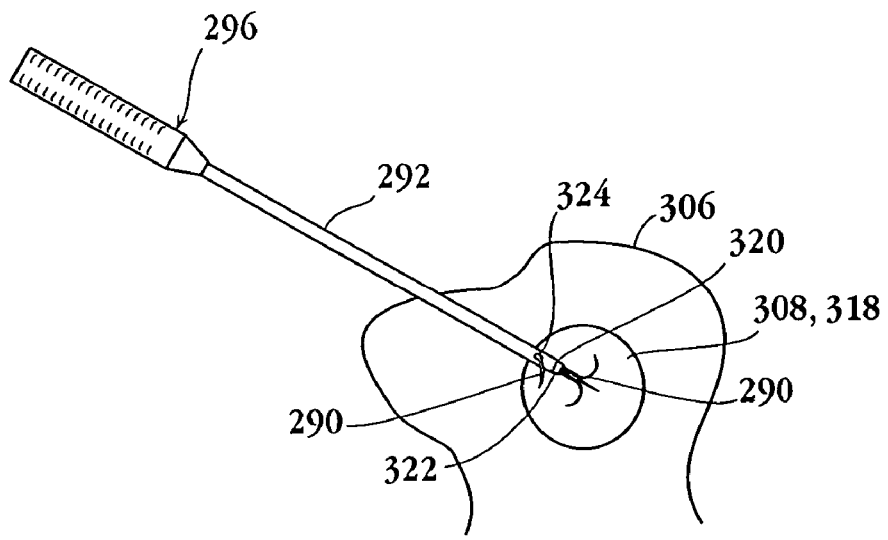
FIGS. 23A and 23B show a bone treatment device including an introducer with a bone drill tip, under another alternative embodiment.
Figure 23B:
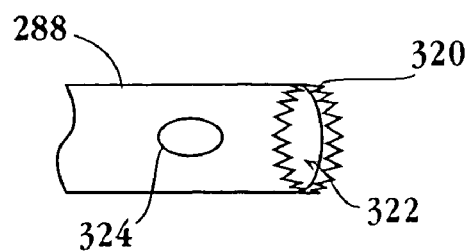

FIG. 21 shows a bone treatment device 286 in which the introducer is a bone access device, under an embodiment. FIG. 22 is a bone treatment apparatus 286 having a threaded bone penetrating introducer, under an alternative embodiment. FIGS. 23A and 23B show a bone treatment device 286 including an introducer with a bone drill tip, under another alternative embodiment. With reference to these Figures, the introducer, including distal section 288, can be configured for insertion, positioning and anchoring into bone tissue or otherwise provide percutaneous access to a target bone tissue site while still permitting the deployment of electrodes 290. Accordingly portions of introducer 292 can include or otherwise be configured as a bone access or insertion device such as a bone screw, bone drill, bone dilator, bone chisel and the like.

In the embodiment of FIG. 21 introducer 292 can be configured as a bone trocar known in the art with a trocar tip 288. Further, introducer 292 has sufficient column strength and distal section 288 including tip 294 has sufficient sharpness and hardness to enable introducer 292 to pushed, rotated or otherwise driven into the bone tissue by the physician. The force can be applied via a proximal fitting or handpiece 296 coupled to the proximal end of introducer 292. Proximal fitting 296 can be in the shape of a gripable handpiece which provides the physician with a leverage point to apply force to introducer 292 including distal section 288. In an embodiment handpiece 296 can be solid gripable cylinder (analogous to that on a wine corkscrew) perpendicular to the longitudinal axis 300 of introducer enabling the physician to simultaneously rotate and apply longitudinal force to the introducer so as to screw the introducer into bone tissue.

The distal or tissue-engaging portion of the introducer 288 can include an annular flange 302 that projects distally from the rim. The annular flange 302 is configured for seating on or within the bone tissue. In related embodiments, the tissue-engaging portion 288 of the introducer includes an enlarged lip 304 circumferentially disposed around distal end 288. Lip 304 is configured to anchor or stabilize introducer 292 on the bone 306 over or near tissue site 308 particularly during drilling, screwing into bone tissue by the introducer or bone access device or obturator introduced through the introducer. Both lip 304 and flange 302 are configured to solve the problem of wandering of the introducer tip during bone screwing or drilling operations.

Referring to FIG. 22, introducer 292 can include a threaded section 310 having one or more threads with sufficient pitch, strength and profile to allow introducer 292 to be screwed into bone by a physician to reach the desired target tissue site 308. Threaded section 310 may begin at or near distal end 288 and has sufficient to length enable introducer 292 to access a desired bone tissue site from the skin. However, threaded section 310 can be positioned anywhere on introducer 292 and can extend for any length. The length of threaded section 310 can be in the range of 0.1 to 10 cm with specific embodiments of 1, 2.5, 5 and 7.5 cm. The thread design can either be a 'V' profile or a Buttress profile or other profiles known in the art. Also threaded section 310 can be detachably coupled to introducer 292 using snap fit mechanisms, collars, locking tapers, and the like. In another embodiment, threaded section 310 can be crimped onto and around introducer 292 to provide the physician the ability to add and selectively change the length of the threaded section depending on the location and desired point of access of the target bone site 308. Also in various embodiments, all or a portion of threaded section 310 can include apertures 312 to provide for irrigation of the threaded section during the screwing or drilling operations. Apertures 312 can be fluidically coupled to a source of cooling or other fluid such as an electrolytic fluid or a chemotherapeutic fluid.

The introducer tip and threaded section 310 can have a variety of configurations depending upon the type of bone to be accessed, access depth, access site, tumor type and other clinical needs. These configurations include, but are not limited to, the following: (i) a blunt tip for self-tapping embodiments (suited for cortical bone; fluted to act as a cutting edge & transport bone chips away from the entry point with the sharpness, number & geometry of flutes determining its effectiveness); (ii) a blunt tip for non-self-tapping embodiments (suited for cortical bone: the rounded tip allows for more accuracy & direction into a pre-tapped hole). More effective torque is obtained from pre-tapping increased interfragmentary compression); (iii) a corkscrew tip (suited for cancellous bone here the screw compresses trabecular bone & produces compression by overshooting the pre-drilled hole; (iv) a trocar tip, (this embodiment doesn't have a flute, thus it displaces bone as it advances).

In use, threaded section 310 not only enables introducer 292 to be controllably positioned in a selected bone tissue site 308 but can also be configured to provide tissue samples as well. In specific embodiments bone or tissue cuttings are pushed up the flutes of the threaded sections by bone entering at the cutting point of the threaded section 310. In this way the physician can ascertain proper positioning of introducer 292 in the tumor mass 318 by changes in the color or constituency of the tissue shavings existing from the proximal portions of the flutes the threaded sections. Also threaded sections or drill bit 310 can be configured to cauterize the tissue space or track created by the introducer insertion via the generation of frictional heat from the drilling process. This can be achieved via control of one or more of the following parameters: thread shape and pitch, thread/bit diameter, thread/bit materials and drill speed. In a particular embodiment, drill speed can be controlled to be slower during introducer insertion to allow collection of live tissue and the increased upon introducer removal to generate sufficient temperatures (e.g. >50° C.) to cauterize or necrose tissue in the drill track. In various embodiment drill speed can range from 1 to 10,000 revolutions per minute (rpm) with specific embodiments of 50, 100, 500, 1000, 2500, 5000 and 7500 rpm.

Referring to FIGS. 23A and 23B, the distal end 288 of introducer 292 can be a section 320 configured for use as a bone drill or other bone penetrating device, thereby enabling introducer 292 to be turned or screwed into bone tissue. In various embodiments tip 320 can have a variety of drill shapes known in the art including but not limited to serrated, star or x-shaped and trocar shaped. The distal end 288 can still have an opening or aperture 232 at its tip 294 or a lateral opening 324 near the tip, one or both configured to allow electrode advancement and deployment into bone tissue site 308 including tumor mass 318. The shape and diameter of opening 322 can be configured to either displace or collect tissue during introduction of the introducer into bone tissue. In a specific embodiment opening 322 along with a lumen 324 are configured to collect a core biopsy sample from bone tissue site 318 during or after positioning of the introducer at the tissue site. In alternative embodiments bit section 320 can in the form of reciprocating bit made of a piezoelectric material that changes its shape when an electric current is applied. This shape change can be configured as an increase in length so as to provide a drill punch affect in a longitudinal direction.

Figure 24A:
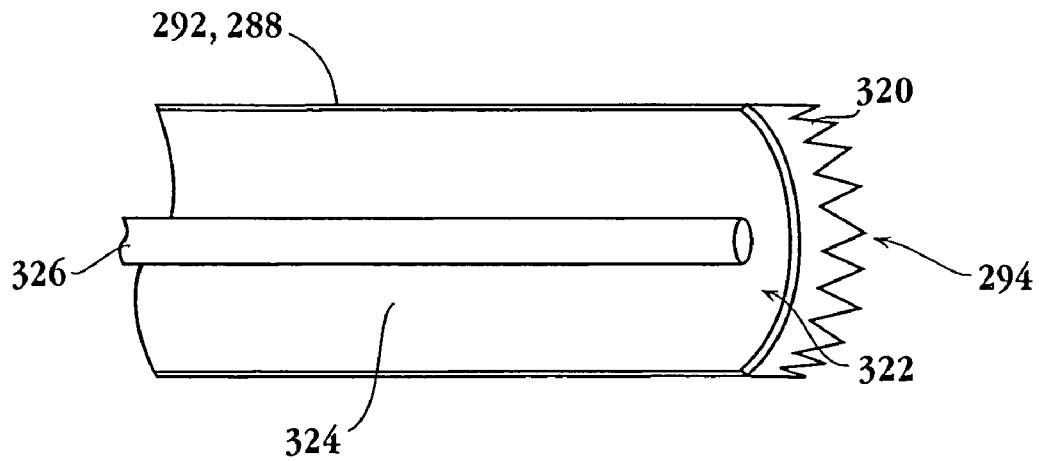
FIGS. 24A and 24C illustrate a bone treatment device of an embodiment including an introducer drill tip configured to be plugged by an insertable wire.
Figure 24B:
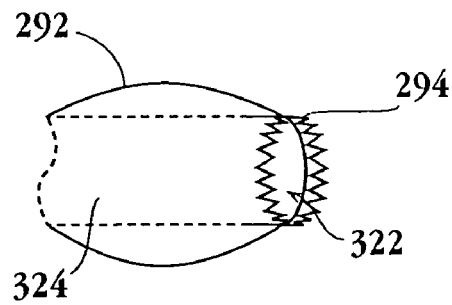
FIG. 24B illustrates a bone treatment device including an introducer having a collapsible distal section, under an alternative embodiment.
Figure 24C:
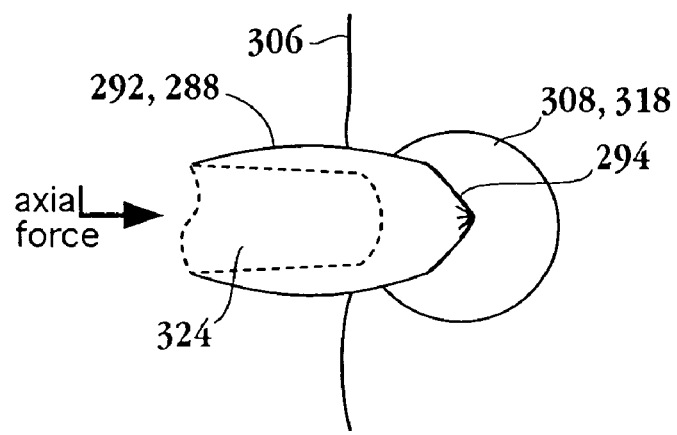

In various embodiments apparatus 286 can be configured such that opening 322 is closed during insertion of the introducer into bone and then opened (fully or partially) once the distal section 288 is placed at the desire bone tissue site 318. FIG. 24A is a bone treatment device of an embodiment including an introducer drill tip configured to be plugged by an inserted wire. FIG. 24B is a bone treatment device including an introducer having a collapsible distal section, under an alternative embodiment. The embodiment of FIG. 24A uses a removable wire 326 which can be a core wire that is placed in central lumen 324 (so as to fill aperture 322) during introducer insertion and then removed.

Referring to FIG. 24B, distal tip 294 can have a nose cone shape that is metallurgically treated (e.g. given spring memory) or otherwise constructed with outwardly flaring sections so as to reversibly compress or collapse in an inward radial direction so as to fill or close aperture 322 when an axial force is applied to the tip 294 (such as from the drilling process) and then reassume its original diameter and shape once the force is removed. These embodiments solve the problem of having an introducer that is configured to function both as a bone insertion/assess device and also act as a conduit to allow electrode advancement without having to remove or provide another introducer or ablation device cutting down on procedure time and reducing the risks of drill/biopsy tract contamination by cancerous or otherwise tumorous tissue.

Figure 25A:
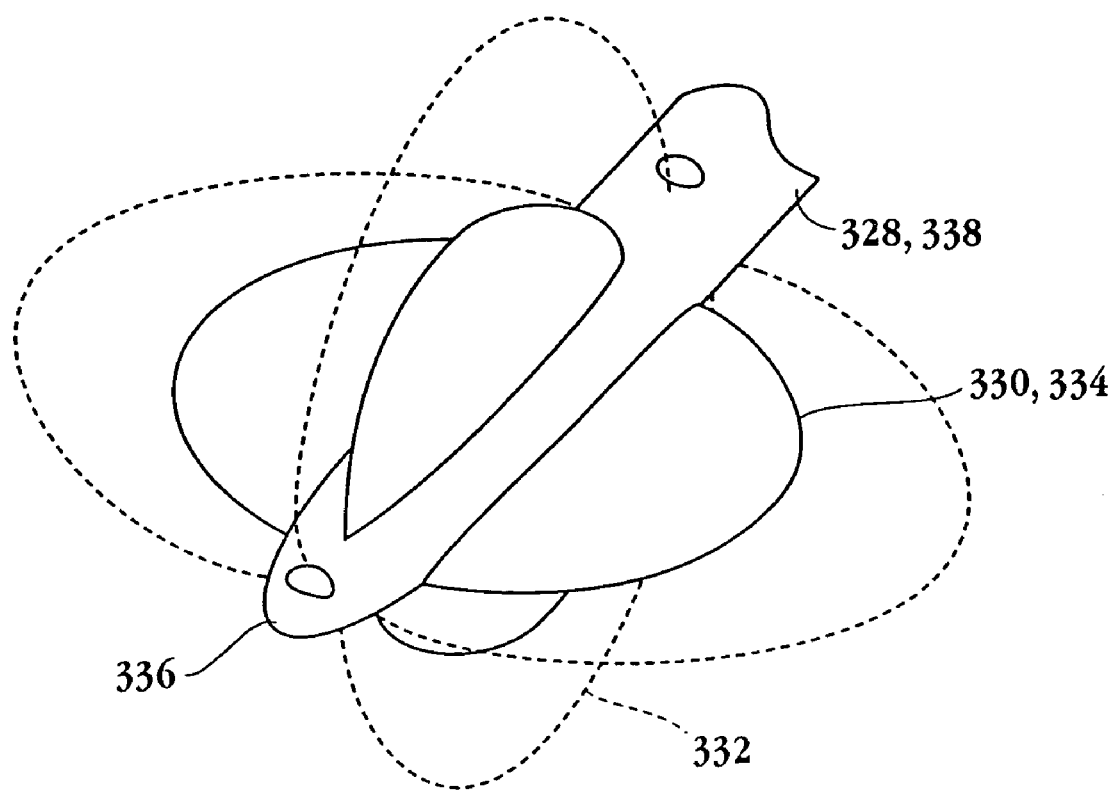
FIGS. 25A and 25B illustrates a bone treatment apparatus having radio frequency (RF) antennas, under an embodiment.
Figure 25B:
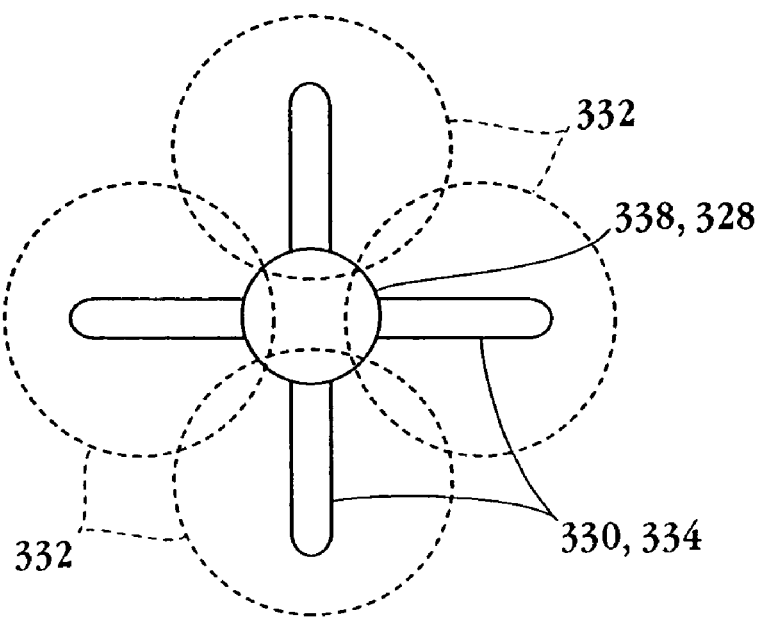
Figure 26:
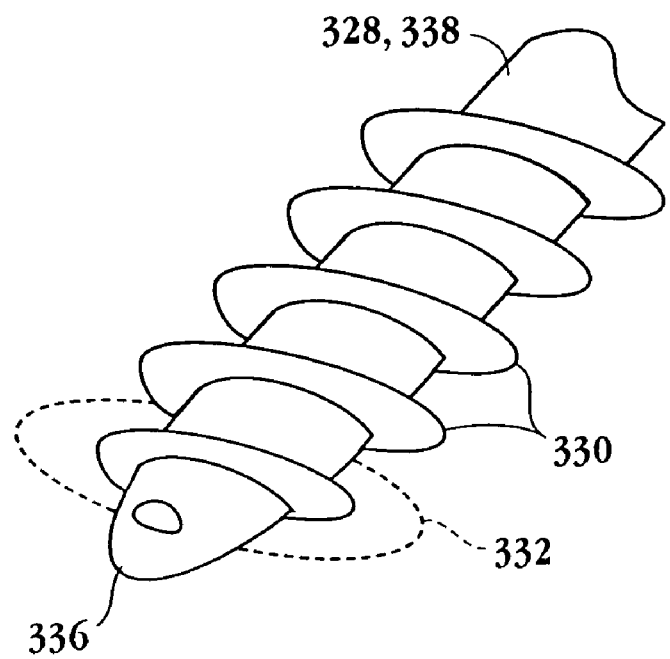
FIG. 26 illustrates a treatment apparatus having shaped protruding spiral RF antennas, under an alternative embodiment.

FIGS. 25A and 25B are a bone treatment apparatus having radio frequency (RF) antennas, under an embodiment. FIG. 26 is a treatment apparatus having shaped protruding spiral RF antennas, under an alternative embodiment. In various embodiments the distal section 328 of the introducer can include shaped protrusions 330 that act as RF or microwave antennas and the like. Shaped protrusions 330, or antennas, have sufficient surface area and shape to deliver RF energy to a large area of tumor tissue with substantially uniform current density while minimizing charring and tissue desiccation. Each protrusion produces a resulting ablation volume or zone 332 for a given power level and duration of energy delivery. The number and position of protrusions 330 can be configured such that the resulting ablation zones 332 surrounding one protrusion selectively overlaps that of another protrusion. In this way the shape and volume of the resulting ablation zone can be precisely controlled.

The protrusions can be fin-shaped having a smooth edge or an edge having sufficient sharpness to cut tissue shape or a combination of both. The smooth edge which can be a radiused or rounded edge reduces current density edge effects. The sharp edge enables quick deployment and positioning in tumor tissue. Fins 334 provide an RF antenna that has a large surface area to uniformly conduct RF energy to tissue without charring. The fins can have a variety of shapes, for example, shapes including that of a triangle, equilateral triangle, isosceles triangle, right triangle, curved triangle, semi-circle, oval, parabolic, hyperbolic, curved, and various combinations thereof. Also the fins can have a curved or pointed profile or a combination of both.

In the embodiment of FIG. 26, the protrusions 330 are spiral shaped. Spirals 330 can be configured to provide a large surface area with which to conduct RF energy in two or more geometric planes to produce an ablation volume with a reduced likelihood of charring. Such spirals can include one or more threads from threaded portion 336 on the introducer. These along with other related embodiments provide a single structure that is able to both cut or penetrate bone tissue as well as conduct RF energy to generate ablation volume, thus reducing tumor treatment procedure time and cost.

Protrusions 330 can be fixedly attached to introducer 338 so as to be inserted or advanced into bone tissue along with the distal section 340. In alternative embodiments, they can be configured to be deployable. Shaped protrusions 330 can be maintained in a compacted or constrained state within introducer 338 during tissue introduction and then subsequently deployed once the introducer is in position at the target tissue site using a deployment mechanism described herein. An example of a deployment mechanism includes a spring mechanism wherein protrusions 330 are coupled to a spring (e.g. a leaf spring) positioned within the introducer 338. The spring mechanism is controlled by an actuator on the handpiece via a controlling wire mechanically coupled to the spring and the actuator.

Figure 27:
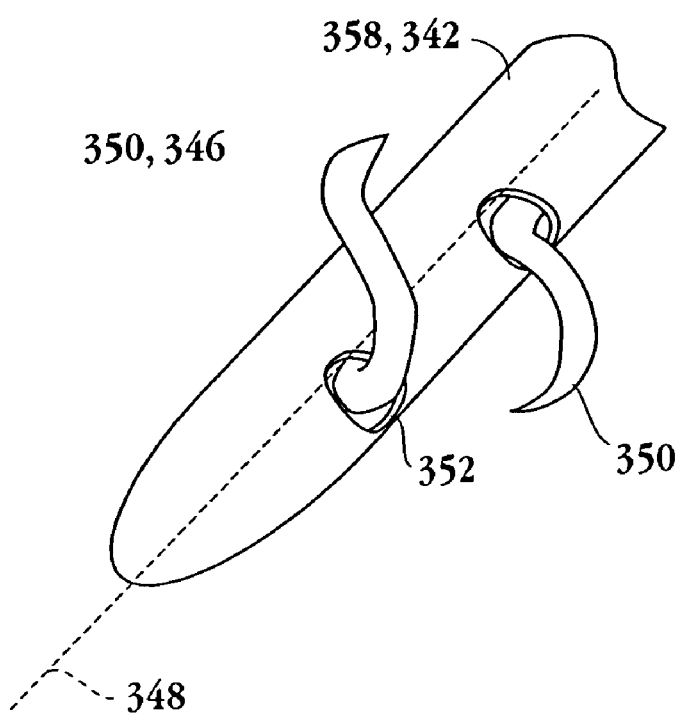
FIG. 27 shows the curvilinear/hook-shaped RF antennas of another alternative embodiment.
Figure 28:
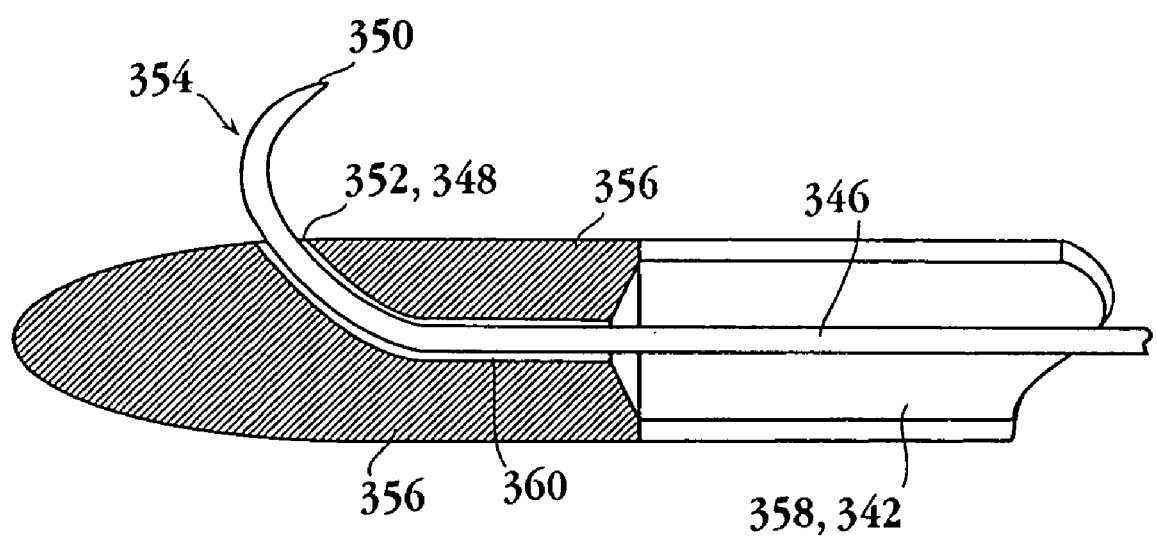
FIG. 28 illustrates a treatment apparatus of yet another alternative embodiment that includes a deflection fixture.
Figure 29A:
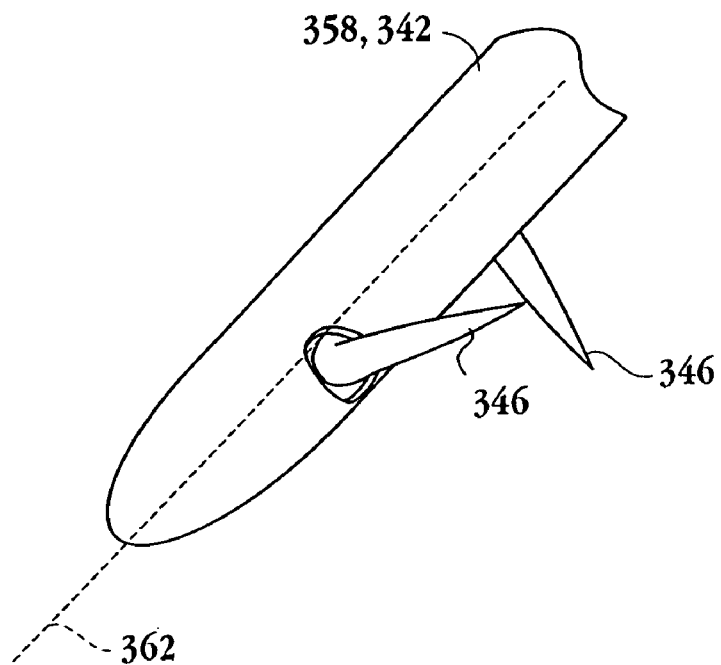
FIGS. 29A and 29B show deployment of RF electrodes, under the embodiments of FIG. 27 or 28.
Figure 29B:
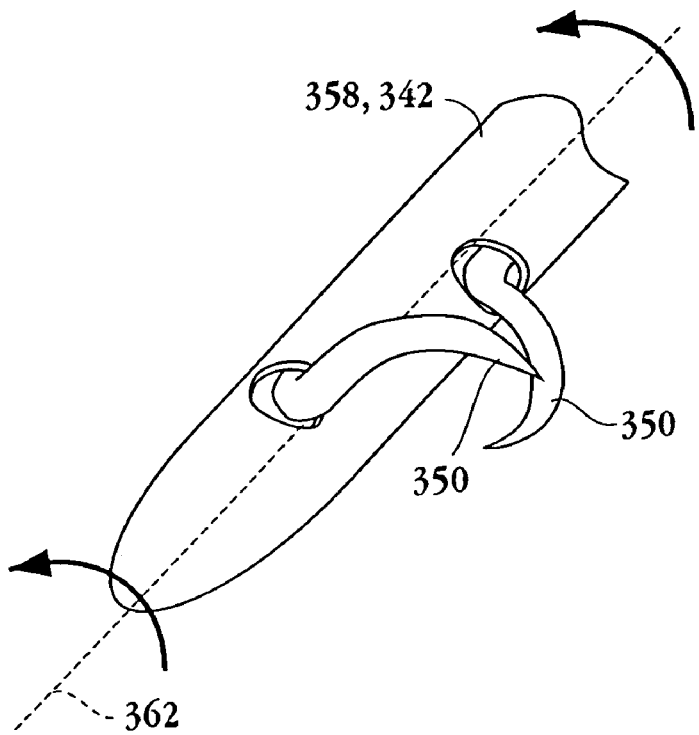

FIG. 27 shows the curvilinear/hook-shaped RF antennas of another alternative embodiment. FIG. 28 is a treatment apparatus of yet another alternative embodiment that includes a deflection fixture. FIGS. 29A and 29B show deployment of RF electrodes, under the embodiments of FIG. 27 or 28. Introducer 342 includes one or more lateral apertures 352 configured to allow the deployment of one or more electrodes. As shown in FIG. 27, electrodes 346 can be curvilinear or hooked shaped with the plane of the hook being substantially perpendicular to longitudinal axis 348 or at a selectable angle thereto. Hooked electrodes 350 can have a nondeployed and deployed state. In the non-deployed state hooks are contained within introducer 342. When advanced out of the introducer 342 through side portal 352 and into tissue hook electrodes 350 assume their hooked shape. This can be accomplished by several different embodiments or combinations thereof. In one embodiment hook electrodes 350 are preshaped or given memory (by metallurgical methods described herein) to assume the hook shape once they are released from the interior of introducer 342.

In another embodiment shown in FIG. 28, the distal portion 354 of electrodes 346 are diverted by a deflecting fixture 356 located in distal introducer portion 358. Deflecting fixture 356 may be located adjacent aperture 352. Deflecting fixture 356 can have one or more curved sections or lumens 360 which curvedly deflects electrodes 350 as they are advanced through lumens 360 and into tissue.

In yet another embodiment shown in FIGS. 29A and 29B, electrodes 350 are advanced out of apertures 352 in a substantially straight fashion, either perpendicular or a selectable angle with respect to the introducer longitudinal axis 362. Introducer 342 is then rotated by the user or physician (using handpiece or other manipulating or grasping means) along the longitudinal axis 362 causing electrodes 346 to twist into hook shaped electrodes 350. This allows the physician to produce a selectable amount of twist or hook in electrodes 350 and thus control the size of the resulting ablation volume. One or more or the three preceding embodiments may also be combined to produce the desired shape electrodes. Also, distal introducer section 358 can include any number of portals 352 which can be distributed along any desired portion of section 358 including but not limited to the sides and ends of section 358 and combinations thereof. This in turn allows, the selective deployment of hooked electrodes 346 along length or perimeter portion of section 358 so as to define one or more selective ablation volumes. Again ablation volumes or zones can be configured to overlap.

In various embodiments bone tumors can be treated with acoustical energy such as ultrasound or very high frequency ultrasound. The delivery of ultrasound energy can also be combined with RF ablative energy to increase the necrotic/ablative effect. The ultrasound energy can be further selected at a resonant frequency of the tumor tissue but not healthy tissue. The frequency of the ultrasound energy can range from 1 to 1000 MHz with specific embodiments of 2, 3, 5, 10, 20, 30 and 40 Mhz. In other embodiments the ultrasound energy can be in the Gigahertz range. The ultrasound probe can include a piezoelectric crystal known in the art.

In order to diagnose the presence of numerous bone and blood-related diseases, such as blood infections, leukemia and other malignancies, physicians often examine the bone marrow of their patients. Accordingly various embodiments of the invention can be configured for use in conjunction with bone biopsy devices and related procedures.

Two types of biopsy specimens are often removed from a patient for analysis: an aspirated biopsy and a core biopsy. In the aspirate biopsy procedure, bone marrow is extracted, or aspirated, from the cavity of a bone. In the core biopsy procedure, one or more pieces of bone, called "core biopsies," or "bone plugs," are also removed for diagnosis.

These two procedures can be performed in succession. First, a specialized, biopsy needle having a removable trocar, or stylet, fully inserted into the needle lumen is inserted into and through an appropriate bone structure of the patient, such as the posterior iliac spine (i.e. pelvic bone) or sternum, and into the bone marrow cavity. The trocar is removed and an appropriate method for aspirating the desired amount of marrow tissue into the needle lumen is used. Aspiration may be accomplished by rapidly retracting the plunger of an attached syringe thereby creating a upward, suction force, by employing an aspirator bulb, or by another method known in the art.

In order to perform the subsequent procedure, the needle is retracted a few millimeters until it exits the bone structure from which the marrow was aspirated. Then, the needle is reinserted, this time without the trocar inserted in the lumen, into a neighboring area of the bone in order to effectively core out a piece of bone into the lumen for removal and analysis. The physician often needs to apply a considerable amount of force when coring the bone plug.

Figure 30:
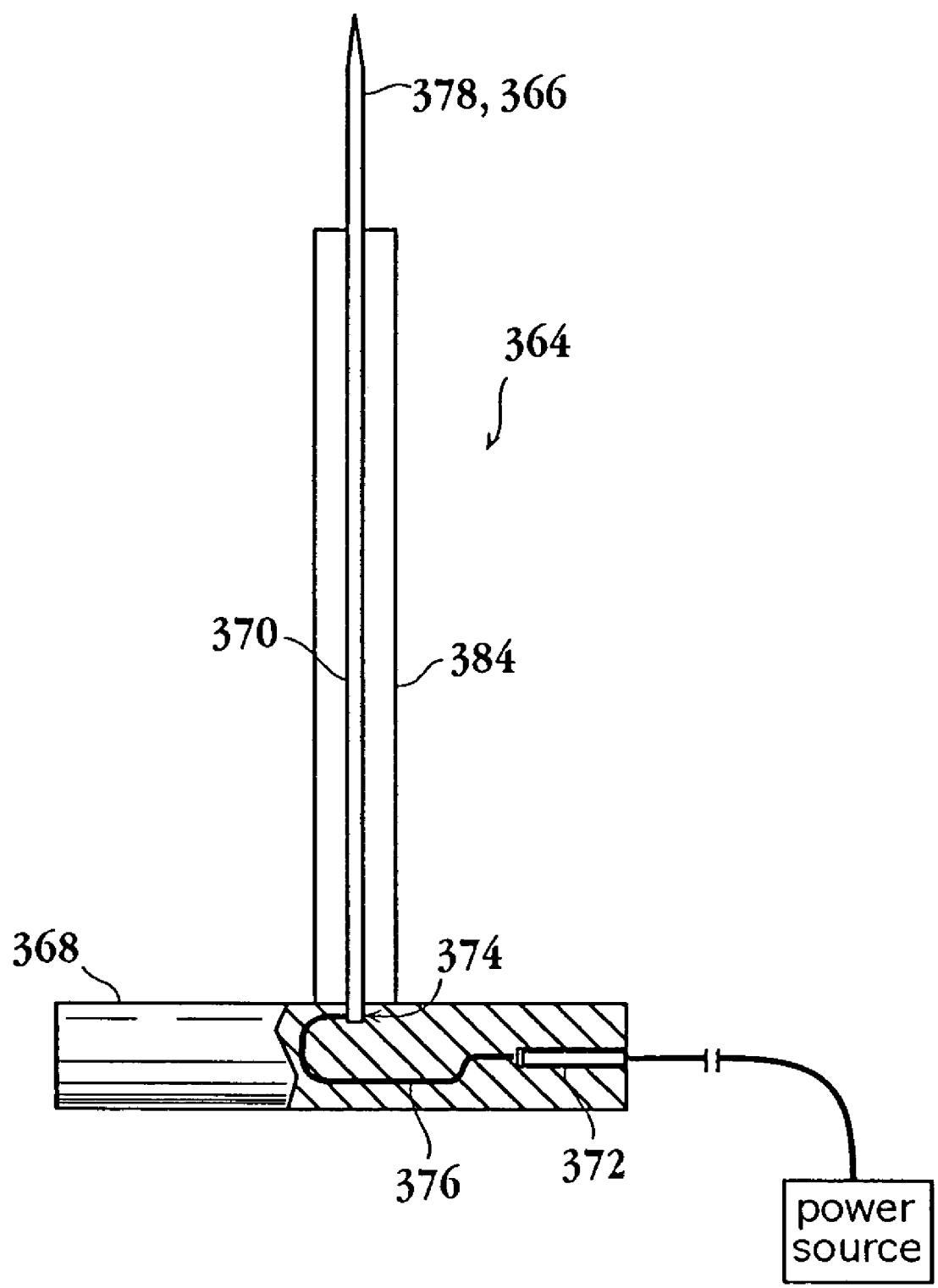
FIG. 30 shows the use of a core biopsy needle/energy delivery device with the bone treatment device, under an embodiment.

FIG. 30 shows the use of a core biopsy needle and energy delivery device with the bone treatment device, under an embodiment. The biopsy needle 366 can be used with apparatus 364 either as an integral or separate device. Biopsy needle 366 can includes a handle 368 and an aspirating needle shaft 370. The handle 368 includes a plug receptacle 372, which is associated with the needle shaft 370 by being electrically connected to the proximal end 374 of the needle shaft 370 via a conductor 376 which can be a conductive wire known in the art. An example of a core biopsy needle includes a Jamshidi® needle. In an embodiment energy delivery device 378 can comprise all or a portion of needle shaft 370 or can other be coupled to needle shaft 370. In this and related embodiments, energy delivery device 378 can be an RF electrode or microwave antenna. The use of energy delivery 378 allows the biopsy site 380 and needle tract to biopsy site to be cauterized and or ablated during or after the biopsy procedure prevent contamination of healthy tissue around the biopsy site.

In other embodiments, all or a portion of apparatus 364 including the introducer 384 and energy delivery device 378 can be made from non-ferrous, nonmagnetic but electrically conductive materials. These materials are compatible with use in close proximity to high strength magnetic fields such as those found around nuclear magnetic resonance imaging (MRI) equipment. This can be achieved by constructing all or a portion of apparatus 364 from conductive polymers known in the art. In an embodiment, the energy delivery device and electrodes are made from nonferrrous conducting polymers known in the art.

Further, all or a portion of the electrode can be made from a nonconducting polymer and subsequently coated or doped (using chemical vapor deposition techniques) with a conductive nonferrous/nonmagnetic coating. Examples of conductive nonferrous material include but are not limited to aluminum, brass copper and alloys thereof as well as non-magnetic stainless steels known in the art. In an embodiment, the non-ferrous material can be oxygen-free copper and related alloys. Also, all or portions of the apparatus can be made nonmagnetic by temperature treating conductive components or materials in the apparatus at their magnetic transformation or Curie point temperature.

Embodiments of bone treatment devices described herein support the measurement and use of different bioanalytes to establish a clinical endpoint for ablative therapies. In an embodiment, carcinoembryonic antigen (CEA) can be used as such an bioanalyte. CEA levels can be measured pre and post therapy, along with tumor size and ablative margin. Correlations can be established between tumor size reduction (both absolute and %) as well as margin and a database established for individual patients as well a patient population (e.g. by tumor type, size etc.). Various curve fitting protocols can be employed to establish such correlations including but no limited to least squares analysis and multivariate analysis. Such a database can be used to establish levels of tumor size reduction and ablative margins for individual patients. Further, in embodiments apparatus 364 can include sensors configured to locally detect levels of CEA in and around the tumor site in order to obtain a more accurate and meaningful measure of CEA levels. Such measurement can be obtained pre, post and inter ablation in order to have immediate, short term and midterm feedback on the effectiveness of the treatment. Again by taking localized measurements pre and post ablation a more accurate measurement can obtained of CEA levels and thus a more accurate and meaningful clinical endpoint can be established. In embodiments, in vivo or in vitro sensors to detect CEA can be antibody-based (incorporating a fluorescence or radioactive marker) in order to obtain both a high degree sensitivity and specificity.

Figure 31:
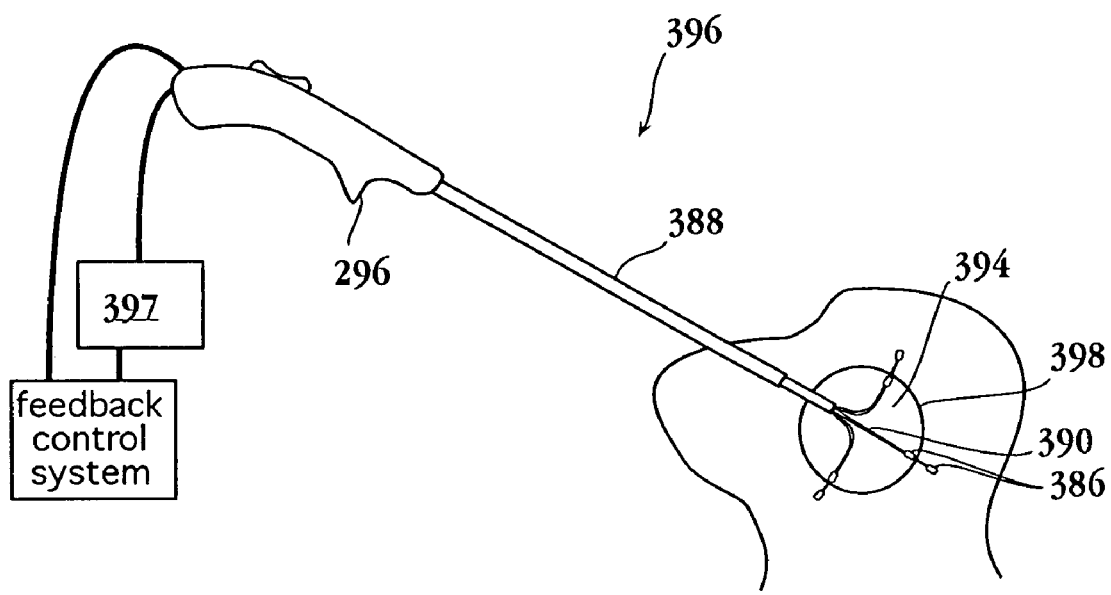
FIG. 31 shows the use of sensors with an embodiment of the bone treatment device.

FIG. 31 shows the use of sensors with an embodiment of the bone treatment device 396. With further reference to the embodiments of FIGS. 1a, 1b, and 2, the use of one or more sensors 386 coupled to the introducer 388, energy delivery devices 390, deployable member 392 or coupled orthopedic devices permits accurate measurement of temperature at tissue site 394. This permits a determination of one or more of the following: (i) the extent of cell necrosis, (ii) the amount of cell necrosis, (iii) whether or not further cell necrosis is needed and (iv) the boundary or periphery of the ablated tissue mass. Further, sensor 386 reduces non-targeted tissue from being injured, destroyed or ablated.

Sensor 386 can be selected to measure temperature, tissue impedance or other tissue property described herein to permit real time monitoring of energy delivery. This reduces damage to healthy tissue surrounding the targeted mass to be ablated. By monitoring the temperature at various points within and outside of the interior of tissue site 394, a determination of the selected tissue mass periphery can be made, as well as a determination of when cell necrosis is complete. If at any time, sensor 386 determines that a desired cell necrosis temperature is exceeded, then an appropriate feedback signal is received at power source 397 coupled to energy delivery device 390 which then regulates the amount of electromagnetic energy delivered to electrodes 390.

In various embodiments, at least a portion of sensors 386 can be pressure or force sensors configured to detect the amount the of pressure applied by tumor mass 394 to the surrounding healthy tissue, including to tumor-healthy tissue border 398. Pressure or force sensors 386 can strain gauges, silicon based pressure sensors, accelerometers, semiconductor gauge sensors, silicon strain gauges, heat resistant silicon strain gauges, micro-machined pressure sensors and the like. In an embodiment pressure sensor 386 can be a flexible silicon strain gauge manufactured by the BF Goodrich Advanced Micro Machines (Burnsville, Minn.).

One or more pressure sensors 386 can be positioned along the length of one or more energy delivery device 390 or introducer 388 so as to be able measure pressure in multiple locations along the tumor-healthy tissue border 398. In an embodiment, pressure sensors 386 are distributed along the entire deployed length of electrode 390 so as to be able to measure the pressure applied along the entire perimeter or border 398. In related embodiments this configuration can be duplicated for multiple electrodes 390 (or an electrode array) such that measurement of tumor applied pressure can be obtained for all or significant portions of the surface area/border area 398 of the tumor mass. Sensors 386 can be coupled to a multiplexer (described herein) so as to integrate the signal from one or more sensors 386 to obtain a composite picture of the applied pressure of all or selected portions of the tumor surface area 398.

In practice, pressure sensors 386 allow the physician to measure tumor-applied pressure before, during or after ablative treatment. This provides a method of allowing the physician to quantitatively determine a pressure/force reduction produced for a given amount of tissue ablation and hence a predictable level of pain reduction at tumor site. This in turn provides the physician with a quantitative and meaningful clinical endpoint for tissue ablation therapy to reduce tumor related pain in a bone or other tumor or lesion. Also use of sensor 386 allows the physician to rapidly identify areas along the tumor border 398 causing the greatest amount of pressure to an area of bone and hence pain and direct delivery of ablative energy/therapy to those areas via the deployment of energy devices 390 and other means described herein.

Sensor 386 can be of conventional design, including but not limited to thermal sensors, acoustical sensors, optical sensors, pH sensors, gas sensors, flow sensors positional sensors and pressure/force sensors. Thermal sensors can include thermistors, thermocouples, resistive wires, optical sensors and the like. A suitable thermal sensor 386 includes a T type thermocouple with copper constantene, J type, E type, K type, fiber optics, resistive wires, thermocouple IR detectors, and the like. Acoustical sensors can include ultrasound sensors including piezoelectric sensors which can be configured in an array. Pressure and force sensors can include strain gauge sensors including silicon-based strain gauges contained in an miniaturized chip. Optical sensors can include photo-multipliers and micro-machined optical fibers. Gas sensors can include $O_2$ sensors such as Clark electrodes, $CO_2$ sensors and other electrochemical based sensors known in the art. Flow/velocity sensors can include ultrasound sensors, electromagnetic sensors and aneometric sensors which can be configured to detect both liquid and gaseous velocities and flow rates. Positional sensors can include LVDT's, and Hall effect sensors. Other sensors that can be employed include impedance sensors, antibody-based sensors, biosensors (e.g. glucose) and chemical sensors.

In various embodiments one sensor can be configured to detect multiple parameters or one or more sensors can be coupled together. Pressure sensors can be selected and/or configured to detect pressure differentials less than 1 mmHg and even less than 0.1 mmHg. In specific embodiments, pressure sensor 386 can be a micro-machined fiber optic sensor, a PSP-1 pressure sensor manufactured by Gaymar Industries Inc. (Orchard Park, N.Y.), or a Monolithic Integrated Pressure sensor made by the Fraunhofer-Institut (Duisburg, Germany). Also, ultrasound sensor or transducers can be a Model 21362 imaging probe manufactured by the Hewlett Packard Company, Palo Alto, Calif.

Figure 32:
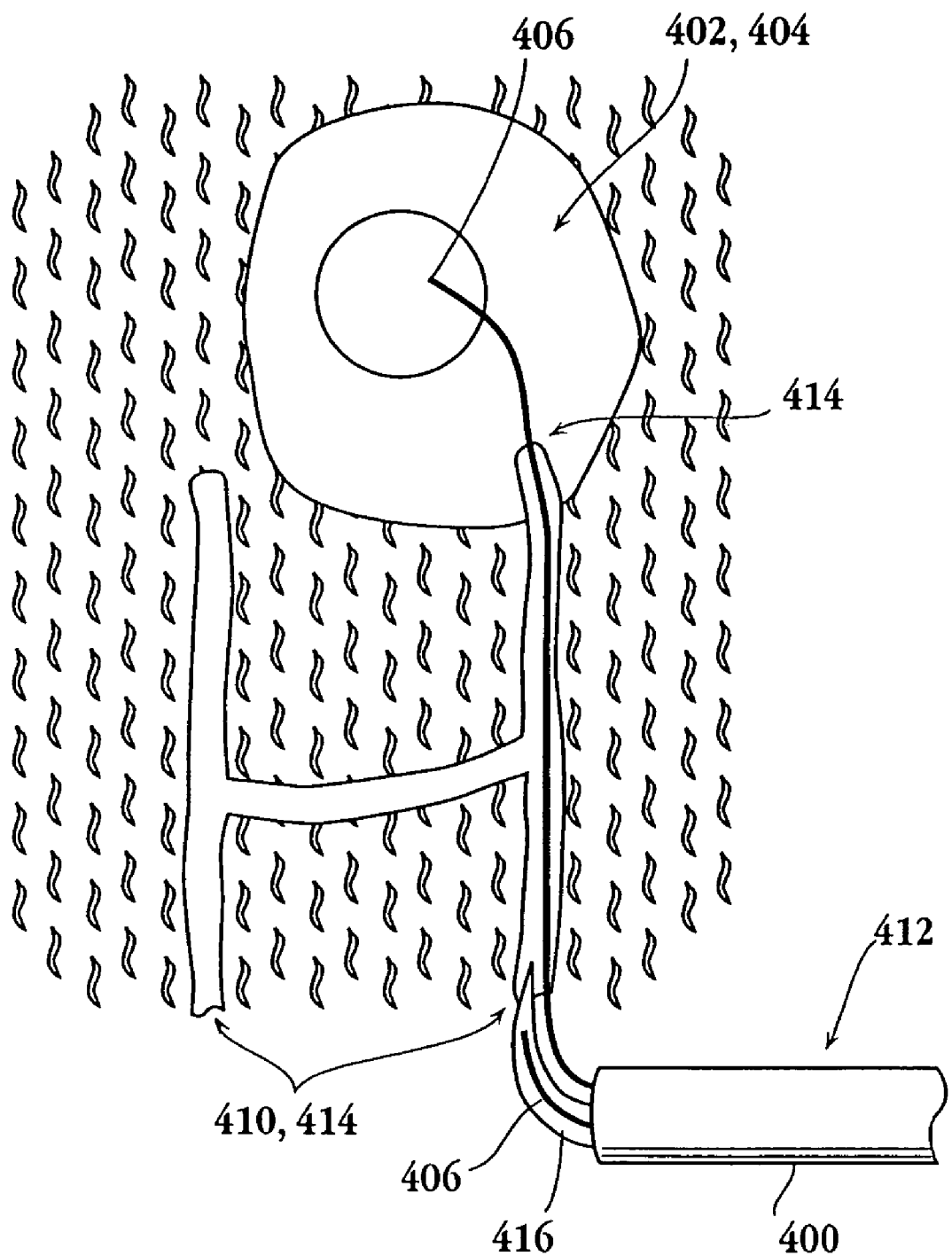
FIG. 32 shows the use of a bone treatment apparatus of an embodiment to deliver energy and/or fluid through the Haversian canals.

FIG. 32 shows the use of a bone treatment apparatus of an embodiment to deliver energy and/or fluid through the Haversian canals. Apparatus 400 can be configured to conduct RF energy or fluids (including conductivity enhancing fluids such as saline) through the Haversian Canals to a target tissue site 402 containing a tumor mass 404. This can accomplished through the use of an energy delivery device 406 comprising one or more long flexible hollow needles which can have a diameter ranging from 0.1 to 1 mm with specific embodiments of 0.2, 0.3, 0.4, 0.5, 0.7, or 0.9 mm. Such needles can have lengths ranging from 0.5 to 20 cms with specific embodiments of 1, 2, 5, 7, 10 and 15 cms. Needles 406 can also include sensors configured to detect the location of one or more Haversian canals 410. Such sensors can include but are not limited to pressure sensors, ultrasonic sensors (which can both be imaging and velocity sensors via Doppler ultrasound) flow sensors and impedance sensors to detect nerve tissue and nerve pathways within the Haversian Canals.

In practice, the physician inserts one or more needles 406 into the Haversian Canals that are in proximity to the desired tumor mass/target tissue site. These canals 410 are used to conduct ablative energy and/or fluids to a difficult to reach or otherwise inaccessible tumor mass 404. The physician can gain access to the canals percutaneously through a trocar 412 or bone access device described herein or surgically through an incision in the bone. In one embodiment needles 406 could be advanced all the way to the tumor mass 402 (using an advancement member) and RF or other energy delivery to the tumor mass. In another embodiment, needles 406 need only be advanced partially through canals and to make electrical contact with one or more Haversian canal nerves 414 and utilize the nerve(s) to conduct RF energy to the desired tumor mass 402. In a related embodiment, sufficient energy can be delivered to canal 410 to ablate selectable portions of one or more nerves 414 innervating tumor 402. Suitable power levels for doing so include a range of 1 to 10W for a period of 10 to 180 seconds with an embodiment using a power range of 5W for a period of 20 seconds. This allows the physician to selectively ablate nerves 414 responsible for pain from the tumor mass 402.

This procedure can be done independently or as a post or pretreatment to a tumor ablation procedure to improve the levels of pain reduction. A potential result of pre-treatment is that by ablating the nerve bundle 414 innervating the tumor mass 402 the pain level to the patient is reduced during the tumor ablation procedure and the risk of resulting reflex movements by the patient tending to dislodge the apparatus and energy delivery devices from the target tissue site is lessened. Nerves 414 innervating the tumor mass can be identified by using electrode 406 to stimulate nerve 414 using evoked response methods.

In other embodiments needles 406 need only be advanced partially through canals 410 and then an electrolytic fluid 416 infused through canals 410 to reach the selected tumor mass 402. The control of the infusion can be achieved via the use of a selectable pressure gradient and flow rate generated by an infusion device such as an infusion pump, Harvard pump or syringe pump fluidically coupled to apparatus 400 including introducer 412 and/or energy delivery device 406. Infusion pressure can be in the range that include but is not limited to 0.1 to 5 atms with specific embodiment of 25, 50, 75, 100, 200 and 700 torr. If blocked a fluidic and/or conductive pathway through canal 410 to tumor mass 404 can be created by delivering sufficient ablative energy from electrode 406 partially inserted in the canal ablatively open pathway by abating or vaporizing tissue obstructing the selected canal(s) leading to the desire tumor site 402.

Figure 33:
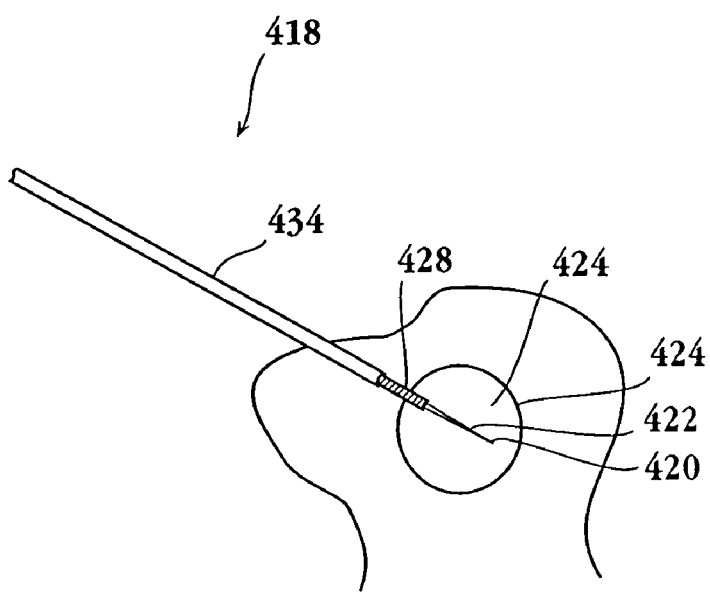
FIG. 33 illustrates an energy delivery device of an embodiment including a radioactive section.

FIG. 33 is an energy delivery device 418 of an embodiment including a radioactive section. In an embodiment, all or a portion of one or more of the energy delivery devices 420 can include a radioactive portion 422. Radioactive portion 422 is fabricated from a radioactive material having sufficient radioactive strength (e.g., curies) to necrose, ablate, ionize or otherwise kill tumorous tissue 424 at tissue site 426. In related embodiments, a radioactive absorbing sheath 428 can be configured to be slidably positioned over radioactive portion 422 so as to control the exposed length of radioactive portion 422 and thus the dose of radioactivity delivered to the tumor mass 424.

The radioactive material in section 422 can include gamma, alpha, or beta emitting materials. Suitable gamma emitters include, but are not limited to. Cobalt-60, Iodine-131, Iodine-123, Indium-111, Gallium-67 and Technetium-99 m. Suitable beta emitting particles include tritium. The amount of radioactive material in portion 422 can be configured to deliver 0.01 to 100 rads of radiation with specific embodiments of 0.1, 0.25, 0.5, 1, 10 and 50 rads. The amount of radiation delivered can measure using a radiation sensor coupled to energy delivery device 420 or introducer 434. Radioactive absorbing sheath 428 can include one or more radioactive absorbing materials known in the art which are impregnated or otherwise integral to a flexible metal or polymer layer. Such radioactive absorbing materials include but are not limited to lead, iron or graphite. In an embodiment, the radioactive absorbing material can be fabricated into a braided wire or sheath incorporated into the wall of sheath 428 using catheter production methods known in the art.

In use, radioactive section 422 and related embodiments provide a radiation therapy having a highly targeted delivery of radioactivity to the tumor mass while minimizing injury to surrounding tissue. The radiation can be delivered alone or as an adjunct to another ablative treatment describe herein (before, during, or after such treatment) to sensitize cancer cells to other forms of necrotic therapy or otherwise increase the probability of killing cancerous tissue. The dose of radiation can be controlled at a level where it has no affect on healthy or untreated tissue but, when combined with another energetic therapy, serves to surpass a lethal threshold for the selected tumorous tissue. In use, such therapy provides an increased probability of killing all the cancer cells at the tumor site and thus an improved clinical outcome for the patient.

Other embodiments of the invention can be configured to employ photodynamic therapy to treat bone tumors. Photodynamic therapy is the use of a light activated compound that is injected into body and taken up by a selected tissue such as a tumor mass. After the substance is taken up by the body tissues, a light source such as a laser is used to illuminate the area and resulting in photochemical reaction which acts to necrose or otherwise injure or destroy the targeted tissue.

The apparatus of an embodiment can be configured to deliver a phototherapeutic agent, or photodynamic agent, to the target tissue site. The agent can be configured to selectively be taken up and/or otherwise selectively bind to bone tumor mass. Once the agent is delivered and taken up by the tumor an optical embodiment of the energy delivery device is used to delivery optical radiation to activate therapeutic agent and cause the necrosis or ablation of tumor mass. However, prior to photo-activation, agent remains in an inert or nontoxic state. Examples of optical energy delivery devices 420 include but are not limited to optical fibers, light pipes, wave-guides and the like. Examples of photo-therapeutic agents include chlorophyll-based compounds such as Bacteriochlorophyll-Serine and texaphyrin based compounds such as lutetium texaphyrin manufactured by Pharmacyclics, Inc. (Sunnyvale, Calif.). Examples of activating radiation include radiation in the infrared, near infrared and ultraviolet range of the spectrum. Such radiation can be delivered by the optical energy delivery devices described herein as well as other optical delivery devices known in the art. In an embodiment, agent can be delivered as a fluid, for example dissolved in a solution, through a bone access device or bone biopsy needle directly to the tumor site, or through the Haversian canals.

In various embodiments, photodynamic therapy can be conducted prior, concurrently or after thermal ablative therapy such as RF ablative therapy. In a related embodiment, photo-agent can also be configured to increase the hyperthermic affect of RF or other electromagnetic energy delivered to tumor mass or otherwise selectively sensitize tumor tissue to the necrotic affects of hyperthermic tumor treatment such as RF ablative treatment. In a specific embodiment the photo-agent is configured to be repelled by healthy bone tissue including calcium-based tissue or collagen based tissue and thus increase the agents specificity for tumorous tissue. In another embodiment the photosentisizing agent can be configured to be activated by a wavelength of light that is reflected by bone tissue yet absorbed by tumorous tissue particularly darker tumorous tissue. Suitable wavelengths can include the range of 400 to 900 nanometers (nm) with specific embodiments of 418, 500, 542, 577, 600, 700 and 800 nm. This and related embodiments provide an agent that is highly specific to tumor tissue yet has little or no affect on healthy bone. Further, the use of agent allows the level of hypothermic treatment to be titrated to the size and type of tumor tissue. This can be accomplished by using a spectrum of agent's that increases or decreases the level of tumor sensitization as needed.

Other embodiments of the treatment device described herein can combine thermal or other ablative therapy described herein with chemotherapy or other medicinal based therapy. The apparatus can be used to deliver various chemotherapeutic or medicinal agents along or in combination before, during or post ablation. One such family of agent includes antisense-based compounds configured to inhibit the metabolism by the liver (by inhibition of liver enzymes) of various chemotherapeutic agents and thus extend their biological half-life (e.g. effectiveness) while minimizing side-affects. An example of such a compound includes NEUGENE® antisense compound manufacture by AVI BioPharma Inc (Portland Oreg.). Such compounds can be delivered directly to the liver using apparatus or other drug delivery device described herein or known in the art.

Figure 34:
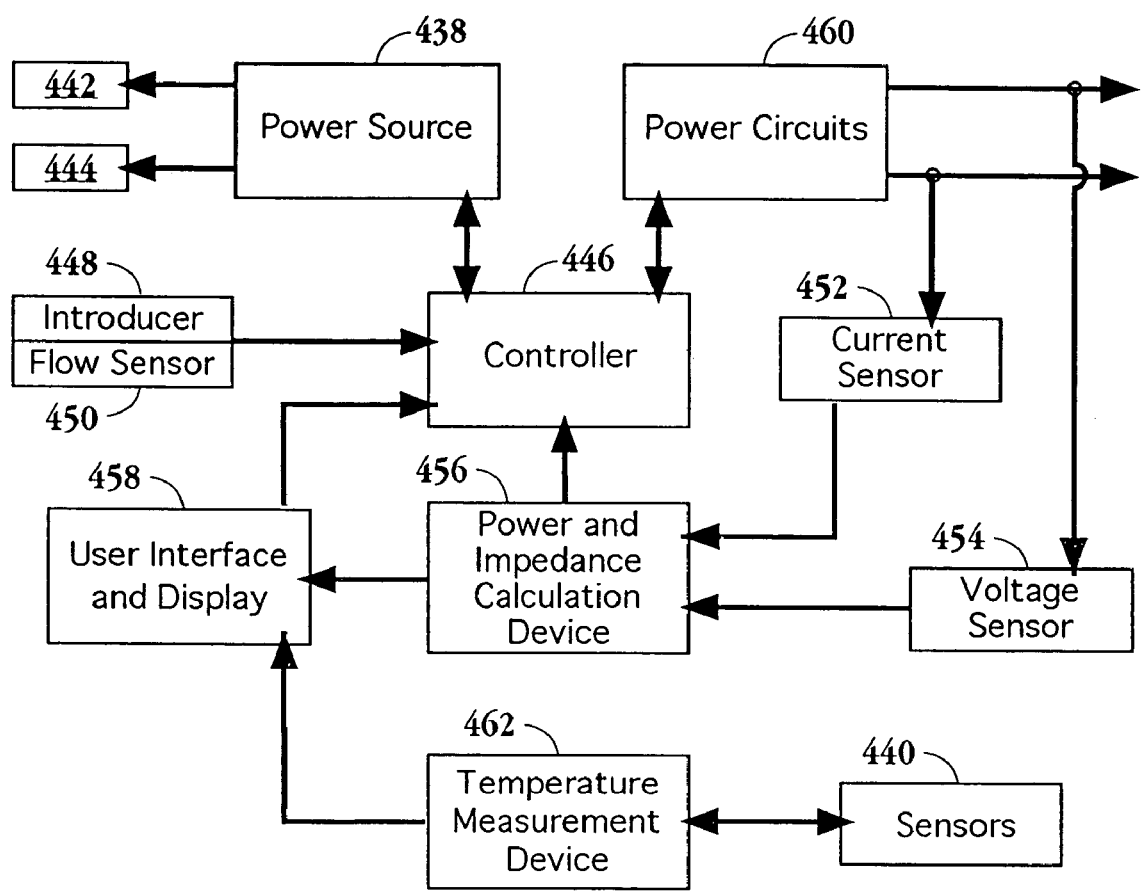
FIG. 34 illustrates a block diagram of a feedback control system of the bone treatment system of an embodiment.
Figure 35:
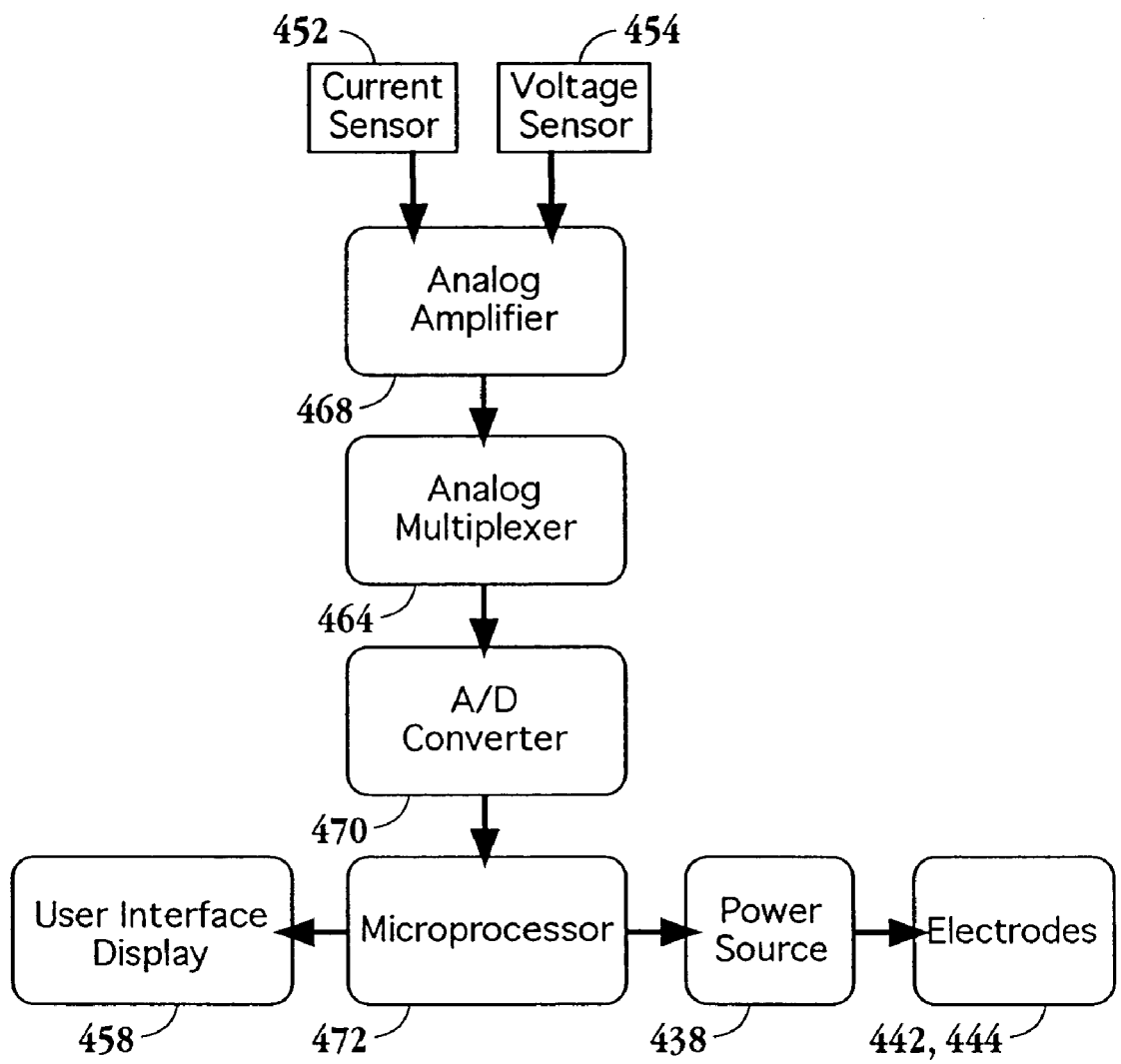
FIG. 35 illustrates a block diagram of a feedback control system of an alternative embodiment, including an analog amplifier, analog multiplexer, and microprocessor.

FIG. 34 is a block diagram of a feedback control system of the bone treatment system of an embodiment. FIG. 35 is a block diagram of a feedback control system of an alternative embodiment, including an analog amplifier, analog multiplexer, and microprocessor. A feedback control system 436 can be coupled to energy source 438, sensors 440, and energy delivery devices 442 and 444. Feedback control system 436 receives temperature or impedance data from sensors 440 and the amount of electromagnetic energy received by energy delivery devices 442 and 444 is modified from an initial setting of ablation energy output, ablation time, temperature, and current density (the "Four Parameters"). Feedback control system 436 can automatically change any of the Four Parameters. Feedback control system 436 can detect impedance or temperature and change any of the Four Parameters. Feedback control system 436 can include a multiplexer to multiplex different antennas, a temperature detection circuit that provides a control signal representative of temperature or impedance detected at one or more sensors 440. A microprocessor can be coupled to the temperature control circuit.

The following discussion pertains particularly to the use of an RF energy source and treatment/ablation apparatus. For purposes of this discussion, energy delivery devices 442 and 444 are referred to as RF electrodes/antennas 442 and 444 and energy source 438 is an RF energy source. However it will be appreciated that all other energy delivery devices and sources discussed herein are equally applicable and devices similar to those associated with lung treatment/ablation apparatus can be utilized with laser optical fibers, microwave devices and the like. The temperature of the tissue, or of RF electrodes 442 and 444 is monitored, and the output power of energy source 438 adjusted accordingly. The physician can, if desired, override the closed or open loop system.

The user of the apparatus can input an impedance value that corresponds to a setting position located at the apparatus. Based on this value, along with measured impedance values, feedback control system 436 determines an optimal power and time needed in the delivery of RF energy. Temperature is also sensed for monitoring and feedback purposes. Temperature can be maintained to a certain level by having feedback control system 436 adjust the power output automatically to maintain that level.

In another embodiment, feedback control system 436 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 444 from the distal end of introducer 448 to a position corresponding to a desired lesion size and monitoring the temperature at the periphery of the lesion such that a temperature sufficient to produce a lesion is attained.

The closed loop system 436 can also utilize a controller 446 to monitor the temperature, adjust the RF power, analyze the result, refeed the result, and then modulate the power. More specifically, controller 446 governs the power levels, cycles, and duration that the RF energy is distributed to electrodes 442 and 444 to achieve and maintain power levels appropriate to achieve the desired treatment objectives and clinical endpoints. Controller 446 can also in tandem govern the delivery of electrolytic, cooling fluid and, the removal of aspirated tissue. Controller 446 can also in tandem monitor for pressure leaks (via pressure flow sensors 450) through introducer 448 tending to cause pneumothorax and actuate coupled control valves to block the fluid path causing the leak and/or initiate the delivery of sealant X and/or energy at the target tissue site to seal the leak. Controller 446 can be integral to or otherwise coupled to power source 438. The controller 446 can be also be coupled to an input/output (I/O) device such as a keyboard, touchpad, PDA, microphone (coupled to speech recognition software resident in controller 446 or other computer) and the like.

With reference to FIG. 34, current delivered through RF electrodes 442 and 444 (also referred to as primary and secondary RF electrodes/antennas) is measured with a current sensor 452. Voltage is measured with a voltage sensor 454. Impedance and power are then calculated using the power and impedance calculation device 456. These values can then be displayed at a user interface and display 458. Signals representative of power and impedance values are received by controller 446 which can be a microprocessor.

A control signal is generated by controller 446 that is proportional to the difference between an actual measured value, and a desired value. The control signal is used by power circuits 460 to adjust the power output in an appropriate amount in order to maintain the desired power delivered at the respective primary and/or secondary antennas 442 and 444. In a similar manner, temperatures detected at sensors 440 provide feedback for maintaining a selected power. The actual temperatures are measured at temperature measurement device 462, and the temperatures are displayed at user interface and display 458. A control signal is generated by controller 446 that is proportional to the difference between an actual measured temperature, and a desired temperature. The control signal is used by power circuits 460 to adjust the power output in an appropriate amount in order to maintain the desired temperature delivered at the respective sensor 440. A multiplexer 464 can be included to measure current, voltage and temperature, at the numerous sensors 440 as well as deliver and distribute energy between primary electrodes 442 and secondary electrodes 444.

Controller 446 can be a digital or analog controller, or a computer with embedded, resident or otherwise coupled software. When controller 446 is a computer it can include a CPU or other processor coupled through a system bus. Further, a keyboard, a disk drive, other non-volatile memory systems, a display, and other peripherals, may be coupled to the system bus. Also coupled to the bus are a program memory and a data memory. In various embodiments controller 446 can be coupled to imaging systems, including but not limited to ultrasound, CT scanners, X-ray, MRI, mammographic X-ray and the like. Further, direct visualization and tactile imaging can be utilized.

User interface and display 458 can include operator controls and a display. In an embodiment user interface 458 can be a personal digital assistant (PDA) or other portable computing device. Interface 458 can be configured to allow the user to input control and processing variables, to enable the controller to generate appropriate command signals. Interface 458 can also receives real-time processing feedback information from one or more sensors 440 for processing by controller 446, to govern the delivery and distribution of energy, fluid etc.

The controller 446 uses the current sensor 452 and voltage sensor 454 outputs to maintain a selected power level at the primary and secondary antennas 442 and 444. The amount of RF energy delivered controls the amount of power. A profile of power delivered can be incorporated in controller 446, and a preset amount of energy to be delivered can also be profiled.

Controller 446 manages process control via control of the following: (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 440. A controller 446 can be incorporated into feedback control system 436 to switch power on and off, as well as modulate the power. Also, with the use of sensor 440 and feedback control system 436, tissue adjacent to RF electrodes 442 and 444 can be maintained at a desired temperature for a selected period of time without causing a shut down of the power circuit to electrode 442 due to the development of excessive electrical impedance at electrode 442 or adjacent tissue.

Referring to FIG. 35, current sensor 452 and voltage sensor 454 are coupled to the input of an analog amplifier 468. Analog amplifier 468 can be a conventional differential amplifier circuit for use with sensors 440. The output of analog amplifier 468 is sequentially coupled via an analog multiplexer 464 to the input of A/D converter 470. The output of analog amplifier 468 is a voltage which represents the respective sensed temperatures. Digitized amplifier output voltages are supplied by A/D converter 470 to a microprocessor 472. Microprocessor 472 may be Model No. 68HCII available from Motorola. However, it will be appreciated that any suitable microprocessor or general purpose digital or analog computer can be used to calculate impedance or temperature.

Microprocessor 472 sequentially receives and stores digital representations of impedance and temperature. Each digital value received by microprocessor 472 corresponds to different temperatures and impedances. Calculated power and impedance values can be indicated on user interface and display 458. Alternatively, or in addition to the numerical indication of power or impedance, calculated impedance and power values can be compared by microprocessor 472 with power and impedance limits. When the values exceed predetermined power or impedance values, a warning can be given on user interface and display 458, and additionally, the delivery of RF energy can be reduced, modified or interrupted. A control signal from microprocessor 472 can modify the power level supplied by energy source 438 to RF electrodes 442 and 444. In a similar manner, temperatures detected at sensors 440 provide feedback for determining the extent and rate of (i) tissue hyperthermia (ii) cell necrosis; and (iii) when a boundary of desired cell necrosis has reached the physical location of sensors 440.

III. Treatment Method

In another aspect, the invention includes a method of palliatively treating a pain-causing tumor on or in a bone. In the first step of the method, the treating worker, e.g., physician, locates the position of the painful bone tumor. This is done conventionally by palpating the area of pain, and optionally, employing known imaging techniques, such as X-ray graphs, computerized tomography, MRI, scintigraphy, or ultrasound imaging to locate one or more specific tumor areas of interest and, optionally, to map the extent of the tumor lesion.

Once a tumor lesion is located, the physician inserts the ablating instrument into the target site. If the instrument has a fixed distal-end tip or structure, e.g., needle or electrode, the instrument is preferably manipulated to place the tip in the tumor, e.g., below the periosteum and into the mass of a tumor on the external surface of the bone cortex. If the instrument has one or more deployable electrodes, the instrument introducer, with the electrodes in a retracted position, is introduced into the patient so that the distal end of the introducer is placed against or adjacent the target tumor. The position of the introducer with respect to the target area can be confirmed by conventionally imaging techniques, as above. Once the instrument is so positioned, the electrode(s) are deployed so that they contact, and preferably are positioned within the target tumor mass.

As indicated above, the electrodes, and particularly deployable electrodes, can be shaped so that in the deployed state they form a desired geometric configuration. For example, if the tumor has a significant planar expanse, the electrodes may be shaped to fan out during deployment to form a substantially planar configuration or array. Likewise, if the tumor mass extends about a portion of the exterior of the cortex of a long bone, the electrodes may fan out during deployment to form a bone-embracing array. This array would define a volume that converges on the distal end of the introducer, i.e., expands on moving away from the distal end. Alternatively, the electrodes might be shaped to curve back in the direction of the distal end of the introducer, that is, define a volume that includes the distal end of the introducer. To this end, the user may preshape or vary the length of one or more of the electrodes, to form an electrode geometry that matches the target region of an individual patient when the electrodes are deployed.

With the ablating structure inserted into the bone tumor, the activating device is activated to produce ablation at the target site. In the preferred embodiment above, this step involves applying an RF current to one or more electrode structures carried on or deployed from an introducer. Power and duration levels for application of RF current are detailed above. Typically, ablation is carried out until a desired end point is reached. The end point may be a selected temperature, e.g., 50° C. or greater, a selected temperature over a give time period, e.g., 50° C. for a period or 5–20 minutes, or a rapid increase in impedance.

The invention also contemplates injecting a liquid into or adjacent the tumor target region either before, during, or following the ablating step. In one embodiment, the injected liquid is used to promote ablation. For example, prior to or during RF ablation, an electrolyte solution is injected into the tumor, either through a conduit in the introducer or through one or more an electrode needles, to enhance the conductivity of the tissue. Thereafter ablation is carried out until a desired end point is reached.

Alternatively, or in addition, the liquid may contain a chemotherapeutic agent, such as any of a number of known anti-tumor compounds. The injection of such an agent into the ablation site may assist in reducing tumor size over a several-day or several-week period, or suppress the metabolic state of unkilled tumor cells at the ablation site.

In one embodiment, the method includes injecting into the tumor site, e.g., into or around the tumor, a polymer liquid that is injected into the target area to form a polymer plug that helps to stabilize the tumor site following ablation. In particular, having a solidified polymer plug in the tumor region can reduce "movement" pain by immobilizing the periosteum in the tumor region or by immobilizing the tumor itself.

Two general types of polymers are useful in the invention. Thermoplastic polymers, such as polymethylmethacrylate, have glass transition temperatures at which the polymer will reversibly change from liquid to solid form. For purposes of this invention, the thermoplastic polymer is one having a glass transition above body temperature, allowing the polymer to be injected in a viscous liquid form above its glass transition temperature, with cooling and solidifying occurring once injected into the tumor area. To this end, where the ablating is produced by heat generation, e.g., RF current, the polymer is preferably injected during the heat-ablating step, through a needle electrode which is maintained above the glass transition temperature during ablation. Thereafter, the injected polymer liquid cools and solidifies at the injection site.

Alternatively, the polymer may be a thermoset polymer which is formulated, prior to injection, to cross-link and solidify within a given period after injection, or is formulated to undergo accelerated cross-linking when in contact with the heated needle and/or target tissue, as part of a tissue-ablation step. Biocompatible thermoset polymers with these setting characteristics are well known to those skilled in the art.

To illustrate the method, a study was performed to evaluate the efficacy of percutaneous radio-frequency ablation as a method to provide palliative pain relief for patients with metastatic lesions involving bone. The goals of the study were as follows: determine the safety of percutaneous RF ablation of painful metastases involving bone; and determine the efficacy of RF ablation to provide pain relief from osteolytic metastases by assessing pain intensity and quality of life before and after therapy using a standardized Brief Pain Inventory (BIP). This study demonstrates, as described below, that RF ablation provides a potential alternative method for palliation of painful osteolytic metastatic lesions; this procedure is safe and the relief of pain is dramatic. Importantly, the quality of life for these patients is improved with this therapy. The RF ablation device employed was a Rita Medical System, Inc. (Mt View, Calif.) Model 1500 Generation employing a Starburst or Starburst XL probe having seven or nine electrodes, respectively, with 3-cm or 5-cm ablation volume diameter.

FIG. 36 is a table showing tumor type and treatment parameters for a patient treatment study involving methods and embodiments of the bone treatment apparatus. Over a 10-month period, twelve adult patients with painful osteolytic metastatic lesions were treated. These patients had failed conventional radiation treatment and/or chemotherapy with 24/10 worst pain over a 24 h period, and were treated with percutaneous CT or US-guided radio-frequency (RF) ablation with a multi-tip needle (Starburst XL electrode, RITA Medication Systems, Mountain View, Calif.) under general anesthesia. Once the target temperature of 100° C. was obtained, this temperature was maintained for a minimum of 5 min with a goal of 5–15 min. The entire lesion was not completely treated; rather, ablation treatments were focused on the margin of the lesion involving bone with the goal of treating the soft-tissue/bone interface.

Patient pain was measured using the BPI one day after the procedure and then every week for a period of one month and then every other week thereafter for a total follow-up period of 6 months. Patient analgesic use was also recorded at these same follow-up intervals. A follow-up contrast enhanced CT examination was performed one week after the procedure.

Twelve patients were treated with RF ablation. The 8 men and 4 women ranged in age from 56–75 years (mean, 65 years±5 years [standard deviation]). Four patients completed the 24-week follow-up period. Three patients died during the course of the study, unrelated to the RF ablation, 4, 7, and 13 weeks following therapy. One patient suffered a stroke 18 weeks after the RF ablation treatment and is no longer able to complete the BPI questionnaire. The remaining three patients remain in the study with 10, 16 and 16 weeks of follow-up beyond their RF ablation treatment date. Lesion sizes ranged from 1–11 cm. One patient with a large lesion was treated in two sessions, six weeks apart, while the remaining 11 patients were treated in a single session. The range of electrode deployments for the RF ablation procedure was 207 (mean 4.5 deployments±1.6 deployments [standard deviation]. The range for total ablation time was 16–95 minutes (mean, 47 minutes±20 minutes [standard deviation]). The total anesthesia time required for the procedure ranged from 90–187 minutes (mean, 134 minutes±32 minutes [standard deviation]).

The RF ablation proved to be effective for providing palliative pain relief in these patients. These patients derived benefit from the procedure for the six-month follow-up period. Importantly, three of four patients that died during the course of follow-up, unrelated to RF ablation, died with no pain at the treated site. The fourth patient had 2/10 pain at the treated site at the time of death.

The lesions that were treated in this study were predominantly osteolytic with an associated soft tissue component. In all cases, the electrodes were readily deployed into the osteolytic and soft tissue component of the metastatic lesion. The electrode when deployed, maintained it's symmetric shape with typical deployment of the electrode tips at the bone/soft-tissue interface. There were no major complications.

These results show that tumor ablation provides an attractive adjunct or alternative to the use of radiation therapy for palliation of painful metastatic lesions. In cases where radiation therapy fails or further treatment is not possible, RF ablation will provide a method for palliation of pain for these difficult to treat patients.

The apparatus and method of this invention are particularly useful for obtaining biopsy tissue samples and treating the bone for various diseases including benign and cancerous tumors. It will be readily apparent to a person skilled in the art that various embodiments and combinations of embodiments of the device and method can be used to sample or ablate/destroy body tissues, tissue locations that are accessible by percutaneous or endoscopic catheters, and is not limited to the bone. Such tissue locations and organs include, but are not limited to, the heart and cardiovascular system, upper respiratory tract and gastrointestinal system. Application of the apparatus and method in all of these organs and tissues are intended to be included within the scope of this invention.

In general, alternatives and alternative embodiments described herein are substantially similar to previously described embodiments, and common elements and acts or steps are identified by the same reference numbers. Only significant differences in construction or operation are described in detail. The elements and acts of the various embodiments described above can be combined to provide further embodiments.

All of the above references and U.S. patents and applications are incorporated herein by reference. Aspects of the invention can be modified, if necessary, to employ the systems, functions and concepts of the various patents and applications described above to provide yet further embodiments of the invention.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings of the invention provided herein can be applied to other treatment systems, not only for the bone treatment system described above.

The invention claimed is:

1. A system for palliatively treating a pain-causing tumor on or in a bone, comprising:
    an instrument having a distal-end structure adapted to be inserted into the bone tumor, said distal-end structure being activatable to ablate tumor tissue,
    connecting structure for connecting said distal-end structure to an activating device, and
    a source of polymer liquid operatively connected to the instrument for delivery of the liquid through the instrument and into the tumor.

2. The system of claim 1, wherein the instrument includes a probe with a distal end, and at least one electrode movable from a retracted position within the probe to a deployed position extending from the probe's distal end, forming said distal-end structure when deployed.

3. The system of claim 2, wherein said instrument includes a plurality of curved, deployable electrodes which, when deployed, form an array of deployed electrodes that defines a substantially two-dimensional surface expanse or a three-dimensional volume within the tumor.

4. The system of claim 3, for use in treating a bone tumor on the exterior or interior surface of a compact region of a bone, wherein said electrodes, when deployed, form an array that defines a two-dimensional expanse that is coextensive with a portion of the surface of the compact bone region surrounded by said tumor.

5. The system of claim 3, wherein said electrodes, when deployed form a three-dimensional volume that encompasses said distal end, or a three-dimensional volume that converges at said distal end.

6. The system of claim 3, wherein the curvature of at least one of said electrodes is shapable, prior to use, such that the electrode(s), when inserted into the tumor, define a selected geometry within the tumor.

7. The system of claim 3, wherein at least one of said electrodes is a needle forming a conduit through which liquid can be injected into the tumor.

8. The system of claim 3, wherein said probe includes a conduit through which fluid can be injected into the region of the tumor.

9. The system of claim 1, wherein said connecting structure is adapted to connect said distal-end structure to a source of RE current.

10. A method of palliatively treating a pain-causing tumor on or in a bone, comprising:
    locating the position of the bone tumor,
    positioning against or adjacent the located bone tumor, a distal end of an instrument having a distal-end structure which can be activated to ablate tissue,
    with said distal end inserted into the bone tumor, activating the distal-end structure under conditions effective to ablate at least a portion of the; and
    injecting a polymer liquid into the tumor.

11. The method of claim 10, wherein said distal-end structure includes at least one electrode, and said activating includes applying an RF current to said electrode(s).

12. The method of claim 10, wherein said instrument includes a probe with a distal end, and at least one electrode movable from a retracted position within the probe to a deployed position extending from the probe's distal end, to form said distal-end structure when deployed, and said method further includes deploying said electrode(s) when the distal end of the probe is positioned against or adjacent the bone tumor.

13. The method of claim 12, wherein said instrument includes a plurality of curved, deployable electrodes, and said deploying is effective to create an array of deployed electrodes that defines a substantially two-dimensional surface expanse or a three-dimensional volume within the tumor.

14. The method of claim 13, for use in treating a bone tumor on the exterior or interior surface of a compact region of a bone, wherein said electrodes, when deployed, create an array that defines a two-dimensional expanse that is coextensive with a portion of the surface of the compact bone region surrounded by said tumor.

15. The method of claim 13, wherein said electrodes, when deployed, form a three-dimensional volume that encompasses said probe distal end.

16. The method of claim 13, wherein said electrodes, when deployed form a three-dimensional volume that converges at said probe distal end.

17. The method of claim 13, wherein the curvature of at least one of said electrodes is shapable, prior to said positioning, such that the electrode(s), when inserted into the tumor, define a selected geometry within the tumor.

18. The method of claim 10, wherein said distal-end structure includes at least one electrode, said activating includes applying an RF current to said electrode(s).

19. The method of claim 10, further comprising injecting an electrolyte solution into the tumor, prior to or during said activating step, to enhance the conductivity of the tumor during the applying of RF current to the electrode(s).

20. The method of claim 10, wherein said injecting includes injecting the polymer liquid into the tumor, before, during or following said activating step, such that the needle and surrounding tumor region is at a temperature that allows introduction of the polymer liquid through the needle and hardening at the site of injection.

21. The method of claims 10 or 19, wherein at least one of said electrode(s) is a needle through which at least one of said polymer liquid and electrolyte solution can be injected into the tumor.

22. The method of claim 10, wherein said polymer liquid is a polymethylmethacrylate.

23. The method of claim 10, wherein said injecting includes injecting the polymer liquid through an electrode needle, and said activating is effective to maintain the temperature of the polymer liquid above its glass transition temperature while the liquid is being injected into the tumor.

* * * * *